United States Patent
Ganuza Taberna et al.

(10) Patent No.: US 10,240,120 B2
(45) Date of Patent: *Mar. 26, 2019

(54) BALANCED MIXOTROPHY METHOD

(71) Applicant: Heliae Development LLC, Gilbert, AZ (US)

(72) Inventors: Eneko Ganuza Taberna, Phoenix, AZ (US); Jason D Licamele, Scottsdale, AZ (US); Anna Lee Tonkovich, Gilbert, AZ (US); Michael V Bellefeuille, Mesa, AZ (US); Cameron Wyatt, Gilbert, AZ (US); Thomas J Kulaga, Chandler, AZ (US); Adriano Galvez, III, Gilbert, AZ (US)

(73) Assignee: Heliae Development LLC, Gilbert, AZ (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/699,659

(22) Filed: Apr. 29, 2015

(65) Prior Publication Data

US 2015/0240199 A1 Aug. 27, 2015
US 2019/0010443 A9 Jan. 10, 2019

Related U.S. Application Data

(63) Continuation of application No. PCT/US2013/069047, filed on Nov. 8, 2013.

(60) Provisional application No. 61/891,990, filed on Oct. 17, 2013, provisional application No. 61/798,969, filed on Mar. 15, 2013, provisional application No. 61/724,710, filed on Nov. 9, 2012.

(51) Int. Cl.
*C12N 1/12* (2006.01)
*C12Q 3/00* (2006.01)

(52) U.S. Cl.
CPC ........ *C12N 1/12* (2013.01); *C12Q 3/00* (2013.01)

(58) Field of Classification Search
CPC .......... C12N 1/12; C12N 15/52; C12N 15/70; C12N 9/0006; C12N 9/0051; C12N 15/74; C12N 1/20; C12N 1/36; C12N 1/32; C12N 9/0067; C12N 15/8243; C12N 15/8247; C12N 1/38; C12N 9/00; C12N 1/16; C12N 15/79; C12N 9/0008; C12N 9/1205; C12N 9/14; C12N 9/16; C12N 9/20; C12N 9/2408; C12N 9/2431; C12N 9/88; C12N 1/34; C12N 9/001; C12N 9/1025; C12N 9/1029; C12N 9/13; C12N 9/90; C12N 9/93; C12M 21/02; C12M 41/18; C12M 41/00; C12M 41/26; C12M 23/26; C12M 29/06; C12M 43/02; C12M 43/08; C12M 23/06; C12M 23/44; C12M 29/00; C12M 41/12; C12M 41/32; C12M 41/34; C12M 23/22; C12M 23/58; C12M 31/02; C12M 41/48; C12M 23/00; C12M 23/38; C12M 23/48; C12M 27/20; C12M 29/20; C12M 33/00; C12M 35/00; C12M 39/00; C12M 41/06; C12M 41/36; C12M 29/18; C12M 31/10; C12M 23/18; C12M 23/34; C12M 27/06; C12M 41/24; A61K 2300/00; A61K 31/202; A61K 31/20; A61K 36/02; E21B 43/16; E21B 21/00; E21B 21/062; E21B 43/26; A23V 2002/00; A23V 2250/1868; A23V 2250/187; C12P 7/16; C12P 7/6427; C12P 7/6472; C12P 5/00; C12P 7/00; C12P 7/40; Y02E 50/10; A23L 33/12; C12Y 101/05006; C12Y 108/05004; C12Y 101/01027; C12Y 101/99007; C12Y 102/01002; C12Y 102/0101; C12Y 102/01043; C12Y 103/01084; C12Y 203/01054; C12Y 203/03005; C12Y 208/03; C12Y 401/01031; C12Y 403/01006; C12Y 403/01019; C12Y 404/01001; C12Y 503/01027; C12Y 602/01036; C01C 1/04; C12Q 3/00; A01G 33/00; A23C 2230/10; A23C 9/1528; A23K 20/158; C11B 1/10; C07C 1/04; C07C 67/02
See application file for complete search history.

(56) References Cited

U.S. PATENT DOCUMENTS

| | | | |
|---|---|---|---|
| 3,316,674 | A | 5/1967 | Shirota et al. |
| 3,320,693 | A | 5/1967 | Shirota et al. |
| 3,389,998 | A | 6/1968 | Jorgensen |
| 3,444,647 | A | 5/1969 | Takahashi |

(Continued)

FOREIGN PATENT DOCUMENTS

| | | |
|---|---|---|
| CN | 1293963 | 5/2001 |
| CN | 102060578 A | 5/2011 |

(Continued)

OTHER PUBLICATIONS

"Algal Culturing Techniques," Edited by Robert A. Anderson, Elsevier Academic Press, 2005, 589 pages IBSN: 0-12-088426-7.
(Continued)

*Primary Examiner* — Deborah K Ware
(74) *Attorney, Agent, or Firm* — Heliae Development LLC; Veronica-Adele R. Cao

(57) ABSTRACT

Methods of culturing mixotrophic microorganisms in a state of balanced gas composition are disclosed. Parameters of a culture of mixotrophic microorganisms may be controlled to reduce the requirements of externally supplied gases and optimize the production and consumption of gases within the culture by the phototrophic and heterotrophic metabolisms of the mixotrophic microorganisms.

20 Claims, 3 Drawing Sheets

(56) References Cited

U.S. PATENT DOCUMENTS

| | | | |
|---|---|---|---|
| 3,773,523 A | 11/1973 | Chhuy et al. |
| 3,955,318 A | 5/1976 | Hulls |
| 4,005,546 A | 2/1977 | Oswald |
| 4,267,038 A | 5/1981 | Thompson |
| 4,551,164 A | 11/1985 | Tenzer |
| 4,666,497 A | 5/1987 | Tenzer |
| 4,744,996 A | 5/1988 | Rakow |
| 4,846,870 A | 7/1989 | Weltzien |
| 4,919,702 A | 4/1990 | Weltzien |
| 4,966,096 A | 10/1990 | Adey |
| 4,966,713 A | 10/1990 | Keys |
| 5,011,604 A | 4/1991 | Wilde |
| 5,097,795 A | 3/1992 | Adey |
| 5,137,828 A | 8/1992 | Robinson |
| 5,151,347 A | 9/1992 | Delente |
| 5,229,146 A | 7/1993 | Tanaka |
| 5,271,831 A | 12/1993 | Oremland |
| 5,360,730 A | 11/1994 | Orndorff |
| 5,527,456 A | 6/1996 | Jensen |
| 5,541,056 A | 7/1996 | Huntley |
| 5,591,341 A | 1/1997 | Jensen |
| 5,707,868 A | 1/1998 | Boulay |
| 5,846,423 A | 12/1998 | Jensen |
| 5,851,398 A | 12/1998 | Adey |
| 6,022,701 A | 2/2000 | Boussiba |
| 6,083,293 A | 7/2000 | Bath |
| 6,083,740 A | 7/2000 | Kodo |
| 6,190,913 B1 | 2/2001 | Singh |
| 6,197,303 B1 | 3/2001 | Gedouin |
| 6,203,700 B1 | 3/2001 | Rose |
| 6,262,316 B1 | 7/2001 | Wadstrom |
| 6,338,866 B1 | 1/2002 | Criggall |
| 6,391,638 B1 | 5/2002 | Schaaltiel |
| 6,461,853 B1 | 10/2002 | Zhu |
| 6,465,240 B1 | 10/2002 | Wexler |
| 6,509,178 B1 | 1/2003 | Tanaka |
| 6,596,288 B2 | 7/2003 | Gedouin |
| 6,627,201 B2 | 9/2003 | Ichinose |
| 6,773,594 B1 | 8/2004 | vanderWijngaart |
| 6,858,430 B1 | 2/2005 | Reddy |
| 6,896,804 B2 | 5/2005 | Haerther |
| 6,923,967 B1 | 8/2005 | Lignell |
| 6,977,166 B1 | 12/2005 | Ratledge |
| 6,986,323 B2 | 1/2006 | Ayers |
| 7,001,519 B2 | 2/2006 | Linden |
| 7,030,061 B2 | 4/2006 | DeLaFuenteJimenez |
| 7,067,158 B2 | 6/2006 | Larkins |
| 7,172,691 B2 | 2/2007 | Dunlop |
| 7,300,583 B1 | 11/2007 | Heppenstall |
| 7,303,753 B2 | 12/2007 | Majmudar |
| 7,563,463 B2 | 7/2009 | Renimel |
| 7,566,551 B2 | 7/2009 | Zhang |
| 7,618,813 B2 | 11/2009 | Lee |
| 7,674,609 B2 | 3/2010 | Ratledge |
| 7,736,508 B2 | 6/2010 | Limcaco |
| 7,776,211 B2 | 8/2010 | Limcaco |
| 7,850,848 B2 | 12/2010 | Limcaco |
| 7,892,311 B2 | 2/2011 | Briand |
| 7,905,930 B2 | 3/2011 | Oyler |
| 7,914,832 B2 | 3/2011 | Uchino |
| 7,927,491 B2 | 4/2011 | Kotelko |
| 7,951,296 B2 | 5/2011 | Williams |
| 7,977,076 B2 | 7/2011 | Oyler |
| 7,977,085 B2 | 7/2011 | Rispoli |
| 7,981,292 B2 | 7/2011 | Limcaco |
| 7,985,338 B1 | 7/2011 | Chong |
| 8,003,379 B2 | 8/2011 | Goldman |
| 8,017,377 B1 | 9/2011 | Much |
| 8,080,679 B2 | 12/2011 | Hatcher |
| 8,092,678 B2 | 1/2012 | Ott |
| 8,097,168 B2 | 1/2012 | Theodore |
| 8,101,080 B2 | 1/2012 | Robinson |
| 8,119,583 B2 | 2/2012 | Day |
| 8,122,637 B2 | 2/2012 | Blotsky |
| 8,143,051 B2 | 3/2012 | Weissman |
| 8,187,849 B2 | 5/2012 | Larsen |
| 8,206,721 B2 | 6/2012 | Stutz |
| H2271 H | 7/2012 | Sears |
| 8,357,510 B2 | 1/2013 | Weiss |
| 8,367,383 B2 | 2/2013 | Zhu |
| 8,372,408 B2 | 2/2013 | Nizard |
| 8,475,543 B2 | 7/2013 | Oyler |
| 8,518,690 B2 | 8/2013 | Beliaev |
| 8,877,465 B2 | 11/2014 | Geiringer |
| 2002/0009479 A1 | 1/2002 | Vardi |
| 2003/0017558 A1 | 1/2003 | Pham |
| 2003/0091560 A1 | 5/2003 | Kobilke |
| 2003/0133961 A1 | 7/2003 | Nakamura |
| 2003/0152587 A1 | 8/2003 | Kralovec |
| 2003/0198730 A1 | 10/2003 | Stewart |
| 2003/0211594 A1 | 11/2003 | Rosebrook |
| 2004/0013622 A1 | 1/2004 | Godbout |
| 2004/0131580 A1 | 7/2004 | Hagino |
| 2004/0234476 A1 | 11/2004 | Guglielmo |
| 2005/0119127 A1 | 6/2005 | Cambri |
| 2005/0250190 A1 | 11/2005 | Ratledge |
| 2005/0266018 A1 | 12/2005 | Boreyko |
| 2006/0166825 A1 | 7/2006 | Goulet |
| 2007/0048848 A1 | 3/2007 | Sears |
| 2007/0148726 A1 | 6/2007 | Auton |
| 2007/0167396 A1 | 7/2007 | Dillon |
| 2007/0167397 A1 | 7/2007 | Dillon |
| 2007/0190595 A1 | 8/2007 | Weiss |
| 2007/0196893 A1 | 8/2007 | Weiss |
| 2007/0248693 A1 | 10/2007 | Mazzio |
| 2007/0264708 A1 | 11/2007 | Bayless |
| 2008/0124286 A1 | 5/2008 | Lisson |
| 2008/0286252 A1 | 11/2008 | Sinnott |
| 2008/0299257 A1 | 12/2008 | Uchino |
| 2009/0028897 A1 | 1/2009 | Maestro |
| 2009/0068715 A1 | 3/2009 | Ogaki |
| 2009/0130139 A1 | 5/2009 | Mekideche |
| 2009/0142369 A1 | 6/2009 | Shih |
| 2009/0142429 A1 | 6/2009 | Belas |
| 2009/0148928 A1 | 6/2009 | Hackworth |
| 2009/0162922 A1 | 6/2009 | DeMattia |
| 2009/0197312 A1 | 8/2009 | Pastinen |
| 2009/0301399 A1 | 12/2009 | Brown |
| 2009/0304810 A1 | 12/2009 | Martin |
| 2009/0305389 A1 | 12/2009 | Willson |
| 2010/0003275 A1 | 1/2010 | Pasco |
| 2010/0028376 A1 | 2/2010 | Einarsson |
| 2010/0069492 A1 | 3/2010 | Geiringen |
| 2010/0105126 A1 | 4/2010 | Wright |
| 2010/0190227 A1 | 7/2010 | Dauth |
| 2010/0210002 A1 | 8/2010 | McCaffrey |
| 2010/0236135 A1 | 9/2010 | Kleinberger |
| 2010/0239712 A1 | 9/2010 | Brooks |
| 2010/0242355 A1 | 9/2010 | Blotsky |
| 2010/0260887 A1 | 10/2010 | Ufaz |
| 2010/0264094 A1 | 10/2010 | Schwartz |
| 2010/0267122 A1 | 10/2010 | Chinnasamy |
| 2010/0272940 A1 | 10/2010 | Shi |
| 2010/0285105 A1 | 11/2010 | Radianingtyas |
| 2010/0311146 A1 | 12/2010 | Auton |
| 2010/0323414 A1 | 12/2010 | Trimbur |
| 2010/0330653 A1 | 12/2010 | Hazlebeck |
| 2011/0070632 A1 | 3/2011 | Katoch |
| 2011/0081706 A1 | 4/2011 | Schlesinger |
| 2011/0091945 A1 | 4/2011 | Das |
| 2011/0120944 A1 | 5/2011 | Ma'Ayan |
| 2011/0159581 A1 | 6/2011 | Zhang |
| 2011/0190522 A1 | 8/2011 | Trimbur |
| 2011/0201063 A1 | 8/2011 | Mitropoulos |
| 2011/0247262 A1 | 10/2011 | Lee |
| 2011/0247977 A1 | 10/2011 | Song |
| 2011/0281295 A1 | 11/2011 | Sylvestre |
| 2011/0296756 A1 | 12/2011 | Zhang |
| 2012/0011620 A1 | 1/2012 | Gordon |
| 2012/0021477 A1 | 1/2012 | Bernard |
| 2012/0028338 A1 | 2/2012 | Bhatnagar |
| 2012/0055077 A1 | 3/2012 | Savage |
| 2012/0079760 A1 | 4/2012 | Savage |
| 2012/0088296 A1 | 4/2012 | Vargas |

(56) References Cited

U.S. PATENT DOCUMENTS

| | | |
|---|---|---|
| 2012/0107919 A1 | 5/2012 | Broneske |
| 2012/0116138 A1 | 5/2012 | Goodall |
| 2012/0171733 A1 | 7/2012 | Im |
| 2012/0175301 A1 | 7/2012 | Komor |
| 2012/0183572 A9 | 7/2012 | Sayre |
| 2012/0192605 A1 | 8/2012 | McSpaddenGardener |
| 2012/0247164 A1 | 10/2012 | Dahms |
| 2012/0264177 A1 | 10/2012 | Avila |
| 2012/0266530 A1 | 10/2012 | Ellis |
| 2012/0276174 A1 | 11/2012 | Johnson |
| 2012/0302806 A1 | 11/2012 | Hatcher |
| 2013/0004646 A1 | 1/2013 | Franklin |
| 2013/0028929 A1 | 1/2013 | Kim |
| 2013/0042522 A1 | 2/2013 | Delobel |
| 2013/0061517 A1 | 3/2013 | Hazlebeck |
| 2013/0164796 A1 | 6/2013 | Licamele |
| 2013/0164812 A1 | 6/2013 | Nicholas |
| 2013/0171702 A1 | 7/2013 | Calleja |
| 2013/0199687 A1 | 8/2013 | Sugimoto |
| 2013/0210095 A1 | 8/2013 | Calleja |
| 2014/0074769 A1 | 3/2014 | Cushing |
| 2014/0293238 A1 | 10/2014 | Ueoka |
| 2014/0298717 A1 | 10/2014 | Ayers |
| 2014/0299867 A1 | 10/2014 | Ono |
| 2014/0300693 A1 | 10/2014 | Hirata |

FOREIGN PATENT DOCUMENTS

| | | |
|---|---|---|
| CN | 102173922 | 9/2011 |
| CN | 102173926 | 9/2011 |
| EP | 0972506 A1 | 1/2000 |
| EP | 1681060 A1 | 7/2006 |
| EP | 1806411 B1 | 12/2008 |
| EP | 1811848 B1 | 12/2010 |
| FR | 2941157 | 7/2010 |
| GB | 1493480 | 11/1977 |
| JP | 0622772 A | 2/1994 |
| JP | 2011254724 A | 12/2011 |
| JP | 201223978 | 2/2012 |
| JP | 2012023978 A | 2/2012 |
| RU | 2004129362 A | 3/2006 |
| WO | 1987002659 A1 | 5/1987 |
| WO | 9118108 | 1/1991 |
| WO | 200104338 | 1/2001 |
| WO | 2001004338 A1 | 1/2001 |
| WO | 2001022834 A2 | 4/2001 |
| WO | 0181603 | 11/2001 |
| WO | 2001081603 A2 | 11/2001 |
| WO | 2004043139 A2 | 5/2004 |
| WO | 2004085343 A1 | 10/2004 |
| WO | 2005006838 A2 | 1/2005 |
| WO | 2005121309 A1 | 12/2005 |
| WO | 2007068945 A1 | 6/2007 |
| WO | 2008004900 A1 | 1/2008 |
| WO | 2008151149 A2 | 12/2008 |
| WO | 2008151373 A1 | 12/2008 |
| WO | 2008155567 A1 | 12/2008 |
| WO | 2009018230 A1 | 2/2009 |
| WO | 2009073822 | 6/2009 |
| WO | 2009073822 A2 | 6/2009 |
| WO | 2009126843 A2 | 10/2009 |
| WO | 2009134114 A1 | 11/2009 |
| WO | 2010011754 A2 | 1/2010 |
| WO | 2010030823 A1 | 3/2010 |
| WO | 2010046115 | 4/2010 |
| WO | 2010046115 A2 | 4/2010 |
| WO | 2010092243 A1 | 8/2010 |
| WO | 2010108087 A1 | 9/2010 |
| WO | 2010138571 A1 | 12/2010 |
| WO | 2011035166 A1 | 3/2011 |
| WO | 2011060126 A2 | 5/2011 |
| WO | 2012049503 A1 | 4/2012 |
| WO | 2012074502 A1 | 6/2012 |
| WO | 2012109375 | 8/2012 |
| WO | 2012109375 A2 | 8/2012 |
| WO | 2012109642 A1 | 8/2012 |
| WO | 2012135150 A2 | 10/2012 |
| WO | 2012138381 | 10/2012 |
| WO | 2012151382 A1 | 11/2012 |
| WO | 2012153174 A2 | 11/2012 |
| WO | 2012168662 A1 | 12/2012 |
| WO | 2012168663 A1 | 12/2012 |
| WO | 2012175866 A1 | 12/2012 |
| WO | 2013014606 A1 | 1/2013 |
| WO | 2012056187 A2 | 5/2013 |
| WO | 2013069037 A1 | 5/2013 |
| WO | 2013096682 | 6/2013 |
| WO | 2013096682 A1 | 6/2013 |
| WO | 2013096891 A1 | 6/2013 |
| WO | 2013100756 | 7/2013 |
| WO | 2013100756 A2 | 7/2013 |
| WO | 2013126028 A1 | 9/2013 |
| WO | 2013136023 A1 | 9/2013 |
| WO | 2013136024 A1 | 9/2013 |
| WO | 2013136025 A1 | 9/2013 |
| WO | 2013136026 A1 | 9/2013 |
| WO | 2013136027 A1 | 9/2013 |
| WO | 2013136029 A1 | 9/2013 |
| WO | 2014074770 A2 | 5/2014 |
| WO | 2014144270 A1 | 9/2014 |

OTHER PUBLICATIONS

Abou-Shanab et al., "Characterization of Microalgal Species Isolated from Fresh Water Bodies as a Potential Source for Biodiesel Production," Applied Energy, 88, 2011, pp. 3300-3306.

Abreu, et al., "Mixotrophic Cultivation of Chlorella Vulgaris Using Industrial Dairy Waste as Organic Carbon Source," Bioresource Technology, 118, 2012, pp. 61-66.

Acarli et al., "Comparison of *Isochrysis galbana* and *chlorella* sp. Microalgae on Growth and Survival Rate of European Flat Oyster (*Ostrea edulis*, Linnaeus 1975) larvae," Indian Journal of Geo-Marine Science, vol. 40(1), Feb. 2011, pp. 55-58.

Achitouv et al., 'C31-C34 Methylated Squalenes from a Bolivian Strain of Botryococcus Braunii,' Phytochemistry 65, 2004, pp. 3159-3165.

Admiraal et al., "Influence of Organic Compounds and Light Limitation on the Growth Rate of Estuarine Benthic Diatoms," British Phycological Journal, 14:3, Sep. 1979, pp. 197-206, downloaded on Jan. 14, 2013, 11 pages.

Aduriz et al., "Culinary trompe-l'oeil: A New Concept in Coating," International Journal of Gastronomy and Food Science, 1, 2012, pp. 70-77.

Algabloom Technologies, "AlgaBloom Bioreactor with AlgaBag," Sep. 2012, retrieved from http://www.algabioreactor.com/algabloom-algabag/ on Nov. 2, 2012, 2 pages.

Allen et al., "Studies on Nitrogen-Fixing Blue-Green Algae. I. Growth and Nitrogen Fixation by Anabaena Cylindrica Lemm," Plant Physiology, Jul. 1955, 30, pp. 366-372.

Allison et al., "Studies on the Photosynthetic Reaction, I. The Assimilation of Acetate by Nostoc Muscorum," Oct. 1952, downloaded from www.jbc.org on Feb. 22, 2013, pp. 197-205.

Almagro et al., "Class III Peroxidases in Plant Defence Reactions," Journal of Experimental Botany, 2009, vol. 60, No. 2, pp. 377-390.

Alverson et al., "The Model Marine Diatom Thalassiosira Pseudonana Likely Descended from a Freshwater Ancestor in the Genus *Cyclotella*," BMC Evolutionary Biology, 2011, 11, 125, 8 pages.

An et al., "Hydrocarbon Production from Secondarily Treated Piggery Wastewater by the Green Alga *Botryococcus braunii*," Journal of Applied Phycology, 15, 2003, pp. 185-191.

Anderson et al., "Light-Activated Heterotrophic Growth of the *Cyanobacterium synechocystis* sp. Strain PCC 6803: a Blue-Light-Requiring Process," Journal of Bacteriology, May 1991, vol. 173, No. 9, pp. 2761-2767.

Anderson et al., "Photosynthesis in Rhodospirillum Rubrum," Plant Physiol., 1967, 42, pp. 491-496.

Andersson et al., "Nutritional Characteristics of a Mixotrophic Nanoflagellate, *Oschromonas* sp.," Microbial Ecology, 1989, 17, pp. 251-262.

(56) References Cited

OTHER PUBLICATIONS

Andrade, et al., "Mixotrophic Cultivation of Microalga Spirulina Platensis Using Molasses as Organic Substrate," Aquaculture, 264, 2007, pp. 130-134.
Andric et al., "Reactor Design for Minimizing Product Inhibition During Enzymatic Lignocellulose Hydrolysis: I. Significance and Mechanism of Cellobiose and Glucose Inhibition on Cellulolytic Enzymes," Biotechnology Advances, 28, 2010, pp. 308-324.
Arciero et al., "In Vitro Attachment of Bilins to Apophycocyanin, II. Determination of the Structures of Tryptic Bilin Peptides Derived from the Phycocyanobilin Adduct," The Journal of Biological Chemistry, vol. 263, No. 34, Issue of Dec. 1988, pp. 18350-18357.
Arnstein et al., "The Function of Vitamin B12 in the Metabolism of Propionate by the Protozoan Ochromonas malhamensis," Biochem. J., 1962, 83, pp. 264-270.
Arredondo-Vega et al., "Effect of Zeolitic Products in the Nutritive Quality of the Diatom Thalassiosira Weissflogii," Hydrobiologica, 2004, 14, 1, pp. 69-74.
Atalah et al., "Enhancement of Gilthead Seabream (*Sparus aurata*) Larval Growth by Dietary Vitamin E in Relation to Two Different Levels of Essential Fatty Acids," Aquaculture Research, 2012, 43, pp. 1816-1827.
Author Unknown, "Biofuel Breakthrough: Quick Cook Method Turns Algae Into Oil," University of Michigan News Service, Oct. 31, 2012, 3 pages, retrieved from http://www.ns.umich.edu/new/releases/20947-biofuel-breakthrough-quick-cook-method-tu . . . on Jan. 21, 2013.
Author Unknown, "Chapter 4. Chemical Reactions and Stoichiometry," retrieved from www.oneonta.edu/faculty/kotzjc/REVIEW/Ch4Stoichio, date unknown, 52 pages.
Author Unknown, "Chapter 5. Photochemistry of Photosynthesis," 48 pages, retrieved from server2.phys.uniroma1.it/doc/giansanti/BIOFISICA/BIOFISICA_2009-10/MATERIALI/TESTI/NOBEL/5%20-%20Photochemistry%20o%23450921.pdf, date unknown, 48 pages.
Author Unknown, "Fatty Acid Catabolism," Pinnacle Solutions Manual, Chapter 17, 2008, 12 pages.
Author Unknown, "Food for Mars Missions Prepared in Alsace, France?," retrieved from http://www.isunet.edu/news-and-media-center/1179-food-for-mars-missions-prepared-in-a on Jun. 20, 2013, 2 pages.
Author Unknown, "Lipid of the Month: May 2009, D6-7,10,13-Hexadecatrienoic Acid," retrieved from www.lipidox.se/text1_28.html, 2 pages.
Author Unknown, "Mixed Cultivation of Euglena Gracilis and Chlorella Sorokiniana: A Production Method of Algae Biomass on a Large Scale," Journal of Applied Biosciences 35, 2010, pp. 2225-2234.
Author Unknown, "The Micro Matic Difference," downloaded from http://www.micromatic.com/closed-chemical-systems/the-micromatic-difference-cid-953 on Apr. 12, 2013, 2 pages.
Azma et al., "Improved Protocol for the Preparation of Tetraselmis Suecica Axenic Culture and Adaptation to Heterotrophic Cultivation," The Open Biotechnology Journal, 2010, vol. 4, pp. 36-46.
Azma et al., "Improvement of Medium Composition for Heterotrophic Cultivation of Green Microalgae, *Tetraselmis suecica*, Using Response Surface Methodology," Biochemical Engineering Journal, 53, 2011, pp. 187-195.
Baird et al., "On Relating Physical Limits to the Carbon: Nitrogen Ratio of Unicellular Algae and Benthic Plants," Journal of Marine Systems, 49, 2004, pp. 169-175.
Balcázar, et al., "The Role of Probiotics in Aquaculture," Veterinary Microbiology, 114, 2006, pp. 173-186.
Bao, et al., "In situ Carbon Supplementation in Large-Scale cultivations of Spirulina platensis in Open Raceway Pond," Biotechnology and Bioprocess Engineering 17; 93-99 2012.
Barbera et al., "Significance Tests in the Study of the Specific Growth Rate of Haematococcus lacustris: Influence of Carbon Source and Light Intensity," Journal of Fermentation and Bioengineering, 1993, vol. 76, No. 5, pp. 403-405.

Bassleer Biofish, "Dr. Bassleers Biofish Food Chlorella—Strengthen the Immune System and Prevent Fish Diseases," retrieved from www.aquarium-munster.com, 1 page.
Becker, et al., "Transport Activity of MCT1 Expressed in Xenopus Oocytes Is Increased by Interaction with Carbonic Anhydrase," The Journal of Biological Chemistry, No. 280, No. 48, pp. 39882-39889, Dec. 2005.
Becker et al., "Crystallization of Phycoerythrin 545 of Rhodomonas Lens Using Detergents and Unusual Additives," Protein Science, 1998, 7, pp. 580-586.
Bell, "Experimental Evolution of Heterotrophy in a Green Alga," Evolution, 2012, 67-2, pp. 468-476.
Bell, "Experimental Sexual Selection in Chlamydomonas," J. Evol. Biol., 18, 2005, pp. 722-734.
Bell et al., "Experimental Evolution of Chlamydomonas II. Genetic Variation in Strongly Contrasted Environments," Heredity, 78, 1997, pp. 498-506.
Bennett et al., "Complementary Chromatic Adaptation in a Filamentous Blue-Green Alga," The Journal of Cell Biology, vol. 58, 1973, pp. 419-435.
Benitez-Santana, et al., "Dietary n-3 HUFA Deficiency Induces a Reduced Visual Response in Gilthead Seabream Sparus aurata Larvae," Aquaculture 264, 2007, pp. 408-417.
Berlin et al., "Inhibition of Cellulase, Xylanase and -glucosidase Activities by Softwood Lignin Preparations," Journal of Biotechnology, 125, 2006, pp. 198-209.
Bhatnagar et al., "Renewable Biomass Production by Mixotrophic Algae in the Presence of Various Carbon Sources and Wastewaters," Applied Energy, 88, 2011, pp. 3425-3431.
Bhosale, et al., "Purification and Characterization of Putative Alkaline [Ni—Fe] Hydrogenase from Unicellular Marine Green Alga, Tetraselmis kochinesis NCIM 1605," Microbiological Research, 164, 2009, pp. 131-137.
Biran et al., "Control of Methionine Biosynthesis in *Escherichia coli* by Proteolysis," Molecular Microbiology, 2000, 37, 6, pp. 1436-1443.
Blifernez-Klassen et al., "Cellulose Degradation and Assimilation by the Unicellular Phototrophic Eukaryote Chlamydomonas reinhardtii," Nature Communications, Nov. 2012, DOI: 10.1038/ncomms2210, 9 pages.
Blum, et al., "Novel Laboratory approaches to multi-purpse aquatic bioregenerative closed-loop food production systems," Acta Astronautica 1998 vol. 42 Nos. 1-8 pp. 25-35.
Borges, et al., "Fast microwave assisted pyrolysis of biomass using microwave absorbent," Bioresource Technology 2014 156 267-274.
Borowitzka et al., "Culture of the Astaxanthin-Producing Green Alga *Haematococcus pluvialis*, 1. Effects of Nutrients on Growth and Cell Type," Journal of Applied Phycology, 3, 1991, pp. 295-304.
Bouarab et al., "Heterotrophic and Mixotrophic Growth of Micractinium Pussillum Fresenius in the Presence of Acetate and Glucose: Effect of Light and Acetate Gradient Concentration," Water Research, 38, 2004, pp. 2706-2712.
Boyd et al., "Use of Probiotics for Improving Soil and Water Quality in Aquaculture Ponds," Department of Fisheries and Allied Aquacultures, Auburn University, Alabama, 1984, pp. 101-106, retrieved from nani.com/vn/VANBAN/01.pdf.
Boyle et al., "Flux Balance Analysis of Primary Metabolism in Chlamydomonas Reinhardtii," BMC Systems Biology, Jan. 2009, 3, 4, 14 pages.
Brennan et al., "Biofuels from Microalgae—A Review of Technologies for Production, Processing, and Extractions of Biofuels and Co-products," Renewable and Sustainable Energy Reviews, 14, 2010, pp. 557-577.
Brown et al., "Inorganic Nitrogen Assimilation in Aquatic Microorganisms," Advances in Aquatic Microbiology, 1977, vol. 1, pp. 49-114, 67 pages.
Brown et al., "Physiological Aspects of Microbial Inorganic Nitrogen Metabolism," Adv. In Microbial Physiology, vol. 11, 1970, 52 pages.
Brown et al., "The Biosynthesis of the Chromophore of Phycocyanin, Pathway of Reduction of Biliverdin to Phycocyanobilin," Biochem. J., 1989, vol. 261, pp. 259-263.

(56) References Cited

OTHER PUBLICATIONS

Brul et al., "Preservative Agents in Foods, Mode of Action and Microbial Resistance Mechanisms," International Journal of Food Microbiology, 50, 1999, pp. 1-17.
Bumbak, et al., "Best Practices in Heterotrophic High-Cell-Density Microalgal Processes: Achievements, Potential and Possible Limitations," Appl. Microbiol. Biotechnol., 2011, 91, pp. 31-46.
Burgie et al., "Structural Architecture of Galdieria Sulphuraria DCN1 L," Proteins, Apr. 2011, 79(4), pp. 1329-1336, 12 pages.
Burkholder, et al., "Mixotrophy, a Major Mode of Nutrition for Harmful Algal Species in Eutrophic Waters," Harmful Algae, 8, 2008, pp. 77-93.
Burlew, "Algal Culture from Laboratory to Pilot Plant," Carnegie Institution of Washington Publication 600, Jul. 1953, ISBN 0-87279-611-6, 369 pages.
Callely et al., "The Metabolism of Acetate in the Colourless Alga, Prototheca Zopfi," Biochem. J., 1964, vol. 90, p. 483-489.
Campbell, "Soil Stabilization by a Prokaryotic Desert Crust: Implications for Precambrian Land Biota," Orig. Life, Sep. 1979, 9, 4, pp. 335-348.
Capelli et al., "The Medical Research of Astaxanthin," 2010, retrieved from www.cyanotech.com/pdfs/bioastin/AstaxanthinAbstractBook2013.pdf, 273 pages.
Caron et al., "Technique for Enumeration of Heterotrophic and Phototrophic Nanoplankton, Using Epifluorescence Microscopy, and Comparison with Other Procedures," Applied and Environmental Microbiology, Aug. 1983, vol. 46, No. 2, pp. 491-498.
Casal, et al., "Mechanisms Regulating the Transport of Acetic Acid in *Saccharomyces cerevisiae*," Microbiology, 1996, 142, pp. 1385-1390.
Casal et al., "Enhanced Productivity of a Lutein-Enriched Novel Acidophile Microalga Grown on Urea," Marine Drugs, 2011, 9, pp. 29-42.
Castro-Puyana et al., "Extraction of New Bioactives from Neochloris Oleoabundans Using Pressurized Technologies and Food Grade Solvents," III Iberoamerican Conference on Supercritical Fluids, Cartagena de Indias (Columbia), 2013, 7 pages.
Cellexus Inc., "CellexusBag," retrieved from http://www.cellexusinc.com/pages/content/index.asp?PageID=115 on Nov. 2, 2012, 1 page.
Cellexus Inc., "CellMaker FERMENTER," retrieved from http://www.cellexusinc.com/pages/content/index.asp?PageID=118 on Nov. 2, 2012, 3 pages.
CellMakerPlus, "High Quality Single-Use, Disposable Bioreactor System—Simplifies Cell Culture and Fermentation Processes and Reduces Protein Production Times," retrieved from www.cellexusinc.com on Oct. 18, 2013, 3 pages.
Chacón-Lee, et al., "Microalgae for "Healthy" Foods—Possibilities and Challenges," Comprehensive Reviews in Food Science and Food Safety, 2010, vol. 9, pp. 655-675.
Chaiklahan et al., "Separation and Purification of Phycocyanin from *Spirulina* sp. Using a Membrane Process," Bioresource Technology, 102, 2011, pp. 7159-7164.
Chaiklahan et al., "Stability of Phycocyanin Extracted from *Spirulina* sp.: Influence of Temperature, pH and Preservatives," Process Biochemistry, 47, 2012, pp. 659-664.
Chang et al., "Use of Sulfite and Hydrogen Peroxide to Control Bacterial Contamination in Ethanol Fermentation," Applied and Environmental Microbiology, Jan. 1997, vol. 63, No. 1, pp. 1-6.
Cheirsilp et al., "Enhanced Growth and Lipid Production of Microalgae Under Mixotrophic Culture Condition: Effect of Light Intensity, Glucose Concentration and Fed-Batch Cultivation," Bioresource Technology, 110, 2012, pp. 510-516.
Chen et al., 'Cultivation, Photobioreactor Design and Harvesting of Microalgae for Biodiesel Production: A Critical Review,' Biresource Technology, 102, 2011, pp. 71-81.
Chen et al., "A Strategy for High Cell Density Culture of Heterotrophic Microalgae with Inhibitory Substrates," Journal of Applied Phycology, 7, 1995, pp. 43-46.

Chen et al., "Accumulation of Selenium in Mixotrophic Culture of Spirulina Platensis on Glucose," Bioresource Technology, 97, 2006, pp. 2260-2265.
Chen et al., "Fuel Properties of Microalgae (*Chlorella protothecoides*) Oil Biodiesel and its Blends with Petroleum Diesel," Fuel xxx, Nov. 2011, xxx-xxx, 4 pages.
Chen et al., "Heterotrophic Growth of Chlamydomonas Reinhardtii on Acetate in Chemostat Culture," Process Biochemistry, vol. 31, No. 6, 1996, pp. 601-604.
Chen et al., "High Cell Density Mixotrophic Culture of Spirulina Platensis on Glucose for Phycocyanin Production Using a Fed-Batch System," Enzyme and Microbial Technology, 20, 1997, pp. 221-224.
Chen et al., "Lumostatic Strategy for Microalgae Cultivation Utilizing Image Analysis and Chlorophyll a Content as Design Parameters," Bioresource Technology, 102, 2011, pp. 6005-6012.
Chen et al., "Mixotrophic and Heterotrophic Growth of Haematococcus Lacustris and Rheological Behaviour of the Cell Suspensions," Bioresource Technology, 62, 1997, pp. 19-24.
Chen et al., "Mixotrophic Culture of High Selenium-Enriched Spirulina Platensis on Acetate and the Enhanced Production of Photosynthetic Pigments," Enzyme and Microbial Technology, 39, 2006, pp. 103-107.
Chen et al., "Picochlorum as an Alternative to Nannochloropsis for Grouper Larval Rearing," Aquaculture, 338-341, 2012, pp. 82-88.
Cheng, Dispersed Ozone Flotation of Chlorella Vulgaris, Bioresource Technology, 101, 2010, pp. 9092-9096.
Cheng, et al., "Dispersed ozone flotation of Chlorella Vulgaris," Bioresource Technology 101 (2010) 9092-9096.
Chiang et al., "Allelochemicals of Botryococcus Braunii (Chlorophyceae)," J. Phycol., 40, 2004, pp. 474-480.
Chisti, Y. "Biodiesel from Microalgae," Biotechnology Advances 25, 2007, pp. 294-306.
Choi et al., "Enhancement of the Growth of Marine Microalga *Chlorella* sp. from Mixotrophic Perfusion Cultivation for Biodiesel Production," Chem. Biochem. Eng. Q., 26 (3), 2012, pp. 207-216.
Chojnacka et al., "Evaluation of *Spirulina* sp. Growth in Photoautotrophic, Heterotrophic and Mixotrophic Cultures," Enzyme and Microbial Technology, 34, 2004, pp. 461-465.
Chojnacka et al., "Kinetic and Stoichiometric Relationships of the Energy and Carbon Metabolism in the Culture of Microalgae," Biotechnology, 3 (1), 2004, pp. 21-34.
Chuanyin et al., "The Mixotrophic Growth of ANABAENA SP. HB1017," Acta Hydrobiologica Sinica, 1996, 20, 2, pp. 134-137, Abstract Only, 2 pages.
Cifuentes, et al., "Optimization of Biomass, Total Carotenoids and Astaxanthin Production in Haematococcus Pluvialis Flotow Strain Steptoe (Nevada, USA) Under Laboratory Conditions," Biol Res, 36, 2003, pp. 343-357.
Ciniglia et al., "Hidden Biodiversity of the Extremophilic Cyanidiales Red Algae," Molecular Ecology, 2004, 13, pp. 1827-1838.
Clark et al., "The Influence of Culture Medium and Light Cycle on the Productivity of the Green Algae *Neochloris oleoabundans*," Utah State University, Undergraduate Research Paper 9, 2010, 1 page, retrieved from http://digitalcommons.esu.edu/undergrad_research/9.
Colla et al., "Production of Biomass and Nutraceutical Compounds by Spirulina Platensis Under Different Temperature and Nitrogen Regimes," Bioresource Technology, 98, 2007, pp. 1489-1493.
Converti et al., "Effect of Temperature and Nitrogen Concentration on the Growth and Lipid Content of Nannochloropsis Oculata and Chlorella Vulgaris for Biodiesel Production," Chemical Engineering and Processing, 48, 2009, pp. 1146-1151.
Cook et al., "Chapter 7. Fatty Acid Desaturation and Chain Elongation in Eukaryotes," Biochemistry of Lipids, Lipoproteins and Membranes, Fourth Edition, 2002, pp. 181-204.
Cook et al., "Production and Evaluation of Alginate-chitosan Microcapsules as an Enteric Delivery Vehicle for Probiotic Bacteria," Biomacromolecules, 2011, 12, 7, 6 pages.
Cozzolino et al., "Molecular Variation in Galdieria Sulphuraria (Galdieri) Merola and its Bearing on Taxonomy," Hydrobiologia, 433, 2000, pp. 145-151.

(56) References Cited

OTHER PUBLICATIONS

Craig et al., "C-Phycocyanin and Allophycocyanin in Two Species of Blue-Green Algae," Biochem. J., 1968, 106, pp. 361-366.
Croft et al., "Algae Acquire Vitam B12 through a Symnbiotic Relationship with Bacteria," Nature Letters, Nov. 2005, vol. 438, 3, pp. 90-93.
Croft et al., "Minireviews: Algae Need Their Vitamins," Eukaryotic Cell, Aug. 2006, vol. 5, No. 8, pp. 1175-1183.
Cuaresma et al., "Luminostat Operation: A Tool to Maximize Microalgae Photosynthetic Efficiency in Photobioreactors During the Daily Light Cycle?," Bioresource Technology, 102, 2011, pp. 7871-7878.
Cuaresma et al., "Productivity and Selective Accumulation of Carotenoids of the Novel Extremophile Microalga *Chlamydomonas acidophila* Grown with Different Carbon Sources in Batch Systems," Journal of Microbiology and Biotechnology, 38, 2011, 35 pages.
Currie et al., "A Comparison of the Abilities of Freshwater Algae and Bacteria to Acquire and Retain Phosphorus," Limnol. Oceanogr., 29(2), 1984, pp. 298-310.
Daligault et al., "Mechanistic Characterization of _-3 Desaturation in the Green Alga *Chlorella vulgaris*," Phytochemistry 63, 2003, pp. 739-744.
Das et al., "Enhanced Algae Growth in Both Phototrophic and Mixotrophic Culture Under Blue Light," Bioresource Technology, 102, 2011, pp. 3883-3887.
Das et al., "Two Phase Microalgae Growth in the Open System for Enhanced Lipid Productivity," Renewable Energy, 36, 2011, pp. 2524-2528.
Dashtban et al., "Cellulase Activities in Biomass Conversion: Measurement Methods and Comparison," Critical Reviews in Biotechnology, 2010, pp. 1-8.
Dawson-Amoah, "Gas-Liquid Mass Transfer Rates by Gas Pumping: Agitators in Oxygen Pressure Leaching Systems," 1991, 7 pages, retrieved from https://circle.ubc.ca/handle/2429/29931 on Aug. 23, 2012.
Day, et al., "Development of an Industrial-Scale Process for the Heterotrophic Production of a Micro-Algal Mollusc Feed," Bioresource Technology 38 (1991) 245-249, 6 pages.
Dayan et al., "Rationale for a Natural Products Approach to Herbicide Discovery," Wiley Online Library, Jan. 2012, DOI 10.1002/ps. 2332, Pest Manag. Sci., 2012, 68, pp. 519-528, 10 pages.
De-Bashan et al., "Chlorella Sorokiniana UTEX 2805, a Heat and Intense, Sunlight-Tolerant Microalga with Potential for Removing Ammonium from Wastewater," Bioresource Technology, 99, 2008, pp. 4980-4989.
De-Bashan et al., "Cultivation Factors and Population Size Control the Uptake of Nitrogen by the Microalgae *Chlorella vulgaris* when Interacting with the Microalgae Growth-Promoting Bacterium Azospirillum Brasilense," FEMS Microbiology Ecology, 54, 2005, pp. 197-203.
De-Bashan et al., "Increased Pigment and Lipid Content, Lipid Variety, and Cell and Population Size of the Microalgae *Chlorella* spp. When Co-immobilized in Alginate Beads with the Microalgae-growth-promoting Bacterium Azospirillum brasilense," Can. J. Micro., 48, 2002, pp. 514-521.
De-Bashan et al., "Involvement of Indole-3-Acetic Acid Produced by the Growth-Promoting Bacterium *Azospirillum* SPP. in Promoting Growth of Chlorella Vulgaris," J. Phycol. 44, 2008, pp. 938-947.
De Castro et al., "Reverse Evolution: Driving Forces Behind the Loss of Acquired Photosynthetic Traits," PloS ONE, Dec. 2009, vol. 4, Issue 12, 6 pages.
Desbois et al., "A Fatty Acid from the Diatom Phaeodactylum Tricornutum is Antibacterial Against Diverse Bacteria Including Multi-Resistance *Staphylococcus aureus* (MRSA)," Mar Biotechnol., 2009, 11, pp. 45-52.
Dhar et al., 'Separation of Competitive Microorganisms Using Anaerobic Membrane Bioreactors as Pretreatment to Microbial Electrochemical Cells,' Bioresource Technology, Aug. 2013, 35 pags.

Djousse, et al., "Plasma Phospholipid Concentration of Cis-Palmitoeleic Acid and Risk of Heart Failure," Circ Heart Fail Nov. 2012 pp. 703-709.
Djousse, et al., "Red Blood Cell Membrane Concentration of cis-Palmitoleic and cis-Vaccenic Acids and Risk of Coronary Heart Disease," The American Journal of Cardiology Aug. 15, 2012 vol. 110(4) pp. 539-444.
Doan, et al., "Screening of Marine Microalgae for Biodiesel Feedstock," Biomass and Bioenergy, 35, 2011, pp. 2534-2544.
Doebbe et al., "Functional Integration of the HUP1 Hexose Symporter Gene into the Genome of C. Reinhardtii: Impacts on Biological H2 Production," Journal of Biotechnology, 131, 2007, pp. 27-33.
Doemel et al., "The Physiological Ecology of Cyanidium Caldarium," Journal of General Microbiology, 1971, 67, pp. 17-32.
Domergue et al., "New Insight into Phaeodactylum Tricornutum Fatty Acid Metabolism. Cloning and Functional Characterization of Plastidial and Microsomal 12-Fatty Acid Desaturases," Plant Physiology, Apr. 2003, vol. 131, pp. 1648-1660, 15 pages.
Doucha et al., 'Outdoor Open Thin-layer Microalgal Photobioreactor: Potential Productivity,' J. Appl. Phycol., 2009, 21, pp. 111-117.
Doucha et al., "Productivity, CO2/O2 Exchange and Hydraulics in Outdoor Open High Density Microalgal (*Chlorella* sp.) Photobioreactors Operated in a Middle and Southern European Climate," J. Appl. Phycol., 2006, 18, pp. 811-826.
Droop, "The Nutrient Status of Algal Cells in Continuous Culture," J. Mar. Biol. Ass. U.K., 1974, 54, pp. 825-855.
DSM, Corporate Communications, "Press Release: DSM Completes Acquisition of Martek; Adding New Nutrition Growth Platform," Health Nutrition Materials, Feb. 28, 2011, 3 pages.
Dutta et al., "Hydrogen Production by Cyanobacteria," Microbial Cell Factories, 4, 36, Dec. 2005, 11 pages.
Dvir et al., "Soluble Polysaccharide and Biomass of Red Microalga *Porphyridium* sp. Alter Intestinal Morphology and Reduce Serum Cholesterol in Rats," British Journal of Nutrition, 2000, 84, pp. 469-476.
Dykhuizen et al., "Selection in Chemostats," Microbiology Reviews, Jun. 1983, vol. 47, No. 2, pp. 150-168.
Dzanis, "Nutrition Through the Life Cycle: The Association of American Feed Control Officials Dog and Cat Food Nutrient Profiles: Substantiation of Nutritional Adequacy of Complete and Balanced Pet Foods in the United States," The Journal of Nutrition, downloaded from jn.nutrition.org on Jun. 6, 2013, 5 pages.
Díaz-Rosales et al., "Effects of Two Closely Related Probiotics on Respiratory Burst Activity of Senegalese Sole (Solea senegalensis, Kaup) Phagocytes, and Protection Against *Photobacterium damselae* subsp. piscicida," Aquaculture, 293, 2009, pp. 16-21.
El-Sayed et al., "Growth Response of Chlorella Vulgaris to Acetate Carbon and Nitrogen Forms," Nature and Science, 2011, 9, 9, pp. 53-58.
Emken, "Metabolism of Dietary Stearic Acid Relative to Other Fatty Acids in Human Subjects," The American Journal of Clinical Nutrition, 1994, 60 (suppl.), 1023S-1028S, downloaded from ajcn.nutrition.org on Oct. 5, 2012.
Engle et al., "Tilapia Farm Business Management and Economics: A Training Manual," Dec. 2005, Oregon State University, retrieved from pdacrsp.oregonstate.edu/pubs/engle_manual.pdf, 43 pages.
Epel et al., "Inhibition of Respiration in Prototheca Zopfi by Light," Plant Physiol., 1970, 45, pp. 728-734.
Ergün, et al., "Influence of Ulva Meal on Growth, Feed Utilization, and Body Composition of Juvenile Nile Tilapia (*Oreochromis niloticus*) at Two Levels of Dietary Lipid," Aquacult Int., 2009, 17, pp. 355-361.
Eriksen, "Production of Phycocyanin—a Pigment with Applications in Biology, Biotechnology, Foods and Medicine," Appl. Microbiol. Biotechnol., 2008, 80, 14 pages.
Eriksen, "The Technology of Microalgal Culturing," Biotechnol. Lett., 30, 2008, pp. 1525-1536.
Faheed et al., "Effect of Chlorella Vulgaris as Bio-fertilizer on Growth Parameters and Metabolic Aspects of Lettuce Plant," Journal of Agriculture & Social Sciences, vol. 4, No. 4, 2008, pp. 165-169.

(56) References Cited

OTHER PUBLICATIONS

Fan et al., "Sequential heterotrophy-dilution-photoinduction cultivation for efficient microalgal biomass and lipd production," Bioresource Technology 112 (2012) 206-211.

Fang, et al., 'Effects of Organic Carbon Sources on Cell Growth and Eicosapentaenoic Acid Conent of *Nannochloropsis* sp.,' Journal of Applied Phycology, 2004, 16, pp. 499-503.

Fang, et al., "Effect of Organic Carbon Sources on Growth and Photosynthesis of *Nannochloropsis* sp.," The Chinese Journal of Process Engineering, Jun. 2003, Abstract Only, 3 pages.

Feng et al., "Lipid Accumulation and Growth of Chlorella Zofingiensis in Flat Plate Photobioreactors Outdoors," Bioresource Technology, 102, 2011, pp. 10577-10584.

Fergola et al., "Allelopathy and Competition between Chlorella vulgaris and Pseudokirchneriella subcapitata: Experiments and Mathematical Model," Ecological Modelling, 208, 2007, pp. 205-214.

Fisher et al., "Fatty Acid Dynamics in Thalassiosira Pseudonana (Bacillariophyceae): Implications for Physiological Ecology," J. Phycol., 14(2), 1978, pp. 143-150.

Frada et al., "Quantum Requirements for Growth and Fatty Acid Biosynthesis in the Marine Diatom Phaeodactylum Tricornutum (Bacillariophyceae) in Nitrogen Replete and Limited Conditions," J. Phycol., 49, 2013, pp. 381-388.

Franklin et al., "Dietary Marine Algae (*Schizochytrium* sp.) Increases Concentrations of Conjugated Linoleic, Docosahexaenoic and Transvaccenic Acids in Milk of Dairy Cows," The Journal of Nutrition, pp. 2048-2054, downloaded from jn.nutrition.org on Jan. 14, 2013.

Fu et al., "Effects of Nutritions on Growth and Oil Accumulation of Phaeodactylum tricornutum," Hubei Agricultural Sciences, 2011, Abstract Only, 3 pages.

Fujii et al., Isolation of the Non-fastidious Microalga with Astaxanthin-accumulating Property and its Potential for Application to Aquaculture, Aquaculture, 261, 2006, pp. 285-293.

Fujii et al., "Potential Use of the Astaxanthin-Producing Microalga, *Monoraphidium* sp. GK12, as a Functional Aquafeed for Prawns," J. Appl. Phycol., 22, 2010, pp. 363-369.

Fukui et al., "Relationship Between Color Development and Protein Conformation in the Phycocyanin Molecule," Dyes and Pigments, 63, 2004, pp. 89-94.

Gaigalas et al., "Measurement of Absorption and Scattering with an Integrating Sphere Detector: Application to Microalgae," Journal of Research of the National Institute of Standards and Technology, vol. 114, No. 2, Mar.-Apr. 2009, pp. 69-81.

Galhano et al., "Changes in Fatty Acid Profile and Antioxidant Systems in a Nostoc muscorum Strain Exposed to the Herbicide Bentazon," Process Biochemistry, 46, 2011, pp. 2152-2162.

Gallardo et al., "Evaluation of Mucus, Navicula, and Mixed Diatoms as Larval Settlement Inducers for the Tropical Abalone Haliotis Asinina," Aquaculture, 221, 2003, pp. 357-364.

Gallon et al., "Nitrogen Fixation by *Oscillatoria* spp. Under Autotrophic and Photoheterotrophic Conditions," Journal of General Microbiology, 1991, 137, pp. 31-39.

Ganga et al., "Stress Response in Sea Bream (*Sparus aurata*) Held Under Crowded Conditions and Fed Diets Containing Linseed and/or Soybean Oil," Aquaculture, 311, 2011, pp. 215-223.

Ganuza, "Heterotrophic Cultivation of Microalgae as a Source of Docasahexaenoic Acid for Aquaculture," Thesis Submitted for the Degree of Doctor of Phylosophy in the University of Las Palmas de Gran Canaria, 2008, 149 pages.

Ganuza et al., "Crypthecodinium cohnii and *Schizochytrium* sp. as Potential Substitutes to Fisheries-derived Oils from Seabream (*Sparus aurata*) Microdiets," Aquaculture, 277, 2008, pp. 109-116.

Ganuza et al., "High-cell-density Cultivation of *Schizochytrium* sp. in an Ammonium/pH-auxostat fed-batch system," Biotechnol. Lett., Mar. 2008, 6 pages.

Ganuza et al., "Lipid Accumulation in Schizochytrium G13/2S Produced in Continuous Culture," Appl. Microbiol. Biotechnol., 2007, 76, pp. 985-990.

Garcia-Malea, et al., "Modelling of Growth and Accumulation of Carotenoids in Haematococcus Pluvialis as a Function of Irradiance and Nutrients Supply," Biochemical Engineering Journal 26, 2005, pp. 107-114.

Garcia-Malea et al., "Continuous Production of Green Cells of Haematococcus Pluvialis: Modeling of the Irradiance Effect," Enzyme and Microbial Technology, 38, 2006, pp. 981-989.

Garcia-Ochoa, et al., "Research Review Paper: Bioreactor Scale-Up and Oxygen Transfer Rate in Microbial Processes: An Overview," Biotechnology Advances, 27, 2009, pp. 153-176.

Garcia-Pichel, et al., "The Evoluation of a Capacity to Build Supra-Cellular Ropes Enabled Filamentous Cyanobacteria to Colonize Highly Erodible Substrates," PloS One, Nov. 2009, vol. 4, No. 11, 6 pages.

Garcia et al., "Mixotrophic Growth of Phaeodactylum Tricornutum on Glycerol: Growth Rate and Fatty Acid Profile," Journal of Applied Phycology, 12, 2000, pp. 239-248.

Garcia et al., "Mixotrophic Growth of the Microalga Phaeodactylum Tricornutum Influence of Different Nitrogen and Organic Carbon Sources on Productivity and Biomass Composition," Process Biochemistry, 40, 2005, pp. 297-305.

Garcia et al., "Mixotrophic Production of Marine Microalga *Phaeodactylum tricornutum* on Various Carbon Sources," Journal of Microbiology and Biotechnology, 2006, 16(5), pp. 689-694.

Gardan et al., "*Acidovorax anthurii* sp. nov., a New Phytopathogenic Bacterium which Causes Bacterial Leaf-spot of Anthurium," International Journal of Systematic and Evolutionary Microbiology, 2000, 50, pp. 235-246.

Garg, et al., "Macadamia Nut Consumption Lowers Plasma Total and LDL Cholesterol Levels in Hypercholesterolemic Men," The Journal of Nutrition, downloaded from jn.nutrition.org on Oct. 18, 2013, pp. 1060-1063.

Gatenby et al., "Biochemical Composition of Three Algal Species Proposed as Food for Captive Freshwater Mussels," Journal of Applied Phycology, 15, 2003, 11 pages.

Gatlin et al., "Expanding the Utilization of Sustainable Plant Products in Aquafeeds: A Review," Aquaculture Research, 2007, 38, pp. 551-579.

Gelagutashvili et al., "Interacion of Heavy Metal Ions with C-Phycocyanin: Binding Isotherms and Cooperative Effects," Medical Physics, Jul. 2009, 10 pages.

Ghazala et al., "Fatty Acids and Biological Activities of Crude Extracts of Freshwater Algae from Sindh," Pak. J. Bot., 42(2), 2010, pp. 1201-1212.

Giandomenico et al., "The Importance of Sodium Pyruvate in Assessing Damage Produced by Hydrogen Peroxide," Free Radical Biology & Medicine, 1997, vol. 23, No. 3, pp. 426-434.

Gladue et al., "Microalgal Feeds for Aquaculture," Journal of Applied Phycology, 6, 1994, pp. 131-141.

Goecke et al., "Algae as an Important Environment for Bacteria—Phylogenetic Relationships Among New Bacterial Species Isolated from Algae," Phycologia, Jan. 2013, vol. 52, No. 1, pp. 14-24.

Goksan et al., "An Alternative Approach to the Traditional Mixotrophic Cultures of Haematococcus Pluvialis Flotow (Chlorophyceae)," Journal of Microbiology and Biotechnology, 20, 9, 2010, pp. 1276-1282.

Gomez-Gil et al., "The Use and Selection of Probiotic Bacteria for Use in the Culture of Larval Aquatic Organisms," Aquaculture, 191, 2000, pp. 259-270.

Gonzalez et al., "Efficiency of Ammonia and Phosphorus Removal from a Colombian Agroindustrial Wastewater by the Microalgae *Chlorella vulgaris* and *Scenedesmus dimorphus*," Bioresource Technology, 60, 1997, pp. 259-262.

Gonzalez et al., "Increased Growth of the Microalga *Chlorella vulgaris* When Coimmobilized and Cocultured in Alginate Beads with the Plant-Growth-Promoting Bacterium *Azospirillum brasilense*," Applied and Environmental Microbiology, Apr. 2000, vol. 66, No. 4, pp. 1527-1531.

Goulding et al., "The Photo-Assimilation of Acetate by Pyrobotrys (Chlamydobotrys) Stellata," J. Gen. Microbiol., 1967, 48, pp. 127-136.

(56) References Cited

OTHER PUBLICATIONS

Gouveia et al., 'Chapter 2. Microalgae in Novel Food Products,' Food Chemistry Research Developments, IBSN 978-1-60456-262-0, 2008, 37 pages.
Gouveia et al., "Neochloris Oleabundans UTEX #1185: A Suitable Renewable Lipid Source for Biofuel Production," J. Ind. Microbiol. Biotechnol., 36, 2009, pp. 821-826.
Grande, et al., "The Medical Research of Spirulina," 2009, 441 pages, retrieved from http://www.cyanotech.com/pdfs/spirulina/Spirulina_Abstracts.pdf.
Graverholt et al., "Heterotrophic High-cell-density fed-batch and Continuous-flow Cultures of Galdieria Sulphuraria and Production of Phycocyanin," Appl. Microbiol. Biotechnol., 2007, 77, pp. 69-75.
Graziani et al., "Microalgae as Human Food: Chemical and Nutritional Characteristics of the Thermo-Acidophilic Microalga *Galdieria sulphuraria*," Food & Function, 4, 144, 2013, pp. 144-152, downloaded from http://pubs.rsc.org.
Green et al., "Role of Fatty Acid Elongases in Determination of de novo Synthesized Monounsaturated Fatty Acid Species," Journal of Lipid Research, vol. 51, 2010, pp. 1871-1877, downloaded from www.jlr.org on Sep. 19, 2012.
Gregory et al., "Algae-Produced Pfs25 Elicits Antibodies that Inhibit Malaria Transmission," PLoS One, May 2012, vol. 7, Issue 5, 10 pages.
Griel et al., "A Macadamia Nut-Rich Diet Reduces Total and LDL-Cholesterol in Mildly Hypercholesterolemic Men and Women," The Journal of Nutrition, Nutrition and Disease, 2008, downloaded from jn.nutrition.org on Oct. 18, 2013, 7 pages.
Griffiths et al., "Lipid Productivity as a Key Characteristic for Choosing Algal Species for Biodiesel Production," J. Appl. Phycol., 2009, 21, pp. 493-507.
Grima et al., 'Recovery of Microalgal Biomass and Metabolites: Process Options and Economics,' Biotechnology Advances 20, 2003, pp. 491-515.
Grobbelaar et al., "Physiological and Technological Considerations for Optimising Mass Algal Cultures," Journal of Applied Phycology, 12: 201-206, 2000.
Grobbelaar et al., "Respiration Losses in Planktonic Green Algae Cultivated in Raceway Ponds," Journal of Plankton Research, 1985, vol. 7, No. 4, pp. 497-506.
Gross et al., "Heterotrophic Growth of Two Strains of the Acido-Thermophilic Red Alga *Galdieria sulphuraria*," Plant Cell Physiol., 36, 4, 1995, pp. 633-638.
Gu, et al., "Effect of Salinity Change on Biomass and Biochemical Composition of Nannochloropsis oculata," Journal of the World Aquaculture Society, Feb. 2012, vol. 43, No. 1, pp. 97-106.
Guan et al., "Gasification of Alga *Nannochloropsis* sp. in Supercritical Water," J. of Supercritical Fluids, 61, 2012, pp. 139-145.
Guardian, "Pressure-Dispense Liner," 2011, 1 page, retrieved from www.graylingindustries.com on Oct. 23, 2013.
Guerrini et al., "Bacterial-algal Interactions in Polysaccharide Production," Aquatic Microbial Ecology, Aug. 1998, vol. 15, pp. 247-253.
Gupta et al., "Omega-3 Biotechnology: Thraustochytrids as a Novel Source of Omega-3 Oils," Biotechnology Advances, 30, 2012, pp. 1733-1745.
Guroy et al., "Effect of Dietary Ulva and Spirulina on Weight Loss and Body Composition of Rainbow Trout, *Oncorhynchus mykiss* (Walbaum), During a Starvation Period," Journal of Animal Physiology and Animal Nutrition, 95, 2011, pp. 320-327.
Gushina et al., "Lipids and Lipid Metabolism in Eukaryotic Algae," Progress in Lipid Research, 45, 2006, pp. 160-186.
Götz et al., 'The Very-Long-Chain Fatty Acid Synthase Is Inhibited by Chloroacetamides,' Z. Naturforsch., 59c, 2004, pp. 549-553.
Haass, et al., "Regulation of Hexose Transport in Chlorella Vulgaris: Characteristics of Induction and Turnover," Plant Physiol., 1974, 53, pp. 14-20.
Hallmann et al., "The Chlorella Hexose/H+ Symporter is a Useful Selectable Marker and Biochemical Reagent when Expressed in Volvox," Proc. Natl. Acad. Sci., vol. 93, Jan. 1996, pp. 669-673.
Hamilton, "Fatty Acid Transport: Difficult or Easy?," Journal of Lipid Research, 1998, vol. 39, pp. 467-481, downloaded from www.jlr.org on Feb. 12, 2013.
Hammer, et al., "The Role of Mixotrophy in Plankton Bloom Dynamics, and the Consequences for Productivity," ICES Journal of Marine Science, 62, 2005, pp. 833-840.
Haque et al., "Propionic Acid is an Alternative to Antibiotics in Poultry Diet," Bang. J. Anim. Sci., 2009, 38, (1&2), pp. 115-122.
Harker et al., "Factors Responsible for Astaxanthin Formation in the Chlorophyte Haematococcus Pluvialis," Bioresource Technology, 55, 1996, pp. 207-214.
Harper Kimball et al, 'Cyanobacteria and cyanolichens: Can they enhance availability of essential minerals for higher plants?' Great Basin Naturalist, vol. 53, No. 1, 1993, pp. 59-72.
Harris, et al., Zooplankton Grazing on the Coccolithophore Emiliania Huxleyi and its Role in Inorganic Carbon Flux, Marine Biology, 1994, 119, pp. 431-439.
Harris et al., "Skin Microbes on Frogs Prevent Morbidity and Mortality Caused by a Lethal Skin Fungas," The ISME Journal, 2009, 7 pages.
Harris et al., "The Fatty Acid Metabolism of Chlorella Vulgaris," Biochimica Biophysica Acta, 106, 1965, pp. 465-473.
Hartmann et al., "Assessing Amino Acid Uptake by Phototrophic Nanoflagellates in Nonaenic Cultures Using Flow Cytometric Sorting," FEMS Microbiol Lett., 298, 2009, pp. 166-173.
Hata et al., "Characterization of Energy Conversion Based on Metabolic Flux Analysis in Mixotrophic Liverwort Cells, *Marchantia polymorpha*," Biochemical Engineering Journal 6, 2000, pp. 65-74.
Hata et al., "Production of Astaxanthin by Haematococcus Pluvialis in a Sequential Heterotrophic-Photoautotrophic Culture," Journal of Applied Phycology, 13, 2001, pp. 395-402.
Heifetz et al., "Effects of Acetate on Facultative Autotrophy in Chlamydomonas Reinhardtii Assessed by Photosynthetic Measurements and Stable Isotope Analyses," Plant Physiology, Apr. 2000, vol. 122, pp. 1439-1445.
Hempel, et al., "Microalgae as bioreactors for bioplastic production," Microbial Cell Factories 2011 10:81 6 pgs.
Henry et al., 'Section 22. Alternative Separation Processes,' Perrys Chemical Handbook, Distillation, Catalyst, Chemistry, Eighth Edition, , Dec. 2011, pp. 22-1-22-77.
Herdman et al., "A New Medium for the Isolation and Growth of Auxotrophic Mutants of the Blue-green Alga *Anacystis nidulans*," Journal of General Microbiology, 1973, 79, pp. 233-237.
Heredia-Arroyo et al., "Mixotrophic Cultivation of Chlorella Vulgaris and its Potential Application for the Oil Accumulation from Non-Sugar Materials," Biomass and Bioenergy, 35, 2011, pp. 2245-2253.
Higa et al., "Beneficial and Effective Microorganisms for a Sustainable Agriculture and Environment," International Nature Farming Research Center, Atami, Japan, 1994, retrieved from Bokashicenter.com, 16 pages.
Highley, "Inhibition of Cellulases of Wood-Decay Fungi," vol. 247 of the U.S.D.A. Forest Service research paper, Dept. of Agriculture, Forest Service, Forest Products Laboratory, 1975, 10 pages.
Hii et al., "Interactive Effect of Ammonia and Nitrate on the Nitrogen Uptake by *Nannochloropsis* sp.," Journal of Sustainability Science and Management, Jun. 2011, vol. 6, No. 1, pp. 60-68, ISSN: 1823-8556.
Hilditch et al., "C-Phycocyanin from the Cyanobacterium *Aphanothece halophytica*," Phytochemistry, vol. 30, No. 11, 1991, pp. 3515-3517.
Hilgarth et al., "Glucose Increases the Expression of the ATP/ADP Translocator and the Glyceraldehyde-3-phosphate Dehydrogenase Genes in Chlorella," The Journal of Biological Chemistry, vol. 266, No. 35, Dec. 15, 1991, pp. 24044-24047.
Hillen, et al., "Hydrocracking of the Oils of Botryococcus braunii to Transport Fuels," Biotechnology and Bioengineering 1982 vol. 24 pp. 193-205.
Hines et al., "Simple Strategies to Improve Bioprocess Pure Culture Processing," Pharmaceutical Engineering, May/Jun. 2010, vol. 30, No. 3, 6 pages.
Hiramatsu et al., "Expression of a Chitinase Gene and Lysis of the Host Cell Wall during Chlorella Virus CVK2 Infection," Virology, 260, 1999, pp. 308-315.

(56) References Cited

OTHER PUBLICATIONS

Hoare et al., "The Photoassimilation of Organic Compounds by Autotrophic Blue-Green Algae," J. Gen. Microbiol., 1967, 49, pp. 351-370.
Hodgson et al., "A Direct Pathway for the Conversion of Propionate into Pyruvate in Moraxella Iwoffi," Biochem. J., 1968, 107, pp. 7-18.
Hodson et al., "Metabolism of Urea by Chlorella Vulgaris," Plant Physiol., 1969, 44, pp. 691-696.
Hoffman et al., "Structural Basis of Light Harvesting by Carotenoids: Peridinin-Chlorophyll-Protein from Amphidinium Carterae," Science, vol. 272, Jun. 1996, pp. 1788-1791.
Hongyang et al., "Cultivation of Chlorella Pyrenoidosa in Soybean Processing Wastewater," Bioresource Technology, 102, 2011, pp. 9884-9890.
Hsieh et al., 'A Novel Photobioreactor with Transparent Rectangular Chambers for Cultivation of Microalgae,' Biochemical Engineering Journal, 46, 2009, pp. 300-305.
Hsieh et al., "Cultivation of Microalgae for Oil Production with a Cultivation Strategy of Urea Limitation," Bioresource Technology, 100, 2009, pp. 3921-3926.
Hsu et al., "Flow Cytometry of Chlorella After Dehydration Stress," Plant Science, 134, 1998, pp. 163-169.
Hu, et al., "Construction of closed integrative system for gases robust stabilization employing microalgae peculiarity and computer experiment," Ecological Engineering 44 (2012) 78-87.
Hu et al., 'Optimization of Growth and Fatty Acid Composition of a Unicellular Marine Picoplankton, *Nannochloropsis* sp., with Enriched Carbon Sources,' Biotechnology Letters, 25, 2003, pp. 421-425.
Hu et al., Use of Surface Aerator to Improve Oxygen Transfer in Cell Culture, Biotechnology and Bioengineering, vol. XXVIII, 1986, pp. 122-125.
Huang et al., "+UVA Treatment Increases the Degree of Unsaturation in Microalgal Fatty Acids and Total Carotenoid Content in Nitzschia Closterium (Bacillariophyceae) and Isochrysis Zhangjiangensis (Chrysophyceae)," Food Chemistry, 129, 2011, pp. 783-791.
Huang et al., "Effects of Organic Carbon Compounds on the Growth of Isochrysis zhanjiangensis," Ecologic Science, 2007, Abstract Only, 4 pages.
Huang et al., "Short- and Medium-chain Fatty Acids Exhibit Antimicrobial Activity for Oral Microorganisms," Archives of Oral Biology, 56, 2011, pp. 650-654.
Huerlimann et al., "Growth, Lipid Content, Productivity, and Fatty Acid Composition of Tropical Microalgae for Scale-Up Production," Biotechnology and Bioengineering, vol. 107, No. 2, Oct. 2010, pp. 245-257.
Huo et al., "Cultivation of Chlorella Zofingiensis in Bench-Scale Outdoor Ponds by Regulation of pH Using Dairy Wastewater in Winter, South China," Bioresource Technology, 121, 2012, pp. 76-82.
Ingram et al., "Role of Reduced Exogenous Organic Compounds in the Physiology of the Blue-Green Bacteria (Algae): Photoheterotrophic Growth of a "Heterotrophic" Blue-Green Bacterium," Journal of Bacteriology, May 1973, vol. 114, No. 2, pp. 695-700.
Ingram et al., "Role of Reduced Exogenous Organic Compounds in the Physiology of the Blue-Green Bacteria (Algae): Photoheterotrophic Growth of an "Autotrophic" Blue-Green Bacterium," Journal of Bacteriology, May 1973, vol. 114, No. 2, pp. 701-705.
International Search Report and Written Opinion of the International Search Authority, the European Patent Office, for International Application No. PCT/US2013/069037, dated Feb. 17, 2014, 10 pages.
International Search Report and Written Opinion of the International Search Authority, the European Patent Office, for the International Application No. PCT/US2013/069040, dated Feb. 5, 2014, 10 pages.
International Search Report and Written Opinion of the International Search Authority, the European Patent Office, for the International Application No. PCT/US2013/069042, dated Feb. 11, 2014, 15 pages.
Ip, et al., "Enhanced Production of Astaxanthin by the Green Microalga *Chlorella zofingiensis* in Mixotrophic Culture," Process Biochemistry, 39, 2004, pp. 1761-1766.
Ip et al., "Employment of Reactive Oxygen Species to Enhance Astaxanthin Formation in Chlorella Zofingiensis in Heterotrophic Culture," Process Biochemistry, 40, 2005, pp. 3491-3496.
Ip et al., "Peroxynitrite and Nitryl Chloride Enhance Astaxanthin Production by the Green Microalga *Chlorella zofingiensis* in Heterotrophic Culture," Process Biochemistry, 40, 2005, pp. 3595-3599.
Ip et al., "Production of Astaxanthin by the Green Microalga *Chlorella zofingiensis* in the Dark," Process Biochemistry, 40, 2005, pp. 733-738.
Jaisamut et al., "Cellulolytic Enzymes—Activity Comparison and Effect of Potential Inhibitors," Institute of Chemical Technology Prague, Faculty of Food and Biochemical Technology, Department of Fermentation Technology and Bioengineering, Odpadove Forum 2011, 11 pages.
Jakobsson et al., "Fatty Acid Elongases in Mammals: Their Regulation and Roles in Metabolism," Progress in Lipid Research, 45, 2006, pp. 237-249.
Jeon, et al., "Combined Effects of Light Intensity and Acetate Concentration on the Growth of Unicellular Microalga *Haematococcus pluvialis*," Enzyme and Microbial Technology, 39, 2006, pp. 490-495.
Jiang et al., "Effects of Medium Glucose Concentration and pH on Docosahexaenoic Acid Content of Heterotrophic Crypthecodinium Cohnii," Process Biochemistry, 35, 2000, pp. 1205-1209.
Jihong et al., "Growth Characteristics of *Tetraselmis* sp.—1 in Phototrophic, Mixotrophic and Heterotrophic Conditions," High Technology Letters, vol. 10, No. 2, Jun. 2004, pp. 83-86.
Johnson, "OSHA Infectious Dose White Paper," Applied Biosafety, 8(4), 2003, pp. 160-165.
Jones et al., "Enhancement in the Blue-Green Alga, Anacystis Nidulans," Plant Physiology, Nov. 1964, 39, pp. 938-946.
Jørgensen et al., "Separation and Quantification of Cellulases and Hemicellulases by Capillary Electrophoresis," Analytical Biochemistry, 317, 2003, pp. 85-93.
Kalavathi et al., 'Degradation and Metabolization of the Pigment—Melanoidin in Distillery Effluent by the Marine Cyanobacterium Oscillatoria boryana BDU 92181,' Enzyme and Microbial Technology, 29, 2001, pp. 246-251.
Kalita et al., "Ankistrodesmus Falcatus: A Promising Candidate for Lipid Production, its Biochemical Analysis and Strategies to Enhance Lipid Productivity," Journal of Microbiology and Biotechnology Research, 2011, 1, 4, pp. 148-157.
Kamjunke et al., "Utilisation of Leucine by Several Phytoplankton Species," Limnologica, 38, 2008, pp. 360-366.
Kantarci et al., "Bubble Column Reactors," Process Biochemistry, 40, 2005, pp. 2263-2283.
Karlander et al., "Responses of Heterotrophic Cultures of Chlorella Vulgaris Beyerinck to Darkness and Light. II. Action Spectrum for and Mechanism of the Light Requirement for Heterotrophic Growth," Plant Physiol., 1966, 41, pp. 7-14.
Kasemets et al., "Modification of A-stat for the Characterization of Microorganisms," Journal of Microbiological Methods, 55, 2003, pp. 187-200.
Katano et al., 'Discrimination of Two Phycoerythrin-Pigment Types of Synechococcus and Their Seasonal Succession in the Uwa Sea,' Microbes Environ., vol. 19, No. 1, 004, pp. 7-12.
Katsuda et al., "Astaxanthin Production by Haematococcus Pluvialis under Illumuniation with LEDs," Enzyme and Microbial Technology 35, 2004, pp. 81-86.
Katsuda et al., "Effect of Flashing Light from Blue Light Emitting Diodes on Cell Growth and Astaxanthin Production of Haematococcus Pluvialis," Journal of Bioscience and Bioengineering, vol. 102, No. 5, 2006, pp. 442-446.
Katsuda et al., "Effect of Light Intensity and Frequency of Flashing Light from Blue Light Emitting Diodes on Astaxanthin Production by Haematococcus Pluvialis," Journal of Bioscience and Bioengineering, vol. 105, No. 3, 2008, pp. 216-220.
Kawaguchi et al., "New Method for Isolating Antibiotic-producing Fungi," The Journal of Antibiotics, 2013, 66, pp. 17-21.

(56) References Cited

OTHER PUBLICATIONS

Kaya et al., "Thraustochytrid aurantiochytrium sp. 18W-13a Accumulates High Amounts of Squalene," Biosci. Biotechnol. Biochem., 75, 11, 2011, pp. 2246-2248.
Kazamia et al., "Synthetic Ecology—A Way Forward for Sustainable Algal Biofuel Production?," Journal of Biotechnology xxx, 2012, xxx-xxx, 7 pages.
Khadke et al., "The Physiology of Neospongiococcum Ovatum Deason," New Phytol., 1976, 77, pp. 635-639.
Khoeyi et al., "Effect of Light Intensity and Photoperiod on Biomass and Fatty Acid Composition of the Microalgae, Chlorella vulgaris," Aquacult Int., 2012, 20, pp. 41-49.
Killam et al., "A Special Effect of Light on the Growth of Chlorella Vulgaris," American Journal of Botany, Oct. 1956, vol. 43, No. 8, pp. 569-572.
Kim et al., "Alga-lytic Activity of Pseudomonas fluorescens Against the Red Tide Causing Marine Alga Heterosigma akoshiwo (Raphidophyceae)," Biological Control, 41, 2007, pp. 296-303.
Kim et al., "Enhanced Production of Astaxanthin by Flashing Light Using Haematococcus Pluvialis," Enzyme and Microbial Technology, 39, 2006, pp. 414-419.
Kim et al., "Optimization of Culture Conditions and Comparison of Biomass Productivity of Three Green Algae," Bioprocess and Biosystems Engineering, vol. 35, Nos. 1-2, 2012, pp. 19-27.
Kitano et al., "Changes in Eicosapentaenoic Acid Content of Navicula saprophila, Rhodomonas salina and Nitzschia sp. Under Mixotrophic Conditions," Journal of Applied Phycology, 9, 1997, pp. 559-563.
Kitano et al., "Enhanced Eicosapentaenoic Acid Production by Navicula Saprophila," Journal of Applied Phycology, 10, 1998, pp. 101-105.
Kitozyme SA, "Chitosan Gras Notice," Jul. 28, 2011, 105 pages.
Knothe, "A Technical Evaluation of Biodiesel from Vegetable Oils vs. Algae. Will Algae-derived Biodiesel Perform?," Green Chem., 2011, 13, pp. 3048-3065.
Kobayashi et al., "Antioxidant Role of Astaxanthin in the Green Alga Haematococcus pluvialis," Appl. Microbiol. Biotechnol., 1997, 48, pp. 351-356.
Kobayashi et al., "Growth and Astaxanthin Formation of Haematococcus Pluvialis in Heterotrophic and Mixotrophic Conditions," Journal of Fermentation and Bioengineering, vol. 74, No. 1, 1992, pp. 17-20.
Koller, et al., "Characterisitics and potential of micro algal cultivation strategies: a review," J. of Cleaner Production 37 (2012) 377-388.
Kommareddy, A. et al., 'Study of Light as a parameter in the growth of algae in a Photo-Bio Reactor (PBR),' Written for presentation at the 2003 ASAE Annual International Meeting Sponsoted by ASAE, Riviera Hotel and Convention Center, Las Vegas, NV, USA, Jul. 27-30, 2003.
Komor et al., "The Determination of the Membrane Potential of Chlorella vulgaris, Evidence for Electrogenic Sugar Transport," Eur. J. Biochem., 70, 1976, pp. 197-204.
Komor et al., "The Hexose-Proton Symport System of Chlorella vulgaris, Specificity, Stoichiometry and Energetics of Sugar-Induced Proton Uptake," Eur. J. Biochem., 44, 1974, pp. 219-223.
Kong et al., "Effects of Glycerol and Glucose on the Enhancement of Biomass, Lipid and Soluble Carbohydrate Production by Chlorella Vulgaris in Mixotrophic Culture," Mar. 2012, 21 pages, retrieved from http://www.ftb.com.hr/19.Kong_et_al.pdf on Jun. 8, 2012.
Kong et al., "Enhancement of Biomass and Hydrocarbon Productivities of Botryococcus Braunii by Mixotrophic Cultivation and its Application in Brewery Wastewater Treatment," African Journal of Microbiology Research, vol. 6 (7), Feb. 2012, pp. 1489-1496.
Kong et al., "The Characteristics of Biomass Production, Lipid Accumulation and Chlorophyll Biosynthesis of Chlorella vulgaris Under Mixotrophic Cultivation," African Journal of Biotechnology, vol. 10(55), Sep. 2011, pp. 11620-11630.
Kotzabasis et al., "Methanol as Alternative Carbon Source for Quicker Efficient Production of the Microalgae Chlorella minutissima: Role of the Concentration and Frequence of Administration," Journal of Biotechnology, 70, 1999, pp. 357-362.
Kowallik, "Action Spectrum for an Enhancement of Endogenous Respiration by Light in Chlorella," Plant Physiol., 1967, 42, pp. 672-676.
Kureshy, et al., "Effect of Ozone Treatment on Cultures of Nannochloropsis oculata, Isochrysis galbana, and Chaetoceros gracilis," Journal of World Aquaculture Society 1999 vol. 30 No. 4, 8 pgs.
Kuske et al., "Response and Resilience of Soil Biocrust Bacterial Communities to Chronic Physical Disturbance in Arid Shrublands," The ISME Journal, 2012, 6, pp. 886-897.
Lababpour et al., "Effects of Nutrient Supply Methods and Illumination with Blue Light Emitting Diodes (LEDs) on Astaxanthin Production by Haematococcus Pluvialis," Journal of Bioscience and Bioengineering, vol. 98, No. 6, 2004, pp. 452-456.
Laing, "Cultivation of Marine, Unicellular Algae," Laboratory Leaflet No. 67, Ministry of Agriculture Fisheries and Food Directorate of Fisheries Research, Lowestoft, 67, 1991, 32 pages.
Lakaniemi et al., "Growth of Chlorella vulgaris and Associated Bacteria in Photobioreactors," Microbial Biotechnology, 2012, 5, 1, pp. 69-78.
Lam et al., "Microalgae Biofuels: A Critical Review of Issues, Problems and the Way Forward," Biotechnology Advances, 30, 2012, pp. 673-690.
Lambert et al. "Photoheterotrophic Growth of Agmenellum Quadruplicatum PR-6," Journal of Bacteriology, Feb. 1986, vol. 165, No. 2, pp. 654-656.
Laugier et al., "Ultrasound in Gas-Liquid Systems: Effects on Solubility and Mass Transfer," Ultrason Sonochem., Sep. 2008, 15(6), pp. 965-972, Abstract Only, 1 page, retrieved from http://www.ncbi.nlm.nih.gov/pubmed/18468473 on Aug. 23, 2012.
Lednicka et al., "Isolation and Identification of Cellulolytic Bacteria Involved in the Degradation of Natural Cellulosic Fibres," System. Appl. Microbiol., 23, 2000, pp. 292-299.
Lee, 'Microalgal Mass Culture Systems and Methods: Their Limitation and Potential,' Journal of Applied Phycology, 13, 2001, pp. 307-315.
Lee, "Chapter 2: Bioprocess Technology," Microbial Biotechnology—Principles and Applications, Second Edition, Aug. 2006, 49 pages.
Lee, et al., "Design and Performance of an a-type Tubular Photobioreactor for Mass Cultivation of Microalgae," Journal of Applied Phycology, 7, 1995, pp. 47-51.
Lee, et al., "Nitrogen Removal from Wastewaters by Microalgae Without Consuming Organic Carbon Sources," Journal of Microbiology and Bioetechnology, 2002, 12(6), pp. 979-985.
Lee, et al., "The Estimation of Algal Yield Parameters Associated with Mixotrophic and Photoheterotrophic Growth Under Batch Cultivation," Biomass 18, 1989, pp. 153-160.
Lee et al., "Antiviral Sulfated Polysaccharide from Navicula Directa, a Diatom Collected from Deep-Sea Water in Toyama Bay," Biol. Pharm. Bull., 29, 10, Oct. 2006, pp. 2135-2139.
Lee et al., "Chapter 8: Experimental Cell Fusion with Selected Siphonocladalean Algal Cells," Cell Fusion, 1987, pp. 167-178.
Lee et al., "Energetics of Photosynthetic Algal Growth: Influence of Intermittent Illumincation in Short (40s) Cycles," Journal of General Microbiology, 1981, 124, pp. 43-52.
Leliaert et al., "Phylogeny and Molecular Evolution of the Green Algae," Critical Reviews in Plant Sciences, 31, 2012, 46 pages.
Leonard et al., "Elongation of Long-chain Fatty Acids," Progress in Lipid Research, 43, 2004, pp. 36-54.
Leung et al., "Detection of Sphingomonas spp. in Soil by PCR and Sphingolipid Biomarker Analysis," Journal of Industrial Microbiology & Biotechnology, 1999, 23, pp. 252-260.
Lewin, "Culture and Nutrition of Some Apochlorotic Diatoms of the Genus Nitzschia," J. Gen. Microbiol., 1967, 46, pp. 361-367.
Lewin, "The Taxonomic Position of Phaeodactylum Tricornutum," J. Gen. Microbiol., 1958, 18 pp. 427-432.
León-Banares et al., 'Transgenic Microalgae as Green Cell-factories,' Trends in Biotechnology, vol. 22, No. 1, Jan. 2004, pp. 45-52.

(56) References Cited

OTHER PUBLICATIONS

Li, et al., "A Novel Potential Source of—Carotene: Eustigmatos cf. Polyphem (Eustigmatophyceae) and Pilot—Carotene Production in Bubble col. And Flat Panel Photobioreactors," Bioresource Technology, 117, 2012, pp. 257-263.

Li et al., "Effects of Nitrogen Sources on Cell Growth and Lipid Accumulation of Green Alga Neochloris Oleoabundans," Appl. Microbiol. Biotechnol., Aug. 2008, 8 pages.

Li et al., "Integration of Algae Cultivation as Biodiesel Production Feedstock with Municipal Wastewater Treatment: Strains Screening and Significance Evaluation of Environmental Factors," Bioresource Technology, 102, 2011, pp. 10861-10867.

Li et al., "Pilot-scale Isolation of Bioactive Extracellular Polymeric Substances from Cell-free Media of Mass Microalgal Cultures Using Tangential-flow Ultrafiltration," Process Biochemistry, 46, 2011, pp. 1104-1109.

Li et al., "Yield and Characteristics of Pyrolysis Products Obtained from Schizochytrium Limacinum Under Different Temperature Regimes," Energies, 2013, 6, pp. 3339-3352.

Liang et al., "Biomass and Lipid Productivities of Chlorella Vulgaris Under Autotrophic, Heterotrophic and Mixotrophic Growth Conditions," Biotechnol. Lett., 2009, 31, pp. 1043-1049.

Liang et al., "Differences in Growth, Total Lipid Content and Fatty Acid Composition Among 60 Clones of Cylindrotheca Fusiformis," Journal of Applied Phycology, 17, 2005, pp. 61-65.

Lin, et al., "Factors Affecting the Mixotrophic Maximum Growth of Chlorella pyrenoidosa," Graduate Institute of Agricultural Chemistry, National Taiwan University Accepted for Publication Oct. 1993, 10 pages.

Lin et al., "Effect of Ferric Ion on Nitrogen Consumption, Biomass and Oil Accumulation of a Scenedesmus rubescens-like Microalga," Bioresource Technology, 112, 2012, pp. 242-247.

Lin et al., "Effects of Nitrogen Source and Concentration on Biomass and Oil Production of a Scenedesmus rubescens Like Microalga," Bioresource Technology, 102, 2011, pp. 1615-1621.

Liu, et al., "Differential Lipid and Fatty Acid Profiles of Photoautotrophic and Heterotrophic Chlorella Zofingiensis: Assessment of Algal Oils for Biodiesel Production," Bioresource Technology, 102, 2011, pp. 106-110.

Liu, et al., "Effects of Organic Carbon Sources on Growth, Photosynthesis, and Respiration of Phaeodactylum Tricornutum," J. Appl. Phycol., 2009, 21, pp. 239-246.

Liu, et al., "Molasses-based Growth and Production of Oil and Astaxanthin by Chlorella Zofingiensis," Bioresource Technology, 107, 2012, pp. 393-398.

Liu et al., "Cell Cycle and Physiological Characteristics of Synechococcus (WH7803) in Chemostat Culture," Marine Ecology Progress Series, Nov. 1999, vol. 189, pp. 17-25.

Liu et al., "On the Mechanism of Synthesis of Acetic Acid Directly from CH4 and CO2 Using Dielectric-Barrier Discharges," Fuel Chemistry Division Preprints, 2003, 48(1), pp. 268-269.

Liu et al., "Secondary Carotenoids Formation by the Green Alga *Chlorococcum* sp.," Journal of Applied Phycology, 12, 2000, pp. 301-307.

Lodi et al., "Fed-Batch Mixotrophic Cultivation of Arthrospira (Spirulina) Platensis (Cyanophycea) with Carbon Source Pulse Feeding," Annals of Microbiology, 55, 3, 2005, pp. 181-185.

Logan, "Counting and Imaging Bacteria Using Fluorescent Microscopy & Electron Microscopy and Atomic Force Microscopy (AFM)," 76 pages, retrieved from http://www.engr.psu.edu/ce/enve/logan.htm, date unknown.

Lorenz, 'A Technical Review of Haematococcus Algae,' NatuRoseTM Technical Bulletin #060, Revision Date: Mar. 30, 1999, retrieved from the Internet: <http://www.cyanotech.com/pdfs/bioastin/axbul60.pdf>, retrieved on Dec. 14, 2011, 12 pages.

Lourenco et al., "Changes in Biochemical Profile of Tetraselmis gracilis I. Comparison of Two Culture Media," Aquaculture, 148, 1997, pp. 153-168.

Luca et al., "Acidophilic Algae from the Fumaroles of Mount Lawu (Java, locus Classicus of Cyanidium Caldarium Geitler)," Journal of the Societa Botanica Italiana, 1981, retrieved from http://www.tandfonline.com/loi/tplb19 on Aug. 5, 2013, 11 pages.

Luciano, "Antibacterial Agents," The History of Antibacterial Agents, An Introduction to Medicinal Chemistry, Graham L. Patrick, Oxford University Press, 1995, pp. 154-245, retrieved from http://www.chem.msu/su/rus/books/patrick/part2.

Ludwig et al., "*Synechococcus* sp. Strain PCC 7002 Transcriptome: Acclimation to Temperature, Salinity, Oxidative Stress, and Mixotrophic Growth Conditions," Frontiers in Microbiology, Oct. 2012, vol. 3, Article 354, 14 pages.

Luo et al., "Microbial Community Structures in a Closed Raw Water Distribution System Bio-film as Revealed by 454-pyrosequencing Analysis and the Effect of Microbial Biofilm Communities on Raw Water Quality," Bioresource Technology, Aug. 2013, 34 pages.

Lyford et al., "Inhibition of Rumen Cellulose Digestion by Extracts of Sericea Lespedeza," Journal of Animal Science, 1967, 26, pp. 632-637, 8 pages, downloaded from www.journalofanimalscience.org on Jan. 18, 2013.

Maher et al., "Pyrolysis of Triglyceride Materials for the Production of Renewable Fuels and Chemicals," Bioresource Technology, 98, 2007, pp. 2351-2368.

Malcata, "Microalgae and biofuels: A promising partnership?," Trends in Biotechnology Nov. 2011 vol. 29 No. 11 8 pgs.

Malicki et al., "Effect of Formic and Propionic Acid Mixture on *Escherichia coli* in Fish Meal Stored at 12° C.," Pakistan Journal of Nutrition, 3, 6, 2004, pp. 353-356.

Malinsky-Rushansky et al., "Excretion of Dissolved Organic Carbon by Phytoplankton of Different Sizes and Subsequent Bacterial Uptake," Marine Ecology Progress Series, Feb. 1996, vol. 132, pp. 249-255.

Manivannan et al., "Evaluation of Antioxidant Properties of Marine Microalga *Chlorella marina*, (Butcher, 1952)," Asian Pacific Journal of Tropical Biomedicine, 2012, pp. S342-S346.

Margalith, "Production of Ketocarotenoids by Microalgae," Appl. Microbiol. Biotechnol., 1999, 51, pp. 431-438.

Markelova et al., "A Comparison of Cytochemical Methods for the Rapid Evaluation of Microalgal Viability," Russian Journal of Plant Physiology, vol. 47, No. 6, 2000, pp. 815-819, translated from Fiziologiya Rastenii, vol. 47, No. 6, 2000, pp. 924-929.

Markou et al., "Cultivation of Filamentous Cyanobacteria (blue-green algae) in Agro-Industrial Wastes and Wastewaters: A Review," Applied Energy, 88, 2011, pp. 3389-3401.

Marquardt et al., "Intron-exon Structure and Gene Copy Number of a Gene Encoding for a Membrane-Intrinsic Light-Harvesting Polypeptide of the Red Alga *Galdieria sulphuraria*," Gene, 2000, 255, pp. 257-265.

Marquez et al., 'Growth Characteristics of Spirulina platensis in Mixotrophic and Heterotrophic Conditions,' Journal of Fermentation and Bioengineering, 1993, vol. 76, No. 5, pp. 408-410.

Martin et al., "Nitzschia Pseudodelicatissima—A Source of Domoic Acid in the Bay of Fundy, Eastern Canada," Marine Ecology Progress Series, Oct. 1990, vol. 67, pp. 177-182.

Matsunaga et al., "Screening of Marine Cyanobacteria for High Palmitoleic Acid Production," FEMS Microbiology Letters, 133, 1995, pp. 137-141.

Matthan et al., "Effects of Dietary Palmitoleic Acid on Plasma Lipoprotein Profile and Aortic Cholesterol Accumulation are Similar to Those of Other Unsaturated Fatty Acids in the F1B Golden Syrian Hamster," The Journal of Nutrition, Biochemical, Molecular, and Genetic Mechanisms, Downloaded from jn.nutrition.org on Oct. 18, 2013, 9 pages.

Mazor et al., "The Role of Cyanobacterial Exopolysaccharides in Structuring Desert Microbial Crusts," FEMS Microbiology Ecology, 21, 1996, pp. 121-130.

McCarthy, et al., "White Mutants of Chlamydomonas Reinhardtii are Defective in Phytoene Synthase," Genetics, Nov. 2004, 168(3), pp. 1249-1257.

Mehta et al., "Use of Ultraviolet Radiation to Achieve Bacteria-Free Algal Culture," Proc. Okla. Acad. Sci., 57, 1977, pp. 54-60.

Merola, et al., "Revision of Cyanidium Caldarium. Three Species of Acidophilic Algae," Official Journal of the Societa Botanica Italiana, Sep. 2009, downloaded from http://www.tandfonline.com/loi/tplb19, on Aug. 5, 2013, 9 pages.

(56) References Cited

OTHER PUBLICATIONS

Merrifield et al., "Assessment of Chlorogloeopsis as a Novel Microbial Dietary Supplement for Red Tilapia (*Oreochromis niloticus*)," Aquaculture, 299, 2010, pp. 128-133.

Mestankova et al., "Evolution of Algal Toxicity During (photo) Oxidative Degradation of Diuron," Aquatic Toxicology, 101, 2011, pp. 466-473.

Mitra et al., "Heterotrophic/Mixotrophic Cultivation of Oleaginous Chlorella Vulgaris on Industrial Co-Products," Algal Research, 1, 2012, pp. 40-48.

Moheimani et al., "Bioremediation and Other Potential Applications of Coccolithophorid Algae: A Review," Algal Research, 2012, 1, pp. 120-133.

Moheimani et al., "The Long-Term Culture of the Coccolithophore Pleurochrysis Carterae (Haptophyta) in Outdoor Raceway Ponds," Journal of Applied Phycology, 2006, 18, pp. 703-712.

Monod, "The Growth of Bacterial Cultures," Annual Review Microbiol., 1949, downloaded from arjournals.annualreviews.org on Sep. 17, 2007, 25 pages.

Moorthi et al., "Mixotrophy: A Widespread and Important Ecological Strategy for Planktonic and Sea-Ice Nanoflagellates in the Ross Sea, Antartica," Aquatic Microbial Ecology, Mar. 2009, vol. 54, pp. 269-277.

Moraes, et al., "C-Phycocyanin Extraction from Spirulina platensis Wet Biomass," Brazilian Journal of Chemical Engineering, Mar. 2011, vol. 28, No. 1, pp. 45-49.

Morais, et al., "*Phaeodactylum tricornutum* Microalgae Growth Rae in Heterotrophic and Mixotrophic Conditions," Thermal Engineering, vol. 8, No. 1, Jun. 2009, pp. 84-89.

Mordukhova et al., "Improved Thermostability and Acetic Acid Tolerance of *Escherichia coli* via Directed Evolution of Homoserine o-Succinyltransferase," Applied and Environmental Microbiology, Dec. 2008, vol. 74, No. 24, p. 7660-7668.

Morgan, "Cyclin-Dependent Kinases: Engines, Clocks, and Microprocessors," Annu. Rev. Cell Dev. Biol., 1997, 13, pp. 261-291.

Morgan et al., "Unsaturated Fatty Acids as Cytoprotective Agents in the Pancreatic B-Cell," Prostaglandins, Leukotrienes and Essential Fatty Acids, 82, 2010, pp. 231-236.

Morris, et al., "The Stereospecificity of Desaturations of Long-Chain Fatty Acids in Chlorella Vulgaris," Biochemical and Biophysical Research Communications, vol. 28, No. 6, 1967, pp. 904-908.

Mozaffarian, et al., "Trans-Palmitoleic Acid, Metabolic Risk Factors, and New-Onset Diabetes in U.S. Adults: A Cohort Story," Annals of Internal Medicince 2010: 153(12) 790-799.

Muhling et al., "Screening Arthrospira (Spirulina) Strains for Heterotrophy," Journal of Applied Phycology, 2005, 17, pp. 129-135.

Mulbry, et al., "Biofertilizers from Algal Treatment of Dairy and Swin Manure Effluents: Characterization of Algal Biomass as a Slow Release Fertilizer," Journal of Vegetable Science, vol. 12(4), 2006, pp. 107-125.

Mumma et al., "Strong Release of Methane on Mars in Northern Summer 2003," NASA Public Affairs, Jan. 2009, 27 pages.

Munoz et al., "Algal-bacterial Processes for the Treatment of Hazardous Contaminants: A Review," Water Research, 40, 2006, pp. 2799-2815.

Mutanda, et al., "Bioprospecting for hyper-lipid Producing Microalgal Strains for Sustainable Biofuel Production," Bioresource Technology, 102, 2011, pp. 57-70.

Miron et al., "Shear Stress Tolerance and Biochemical Characterization of Phaeodactylum tricornutum in Quasi Steady-state Continuous Culture in Outdoor Photobioreactors," Biochemical Engineering Journal, 16, 2003, pp. 287-297.

Nagy et al., "Enhancement of Oxygen Mass Transfer Rate in the Presence of Nanosized Particles," Chemical Engineering Science, 62, 2007, pp. 7391-7398.

Nakamura et al., "Growth and Grazing of a Heterotrophic Dinoflagellate, Gyrodinium Dominans, Feeding on a Red Tide Flagellate, Chattonella Antigua," Marine Ecology Progress Series, Jun. 1992, vol. 82, pp. 275-279.

Nakazawa, et al., "Optimization of culture conditions of the *Thraustochytrid aurantiochytrium* sp. strain 18W 13a for squalene production," Bioresource Technology 109 (2012) 287-297.

Narro et al., "Metabolism of Phenanthrene by the Marine Cyanobacterium Agmenellum Quadruplicatum PR-6," Applied and Environmental Microbiology, 1992, vol. 58, No. 4, pp. 1351-1359.

Neilson et al., "The Uptake and Utilization of Organic Carbon by Algae: An Essay in Comparative Biochemistry," Phycologia, 1974, vol. 13, pp. 227-264.

Nestel et al., "Effects of Increasing Dietary Palmitoleic Acid Compared with Palmitic and Oleic Acids on Plasma Lipids of Hypercholesterolemic Men," Journal of Lipid Research, vol. 35, 1994, pp. 656-662.

Nguyen et al., "Removal of Trace Organic Contaminants by an MBR Comprising a Mixed Culture of Bacteria and White-rot Fungi," Bioresource Technology, 148, 2013, pp. 234-241.

Nguyen et al., "Removal of Trace Organic Contaminants by an MBR Comprising a Mixed Culture of Bacteria and White-rot Fungi," Bioresource Technology, Aug. 2013, 34 pages.

Nicolas et al., "Effect of Light on Glucose Utilization by Euglena gracilis," Plant Physiol., 1980, vol. 65, pp. 631-634.

Nishida et al., "*Escherichia coli* Engineered to Produce Eicosapentaenoic Acid Becomes Resistant Against Oxidative Damages," FEBS Letters 580, 2006, pp. 2731-2735.

Nishida et al., "The Cell Membrane-Shielding Function of Eicosapentaenoic Acid for *Escherichia coli* Against Exogenously Added Hydrogen Perioxide," FEBS Letters 580, 2006, pp. 6690-6694.

Niu et al., "Large-scale Recovery of C-phycocyanin from Spirulina platensis Using Expanded Bed Adsorption Chromatography," Journal of Chromatography B, 2007, 850, pp. 267-276.

Nodwell et al., "Direct use of inorganic colloidal iron by marine mixotrophic phytoplankton," Limnol. Oceanogr., 46(4) 2001, 765-777.

Northcote et al., "The Chemical Composition and Structure of the Cell Wall of Chlorella pyrenoidosa," Biochemical Journal, 1958, vol. 70, No. 3, pp. 391-397.

Nowruzi et al., "A Gene Expression Study on Strains of Nostoc (Cyanobacteria) Revealing Antimicrobial Activity Under Mixotrophic Conditions," African Journal of Biotechnology, vol. 11, 51, Jun. 2012, pp. 11296-11308.

Nygaard et al., "Bacterivory in Algae: A Survival Strategy During Nutrient Limitation," Limnol. Oceanogr., 38(2), 1993, pp. 273-279.

O'Brien et al., "Formation and Dissimilation of Oxalacetate and Pyruvate in Pseudomonas citronellolis Grown on Nanocarbohydrate Substrates," Journal of Bacteriology, Apr. 1977, vol. 130, No. 1, pp. 131-135.

O'Leary, "The Fatty Acids of Bacteria," Bacteriology Reviews, 1962, vol. 26, pp. 421-447.

Oesterhelt et al., "The Genome of the Thermoacidophilic Red Microalga *Galdieria sulphuraria* Encodes a Small Family of Secreted Class III Peroxidases that Might be Involved in Cell Wall Modification," Planta, 2008, 227, pp. 353-362.

Ogbonna et al., "Heterotrophic Cultivation of Euglena gracilis Z for Efficient Production of a-tocopherol," Journal of Applied Phycology, 10, 1998, pp. 67-74.

Oh et al., "Long-Term Outdoor Cultivation by Perfusing Spent Medium for Biodiesel Production from Chlorella Minutissima," Journal of Bioscience and Bioengineering, 2010, vol. 110, No. 2, pp. 194-200.

Ohta, et al., "Antibiotic Substance Produced by a Newly Isolated Marine Microalga, *Chlorococcum* HS-101," Bull. Environ. Contam. Toxicol., 1993, 50, pp. 171-178.

Oilgae, "Oilgae Guide to Algae-based Wastewater Treatment, A Sample Report," retrieved from http://www.oilgae.com/ref.report/wastewater_treatment/wastewater_treatment.html on Oct. 18, 2013, 40 pages.

Okuyama et al., "Significance of Antioxidative Functions of Eicosapentaenoic and Docosahaxaenoic Acids in Marine Microor-

(56) References Cited

OTHER PUBLICATIONS ganisms," Applied and Environmental Microbiology, Feb. 2008, vol. 74, No. 3, pp. 570-574, downloaded from http://aem.asm.org on Jun. 26, 2012.
Oliveira, et al., "Caracterizacao de Isolados de *Acidovorax avenae* subsp. citrulli," Fitopatologia Brasileira 2007, 32 480-487 English.
Olsson-Francis et al., "Use of Cyanobacteria for in-situ Resource Use in Space Applications," Planetary and Space Science, 58, 2010, pp. 1279-1285.
Oltmann et al., "Modification of the pH-Auxostat Culture Method for the Mass Cultivation of Bacteria," Biotechnology and Bioengineering, vol. XX, 1978, pp. 921-925.
Oncel, et al., "Comparison of differenct cultivation modes and light intensities using mono-cultures and co-cultures of Haematococcus pluvialis and Chlorella zofingiensis," Journal of Chem Technol Biotechnol 2011, 86, pp. 414-420.
Orcutt et al., "Effect of Light Intensity Upon Lipid Composition of Nitzschia closterium (Cylindrotheca fusiformis)," Lipids, vol. 9, No. 12, Jun. 1974, pp. 1000-1003.
Otles et al., "Fatty Acid Composition of *Chlorella* and *Spirulina* Microalgae Species," Drugs, Cosmetics, Forensic Sciences, Journal of AOAC International, 2001, vol. 84, No. 6, pp. 1708-1714.
Otsuka et al., "Presence of Previously Undescribed Bacterial Taxa in Non-axenic Chlorella Cultures," J. Gen. Appl. Microbiol., 54, 2008, pp. 187-193.
Ouyang et al., 'The Effects of Light Intensities, Temperatures, pH and Salinities on Photosynthesis of Chlorella,' Journal of Wuhan Botanical Research, 2010, 28 (1), pp. 49-55.
Paasche, "Silicon and the Ecology of Marine Plankton Diatoms. I. Thalassiosira pseudonana (Cyclotella nana) Grown in a Chemostat with Silicate as Limiting Nutrient," Marine Biology, 1973, 19, pp. 117-126.
Paerl, "Controlling Eutrophication Along the Freshwater-Marine Continuum: Dual Nutrient (N and P) Reductions are Essential," Estuaries and Coasts, 2009, 32, pp. 593-601.
Pahl, "Heterotrophic Production of the Microalgae *Cyclotella cryptica*; Feed for Aquaculture," A Thesis Submitted for the Degree of Doctor of Philosophy, May 2010, School of Chemical Engineering, The University of Adelaide, Australia, 24 pages.
Pahl et al., "Heterotrophic Growth and Nutritional Aspects of the Diatom Cyclotella cryptica (Bacillariophyceae): Effect of Nitrogen Source and Concentration," J. Appl. Phycol., 2012, 24, pp. 301-307.
Pahl et al., "Heterotrophic Growth and Nutritional Aspects of the Diatom Cyclotella Cryptica (Bacillariophyceae): Effect of Some Environmental Factors," Journal of Bioscience and Bioengineering, vol. 109, No. 3, 2010, pp. 235-239.
Pankratz, "Evaporation—A Wastewater Treatment Alternative," Shimadzu, Online TOC Analyzer, Dec. 2000, retrieved from http://www.wwdmag.com/wastewater/evaporation-wastewater-treatment-alternative on Jul. 25, 2013, 3 pages.
Pantoom et al., "Potent Family-18 Chitinase Inhibitors, X-Ray Structures, Affinities, and Binding Mechanisms," The Journal of Biological Chemistry, Jul. 2011, vol. 286, No. 27, pp. 24312-24323.
Papanikolaou, "Oleaginous Yeasts: Biochemical Events Related with Lipid Synthesis and Potential Biotechnological Applications," Fermentation Technology, 2011, vol. 1, Issue 1, 3 pages.
Park et al., "Mixotrophic and Photoautotrophic Cultivation of 14 Microalgae Isolates from Saskatchewan, Canada: Potential Applications for Wastewater Remediation for Biofuel Production," J. Appl. Phycol., 2012, 24, pp. 339-348.
Parker, "Facultative Heterotrophy in Certain Soil Algae From the Ecological Viewpoint," Ecology vol. 42 No. 2 pp. 381-386.
Patil et al., 'Fatty Acid Composition of 12 Microalgae for Possible Use in Aquaculture Feed,' Aquacult. Int., 2007, 15, 9 pages.
Paul et al., "Isolation and Chemical Structure of Amphidinol 2, a Potent Hemolytic Compound from Marine Dinoflagellate Amphidinium Klebsii," Tetrahedron Letters, 1995, vol. 36, No. 35, pp. 6279-6282.
Pearce et al., "The Incomplete Tricarboxylic Acid Cycle in the Blue-Green Alga *Anabaena variabilis*," J. Gen. Microbiol., 1969, 55, pp. 371-378.
Pearce et al., "The Incorporation and Metabolism of Glucose by Anabaena Variabilis," J. Gen. Microbiol., 1969, 54, pp. 451-462.
Peng, "The Use of Fertilizers on Aquaculture in China," Soil and Fertilizer Research Institute, Guangdong Academy of Agriculture Sciences, 12 pages, retrieved from www.fertilizer.org/ifacontent/download/7050/111332/version/1/file, date unknown.
Perez-Garcia, et al., "Heterotrophic Cultures of Microalgae: Metabolism and Potential Products," Water Research, 2011, 45, pp. 11-36.
Pernet et al., "Variation of Lipid Class and Fatty Acid Composition of *Chaetoceros muelleri* and *Isochrysis* sp. Grown in a Semicontinuous System," Aquaculture, 221, 2003, pp. 393-406.
Petkov et al., "Which are Fatty Acids of the Green Alga Chlorella?," Biochemical Systematics and Ecology, 35, 2007, pp. 281-285.
Pham et al., "Maximization of Volatile Fatty Acids Production from Alginate in Acidogenesis," Bioresource Technology, Aug. 2013, 17 pages.
Ping, "The Growth and Fatty Acid Formation of Monodus subterraneus Under Mixotrophic Conditions," A Thesis Submitted in Partial Fulfillment of the Requirements for the Degree of Master of Philosophy at the University of Hong Kong, Feb. 2000, 136 pages, retrieved from http://hdl.handle.net/10722/33494.
Pleissner et al., "Biomass Composition of Blue Mussels, *Mytilus edulis*, is Affected by Living Site and Species of Ingested Microalgae," International Scholarly Research Network, 2012, Article ID 902152, 13 pages.
Popovich et al., "Lipid Quality of the Diatoms Skeletonema costatum and Navicula gregaria from the South Atlantic Coast (Argentina): Evaluation of its Suitability as Biodiesel Feedstock," J. Appl. Phycol., 2012, 24, pp. 1-10.
Potvin et al., "Strategies for High-level Recombinant Protein Expression in Transgenic Microalgae: A Review," Biotechnology Advances, 28, 2010, pp. 910-918.
Powell et al., "Factors Influencing Luxury Uptake of Phosphorus by Microalgae in Waste Stabilization Ponds," Environmental Science & Technology, 2008, vol. 42, No. 16, pp. 5958-5962.
Pratiwi et al., Fatty Acid Synthesis by Indonesian Marine Diatom, Chaetoceros gracilis, HAYATI Journal of Biosciences, Dec. 2009, vol. 16, No. 4, Dec. 2009, pp. 151-156.
Pratoomyot et al., "Fatty Acids Composition of 10 Microalgal Species," J. Sci. Technol., vol. 27, No. 6, Nov.-Dec. 2005, pp. 1179-1187.
Price-Carter, et al., "Polyphosphate Kinase Protects *Salmonella enterica* from Weak Organic Acid Stress," Journal of Bacteriology, May 2005, vol. 187, No. 9, pp. 3088-3099.
Pultarova, "Snail Astronaut Survived with an Algae-based Life Support System," Space Safety Magazine, May 2012, 7 pages.
Radmer et al., "Light-Driven Uptake of Oxygen, Carbon Dioxide, and Bicarbonate by the Green Alga *Scenedesmus*," Plant Physiol., 1980, 65, pp. 723-729.
Ramos et al., "Development of a Process for Large-scale Purification of C-phycocyanin from Synechocystis aquatilis Using Expanded Bed Adsorption Chromatography," Journal of Chromatography B, 2011, 879, pp. 511-519.
Rao, "Production of Astaxanthin from Cultured Green Alga *Haematococcus pluvialis* and its Bilogical Activities," A Thesis Submitted to the Department of Biotechnology of University of Mysore in Fulfillment of the Requirement for the Degree of Doctor of Philosophy in Biotechnology. Jan. 2011, Part 5of6 pp. 231-287.
Rao, "Production of Astaxanthin from Cultured Green Alga *Haematococcus pluvialis* and its Biological Activities," A Thesis submitted to the Department of Biotechnology of University of Mysore in fulfillment of the requirement for the degree of Doctor of Philosophy in Biotechnology, Jan. 2011. Part 1of6 pp. 1-56.
Rao, "Production of Astaxanthin from Cultured Green Alga *Haematococcus pluvialis* and its Biological Activities," A Thesis submitted to the Department of Biotechnology of University of Mysore in fulfillment of the requirement for the degree of Doctor of Philosophy in Biotechnology, Jan. 2011. Part 2of6 pp. 57-113.
Rao, "Production of Astaxanthin from Cultured Green Alga *Haematococcus pluvialis* and its Biological Activities," A Thesis submitted to the Department of Biotechnology of University of Mysore in fulfillment of the requirement for the degree of Doctor of Philosophy in Biotechnology, Jan. 2011. Part 3of6 pp. 114-170.

(56) References Cited

OTHER PUBLICATIONS

Rao, "Production of Astaxanthin from Cultured Green Alga *Haematococcus pluvialis* and its Biological Activities," A Thesis Submitted to the Department of Biotechnology of University of Mysore in Fulfillment of the Requirement for the Degree of Doctor of Philosophy in Biotechnology. Jan. 2011, Part 4of6 pp. 171-230.
Rao, "Production of Astaxanthin from Cultured Green Alga *Haematococcus pluvialis* and its Biological Activities," A Thesis submitted to the Department of Biotechnology of University of Mysore in Fulfillment of the Requirement for the Degree of Doctor of Philosophy in Biotechnology. Jan. 2011, Part 6of6 pp. 288-342.
Raso et al., "Effect of Oxygen Concentration on the Growth of *Nannochloropsis* sp. at Low Light Intensity," J. Appl. Phycol., Sep. 2011, 9 pages.
Ratledge et al., "Production of Docosahexaenoic Acid by Crypthecodinium Cohnii Grown in a pH-Auxostat Culture with Acetic Acid as Principal Carbon Source," Lipids, vol. 36, No. 11, 2011, pp. 1241-1246.
Raven, "Effects on Marine Algae of Changed Seawater Chemistry with Increasing Atmospheric CO2," Biology and Environment: Proceedings of the Royal Irish Academy, vol. 111B, No. 1, 2011, DOI: 10.3318/BIOE.2011.01.1, pp. 1-17.
Ravi et al., "Screening and Evaluation of Probiotics as a Biocontrol Agent Against Pathogenic Vibrios in Marine Aquaculture," Letters in Applied Microbiology ISSN 0266-8254, 45, 2007, pp. 219-223.
Rawat et al., "Dual Role of Microalgae: Phycoremediation of Domestic Wastewater and Biomass Production for Sustainable Biofuels Production," Applied Energy, 2010, 14 pages.
Reasoner, "Heterotrophic Plate Count Methodology in the United States," International Journal of Food Microbiology, 92, 2004, pp. 307-314.
Reazin, "The Metabolism of Glucose by the Alga Ochromonas Malhamensis," Plant Physiology, Jul. 1956, 31(4), pp. 299-300.
Rehm, "Use of Banded Fertilizer for Corn Production," 2002, retrieved from http://www.extension.umn.edu/distribution/cropsystems/DC7425.html on Apr. 15, 2013, 9 pages.
Renaud et al., "The Gross Chemical Composition and Fatty Acid Composition of 18 Species of Tropical Australian Microalgae for Possible Use in Mariculture," Aquaculture, 170, 1999, pp. 147-159.
Richardson et al., "Enhanced Survival of the Cyanobacterium Oscillatoria terebriformis in Darkness Under Anaerobic Conditions," Applied and Environmental Microbiology, Sep. 1987, vol. 53, No. 9, pp. 2151-2158.
Rocha, "With a Little Help from Prokaryotes," Science, vol. 339, Mar. 2013, pp. 1154-155, downloaded from www.sciencemag.org on Aug. 25, 2013.
Rocha et al., 'Growth Aspects of the Marine Microalga Nannochloropsis gaditana,' Biomolecular Engineering, 20, 2003, pp. 237-242.
Roe, et al., "Inhibition of *Escherichia coli* Growth by Acetic Acid: A Problem with Methionine Biosynthesis and Homocysteine Toxicity," Microbiology, 2002, 148, pp. 2215-2222.
Rothhaupt, "Utilization of Substitutable Carbon and Phosphorus Sources by the Mixotrophic *Chrysophyte ochromonas* SP.," Ecology 77(3) 1996 pp. 706-715.
Roubeix et al., Effect of Salinity on Growth, Cell Size and Silicification of an Euryhaline Freshwater Diatom: Cyclotella meneghiniana Kutz., Transitional Waters Bulletin, 1, 2008, pp. 31-38.
Rovira et al., "Interactions Between Plant Roots and Soil Microorganisms," Annu. Rev. Microbiol., 1965, pp. 241-266, downloaded from www.annualreviews.org on Feb. 19, 2013.
Running et al., "Heterotrophic Production of Ascorbic Acid by Microalgae," Journal of Applied Phycology, 6, 1994, pp. 99-104.
Rutala, et al., "Guideline for Disinfection and Sterilization in Healthcare Facilities," Healthcare Infection Control Practices Advisory Committee, Centers for Disease Control and Prevention, 2008, 158 pages, retrieved from www.cdc.gov/hicpac/Disinfection_Sterilization/acknowledg.html.
Rutgers, "A Simple and Effective Method to Enhance Lipid Synthesis in Microalgae for Biofuel Production," 1 page.
Ryan, "Understanding and Managing Cell Culture Contamination" Corning Life Sciences Technical Bulletin, Corning Incorporated Life Sciences, 2002, 24 pages.
Rösch et al., "Materials Flow Modeling of Nutrient Recycling in Biodiesel Production from Microalgae," Bioresource Technology, 107, 2012, pp. 191-199.
Safford et al., "Positional Distribution of Fatty Acids in Monogalactosyl Diglyceride Fractions from Leaves and Algae, Structural and Metabolic Studies," Biochim. Biophys. Acta, 210, 1970, pp. 57-64.
Safonova et al., "Growth Promoting and Inhibiting Effects of Extracellular Substances of Soil Microalgae and Cyanobacteria on *Escherichia coli* and *Micrococcus luteus*," Phycological Research, 2005, 53, pp. 189-193.
Saguez et al., "Chitinase Inhibitors and Chitin Mimetics for Crop Protection," Pest Technology, 2, 2, pp. 81-86, 2008, Global Science Books.
Saint-Louis, et al., "Distribution and effects of tributyltin chloride and its degradation products on the growth of the Marine Alga pavlova Lutheri in Continuous Culture," Wat. Res. vol. 28 No. 12 pp. 2533-2544 1994.
Saithong, et al., "Prevention of bacterial contamination using acetate-tolerant Schizosaccharomyces pombe during bioethanol production from molasses," Journal of Bioscience and Bioengineering 2009 vol. 108 No. 3 216-219.
Sakuradani et al., Identification of a Novel Fatty Acid Elongase with a Wide Substrate Specificity from Arachidonic Acid-producing Fungus *Mortierella alpina* 1S-4, Appl. Microbiol. Biotechnol., 2009, 84, pp. 709-716.
Salas, et al., "Biochemical characterization of a high-palmitoleic acid Helianthus annuus mutant," Plant Physiology and Biochemistry 42 (2004) 373-381.
Salim, "Heterotrophic Growth of *Ankistrodesmus* SP. for Lipid Production Using Cassava Starch Hydrolysate as a Carbon Source," The International Journal of Biotechnology, 2013, 2, 1, pp. 42-51.
Sanchez, et al., "Mixotrophic Culture of Chlorella Pyrenoidosa with Olive-Mill Wastewater as the Nutrient Medium," Journal of Applied Phycology, 13, 2001, pp. 443-449.
Sanders et al., "Nutrient Acquisition and Population Growth of a Mixotrophic Alga in Axenic and Bacterized Cultures," Microbial Ecology, 2001, 42, pp. 513-523.
Sandnes, et al., 'Real-time Monitoring and Automatic Density Control of Large-Scale Microalgal Cultures Using Near Infrared (NIR) Optical Density Sensors,' Journal of Biotechnology 122, 2006, pp. 209-215.
Sarada et al., 'Phycocyanin from *Spirulina* sp: Influence of Processing of Biomass on Phycocyanin Yield, Analysis of Efficacy of Extraction Methods and Stability Studies on Phycocyanin,' Process Biochemistry, 34, 1999, pp. 795-801.
Sato, et al., "Temperature shift-induced responses in lipids in the blue-green alga, Anabaena Variables," Biochimica et Biphysica Acta, 619 (1980) 353-366.
Saunders, "Potential Heterotrophy in a Natural Population of *Oscillatoria agardhii* Var. Isothrix Skuja," Limnology and Oceanography Sep. 1972 V. 17(5) pp. 704-711.
Saunders et al., "Chapter 25. Chemically Induced Fusion of Plant Protoplasts," Cell Fusion, Edited by Arthur E. Sowers, ISBN 0-306-42351-0, 1987, 497-520, 26 pages.
Scala, et al., "Genome Properties of the Diatom Phaeodactylum tricornutum," Plant Physiology, Jul. 2002, vol. 129, pp. 993-1002.
Scarsella, et al., "Study on the Optimal Growing Conditions of Chlorella Vulgaris in Bubble Column Photobioreactors," Chemical Engineering Transactions, 2010, vol. 20, pp. 85-90.
Scherer et al., "A New UV-A/B Protecting Pigment in the Terrestrial Cyanobacterium Nostoc commune," Plant Physiol., 1988, 88, pp. 1055-1057.
Schmidt et al., "Heterotrophic High Cell-Density Fed-Batch Cultures of the Phycocyanin-Producing Red Alga *Galdieria sulphuraria*," Biotechnology and Bioengineering, vol. 90, No. 1, Apr. 2005, Published online Feb. 18, 2005 in Wiley InterScience (www.interscience.wiley.com), 8 pages.
Schonknecht et al., "Gene Transfer from Bacteria and Archaea Facilitated Evolution of an Extremophilic Eukaryote," Science, vol. 339, Mar. 2013, pp. 1207-1210.

(56) References Cited

OTHER PUBLICATIONS

Seaver et al., "Hydrogen Peroxide Fluxes and Compartmentalization Inside Growing *Escherichia coli*," Journal of Bacteriology, Dec. 2001, vol. 183, No. 24, pp. 7182-7189.
Seckbach, et al., "Sterols and Phylogeny of the Acidophilic Hot Springs Algae Cyanidium Caldarium and Galdieria Sulphuraria," Phytochemistry, 1993, vol. 34, No. 5, pp. 1345-1349.
Seixas et al., "Nutritional Value of the Cryptophyte Rhodomonas lens for *Artemia* sp.," Journal of Experimental Marine Biology and Ecology, 381, 2009, 9 pages.
Sevilla, et al., "Pilot-Plant-Scale Outdoor Mixotrophic Cultures of Phaeodactylum Tricornutum Using Glycerol in Vertical Bubble Column and Airlift Photobioreactors: Studies in Fed-Batch Mode," Biotechnology Progress, 2004, vol. 20, Issue 3, pp. 728-236, retrieved from http://onlinelibrary.wiley.com/doi/10.1021/bp034344f/ abstract?systemMessage=Wiley+Onl . . . on Jun. 7, 2012, 3 pages.
Sforza, et al., "Excess CO2 Supply Inhibits Mixotrophic Growth of Chlorella Photothecoides and Nannochloropsis Salina," Bioresource Technology, 104, 2012, pp. 523-529.
Shamala, et al., "Studies on Scenedesmus acutus Growth. I. Effect of Autotrophic and Mixotrophic Conditions on the Growth of Scenedesmus acutus," Biotechnology and Bioengineering 1982 vol. 24 pp. 1287-1299.
Shapouri et al., "Evaluation of Antimicrobial Effect of Hops Extracts on Intramacrophages Brucella abortus and B. melitensis," Jundishapur Journal of Microbiology, 2011, 4, Supp. 1, pp. S51-S58.
Sharma et al., "Process Optimization for Poly- -hydroxybutyrate Production in a Nitrogen Fixing Cyanobacterium, Nostoc muscorum Using Response Surface Methodology," Bioresource Technology, 98, 2007, pp. 987-993.
Sharma et al., "Studies on Poly- -hydroxybutyrate Synthase Activity of Nostoc muscorum," J. Gen. Appl. Microbiol., 52, 2006, pp. 209-214.
Shen et al., "Heterotrophic Culture of Chlorella protothecoides in Various Nitrogen Sources for Lipid Production," Appl. Biochem. Biotechnol., 2010, 160, pp. 1674-1684.
Shi, et al., "Production of biomass and lutein by chlorella protothecoides at various glucose concentrations in heterotrophic cultures," Process Biochemistry 34 (1999) 341-347.
Shi et al., "Heterotrophic Production of Biomass and Lutein by Chlorella protothecoides on Various Nitrogen Sources," Enzyme and Microbial Technology, 27, 2000, pp. 312-318.
Shimamura et al., "5, 5-Dimethyl-3-(5-methyl-3-oxo-2-phenyl-2,3-dihydro-1H-pyrazol-4-yl)-1-phenyl-3-(trifluoromethyl)-3,5,6,7-tetrahydro-1H-indole-2, 4-dione, a Potent Inhibitor for Mammalian Elongase of Long-Chain Fatty Acids Family 6: Examination of Its Potential Utility as a Pharmacological Tool," The Journal of Pharmacology and Experimental Therapeutics, vol. 330, No. 1, pp. 249-356.
Shimamura et al., "Discovery and Characterization of a Novel Potent, Selective and Orally Active Inhibitor for Mammalian ELOVL6," European Journal of Pharmacology, 630, 2010, pp. 34-41.
Shukla et al., "Potassium-induced Inhibition of Photosynthesis and Associated Electron Transport Chain of Microcystis: Implication for Controlling Cyanobacterial Blooms," Harmful Algae, 5, 2006, pp. 184-191.
Sijtsma et al., "Chapter 8. Alternative Carbon Sources for Heterotrophic Production of Docosahexaenoic Acid by the Marine Alga *Crypthecodinium cohnii*," Single Cell Oils, 2010, pp. 107-123, ISSN: 9781893997806.
Sims, "Clearing the Way for Byproduct Quality," Biodiesel Magazine, Oct. 2011, 3 pages, retrieved from http://www.biodieselmagazine.com/articles/8137/clearing-the-way-for-byproduct-quality on Oct. 18, 2013.
Singh, et al., "Bioactive Compounds from Cyanobacteria and Microalgae: An Overview," Critical Reviews in Biotechnology 25: 73-95 2005.
Singh, et al., "Commercialization Potential of Microalgae for Biofuels Production," Renewable and Sustainable Energy Reviews, 14, 2010, pp. 2596-2610.
Singh, et al., "Microalgal System for Treatment of Effluent from Poultry Litter Anaerobic Digestion," Bioresource Technology, 102, 2011, pp. 10841-01848.
Singh et al., "Mechanism and Challenges in Commercialisation of Algal Biofuels," Bioresource Technology, 102, 2011, pp. 26-34.
Sivakumar et al., "Integrated Green Algal Technology for Bioremediation and Biofuel," Bioresource Technology, 107, 2012, pp. 1-9.
Skinner, "Effects of Calorie Restriction on Life Span of Microorganisms," Appl. Microbiol. Biotechnol., 2010, 88, pp. 817-828.
Skovgaard, et al., "Food Uptake in the harmful alga *Prymnesium parvum* mediated by excreted toxins," Limnol. Oceanogr. 48(3) 2003 pp. 1161-1166.
Sloth, et al., "Accumulation of Phycocyanin in Heterotrophic and Mixotrophic Cultures of the Acidophilic Red Alga *Galdieria sulphuraria*," Enzyme and Microbial Technology, 38, 2006, pp. 168-175.
Smart et al., "Targeted Genetic Inactivation of the Photosystem I Reaction Center in the Cyanobacterium *Synechocystis* sp. PCC 6803," The EMBO Journal, 1991, vol. 10, No. 11, pp. 3289-3296.
Smolinska, "Mutagenic and toxic effects of some herbicides on algae *Chlorella vulgaris*," Food and Agriculture Organization of the UN, Abstract Only, accessed via website Dec. 27, 2014.
Song et al., "Chapter 1. Recent Application of Probiotics in Food and Agricultural Science," InTech, 2012, DOI: 10.5772/50121, available from: http://www.intechopen.com/books/profiotics/recent-application-of-probiotics-in-food-and-agricultural-science, 34 pages.
Soni et al., "Extraction, Purification and Characterization of Phycocyanin from Oscillatoria quadripunctulata—Isolated from the Rocky Shores of Bet-Dwarka, Gujarat, India," Process Biochemistry, 41, 2006, pp. 2017-2023.
Sowers, et al., "Growth of Acetotrophic, Methane-Producing Bacteria in a pH Auxostat," Current Microbiology, vol. 11, 1984, pp. 227-229.
Spanova, et al., "Squalene—biochemistry, molecular biology, process biotechnology, and applications," Eur. J. Lipid Sci. Technol. 2011 113, 1299-1320.
Specht et al., "Micro-algae Come of Age as a Platform for Recombinant Protein Production," Biotechnol Lett., 2010, 32, pp. 1373-1383.
Spolaore et al., 'Commercial Applications of Microalgae, Journal of Bioscience and Bioengineering, vol. 101, No. 2, 2006, pp. 87-96.
Spreitzer et al., "Nuclear Suppressors of the Photosensitivity Associated with Defective Photosynthesis in Chlamydomonas reinhardii," Plant Physiol., 1983, 71, pp. 35-39.
Spreitzer et al., "Photosynthesis-Deficient Mutants of Chlamydomonas Reinhardii with Associated Light-Sensitive Phenotypes," Plant Physiol., 1981, vol. 67, pp. 565-569.
Srivastava et al., "Chapter 2.69 Oxygen Mass Transfer in Bioreactors," Comprehensive Biotechnology, Second Edition, 2011, pp. 947-956, IBSN: 978-0-08-088504-9.
Steels, et al., "Sorbic Acid Resistance: The Inoculum Effect," Yeast, 2000, 16, pp. 1173-1183.
Stoecker, "Conceptual Models of Mixotrophy in Planktonic Protists and Some Ecological and Evolutionary Implications," European Journal of Protistology, 34, 1998, pp. 281-290.
Stoecker, "Mixotrophy Among Dinoflagellates," Journal of Eukaryot. Microbiol., Aug. 1999, vol. 46, No. 4, pp. 397-401.
Su et al., "Factors Affecting Lipid Accumulation by Nannochloropsis Oculata in a Two-Stage Cultivation Process," J. Appl. Phycol., 2011, 23, pp. 903-908.
Subashchandrabose, et al., "Mixotrophic Cyanobacteria and Microalgae as Distinctive Biological Agents for Organic Pollutant Degradation," Environment International, 51, 2013, pp. 59-72.
Suman et al., "Culture medium optimization and lipid profiling of Cylindrotheca, a lipid- and polyunsaturated fatty acid-rich pennante diatom and potential source of eicosapentaenoic acid," vol. 55, Issue 3 pp. 289-299.
Sun et al., "Sugar-Based Growth, Astaxanthin Accumulation and Carotenogenic Transcription of Heterotrophic Chlorella Zofingiensis (Chlorophyta)," Process Biochemistry, 43, 2008, pp. 1288-1292.
Suryakumar et al., "Medicinal and Therapeutic Potential of Sea Buckthorn (*Hippaphae rhamnoides* L.)," Journal of Ethnopharmacology, 138, 2011, pp. 268-278.

(56) References Cited

OTHER PUBLICATIONS

Suslow et al., "Beneficial Bacteria Enhance Plant Growth," California Agriculture, Nov.-Dec. 1979, pp. 15-17.
Swaaf, et al., Ch 4. "High-cell-density fed-batch cultivation of the docosahexaenoic acid producing marine alga *Crypthecodinium cohnii*," from the book "Docosahexaenoic acid production by the marine alga *Crypthecodinium cohnii*" specifically pp. 76-82 Apr. 7, 2003.
Sánchez et al., "Influence of Culture Conditions on the Productivity and Lutein Content of the New Strain Scenedesmus almeriensis," Process Biochemistry, 43, 2008, pp. 398-405.
Sørensen et al., "Purification of the Photosynthetic Pigment C-phycocyanin from Heterotrophic Galdieria sulphuraria," J. Sci. Food Agric., 2013, 93, pp. 2933-2938.
Tabei et al., "Light-induced Gene Expression of Fructose 1, 6-bisphosphate Aldolase During Heterotrophic Growth in a Cyanobacterium, *Synechocystis* sp. PCC 6803," School of Lice Sciences, Tokyo University of Pharmacy and Life Sciences, Japan, Oct. 2008, doi: 10.1111/j. 1742-4658.2008.06772, FEBS Journal 276, 2009, pp. 187-198.
Tan et al., "Biomass Production and Fatty Acid Profile of a Scenedesmus rubescens-like Microalga," Bioresource Technology, 102, 2011, pp. 10131-10135.
Tan et al., "Screening of Diatoms for Heterotrophic Eicosapentaenoic Acid Production," Journal of Applied Phycology, 8, 1996, pp. 59-64.
Tanetani et al., "Action Mechanism of a Novel Herbicide, Fenoxasulfone," J. Pestic. Sci., 36, 3, 2011, pp. 357-362.
Tanoi et al., "Effects of Carbon Source on Growth and Morphology of Botryococcus Braunii," J. Appl. Phycol., 2011, 23, pp. 25-33.
Tejirian et al., "Inhibition of Enzymatic Cellulolysis by Phenolic Compounds," Enzyme and Microbial Technology, 48, 2011, pp. 239-247.
Thangaraj, "Isolation, Purification and Characterization of Photosynthetic Membrane Proteins from Galdieria Sulphuraria and Chlamydomonas Reinhardtii," A Dissertation Presented in Partial Fulfillment of the Requirements for the Degree Doctor in Philosophy, Approved Nov. 2010 by the Graduate Supervisory Committee, Arizona State University, Dec. 2010, 192 pages.
Thauer et al., "Biochemistry of Acetate Catabolism in an Aerobic Chemotrophic Bacteria," Annu. Rev. Microbiol., 1989, 43, pp. 43-67.
Theegala et al., "Contaminant Washout in a Hydraulically Integrated Serial Turbidostat Algal Reactor (HISTAR)," Aquacultural Engineering, 19, 1999, pp. 223-241.
Tillmann, "Kill and Eat Your Predator: A Winning Strategy of the Planktonic Flagellate Prymnesium Parvum," Aquatic Microbial Ecology, May 2003, vol. 32, pp. 73-84.
Tinh et al., "A Review of the Functionality of Probiotics in the Larviculture Food Chain," Marine Biotechnology, vol. 10, 2008, 12 pages.
Tischendorf et al., "Ultrastructure and Enzyme Complement of Proplastids from Heterotrophically Grown Cells of the Red Alga *Galdieria sulphuraria*," European Journal of Phycology, 2007, 42, 3, pp. 243-251, 10 pages, downloaded from http://www.tandfonline.com/loi/tejp20 on Dec. 28, 2012.
Tittel, et al., "Mixotrophs Combine Resource Use to Outcompete Specialists: Implications for Aquatic Food Webs," PNAS, Oct. 2003, vol. 100, No. 22, pp. 12776-12781.
Tong, et al., "Gas exchange between humans and multibiological life support system," Ecological Engineering 37 (2011) 2025-2034.
Tonon et al., "Long Chain Polyunsaturated Fatty Acid Production and Partitioning to Triacylglycerols in Four Microalgae," Phytochemistry, 61, 2002, pp. 15-24.
Toplin et al., "Biogeographic and Phylogenetic Diversity of Thermoacidophilic Cyanidiales in Yellowstone National Park, Japan and New Zealand," Applied and Environmental Microbiology, May 2008, vol. 74, No. 9, pp. 2822-2833.
Trabelsi et al., "Evaluation of Arthrospira platensis Extracellular Polymeric Substances Production in Photoautotrophic, Heterotrophic and Mixotrophic Conditions," Folia Microbiol., 2013, 58, pp. 39-45.
Tredici, et al. "Abstracts of Marine Biotechnology: Basics and Applications," Biomolecular Engineering, 20, 2003, pp. 37-82, 46 pages.
Tremblay et al., "Effect of Rhodomonas salina Addition to a Standard Hatchery Diet During the Early Ontogeny of the Scallop Pecten maximus," Aquaculture, 262, 2007, pp. 410-418.
Trenkamp et al., "Specific and Differential Inhibition of Very-long-chain Fatty Acid Elongases from *Arabidopsis thaliana* by Different Herbicides," PNAS, Aug. 2004, vol. 101, No. 32, pp. 11903-11908.
Tripathi et al., "Production of Astaxanthin in Haematococcus Pluvialis Cultured in Various Media," Bioresource Technology, 68, 1999, pp. 197-199.
Troxler, et al., "Heme Regulates Expression of Phycobiliprotein Photogenes in the Unicellular Rhodophyte, Cyanidium Caldarium," The Journal of Biological Chemistry, vol. 264, No. 34, Dec. 1989, pp. 20596-20601.
Tsavalos et al., "Development of Media for the Mixotrophic/heterotrophic Culture of Brachiomonas submarina," Journal of Applied Phycology, 6, 1994, pp. 431-433.
Ueda et al., "Bacterial Communities Constructed in Artificial Consortia of Bacteria and Chlorella vulgaris," Microbes Environ., vol. 25, No. 1, 2010, pp. 36-40.
Ueda et al., "Community Composition of Bacteria Co-cultivated with Microalgae in Non-axenic Algal Cultures," Microbiol. Cult. Coll., vol. 25, No. 1, 2009, pp. 21-25.
Ueno, et al., "Ethanol Production by Dark Fermentation in the Marine Green Alga, *Chlorococcum littorale*," Journal of Fermentation and Bioengineering, 1998, vol. 86, No. 1, pp. 38-43.
Valdez, et al., "Hydrothermal Liquefaction of *Nannochloropsis* sp.: Systematic Study of Process Variables and Analysis of the Product Fractions," Biomass and Bioenergy, SciVerse ScienceDirect, 46, 2012, pp. 317-331.
Van Baalen, et al., "Hetertrophic Growth of Blue-Green Algae in Dim Light," Journal of Bacteriology, Mar. 1971, vol. 105, No. 3, pp. 685-689.
Van Lis, et al., "Divergence of the Mitochondrial Electron Transport Chains from the Green alga *Chlamydomonas reinhardtii* and its Colorless Close Relative *Polytomella* sp.," Biochimica et Biophysica Acta, 1708, 2005, pp. 23-34.
Van Niel, et al., "Formation and Conversion of Oxygen Metabolites by *Lactococcus lactis* Subsp. *lactis* ATCC 19435 under Different Growth Conditions," Applied and Environmental Microbiology, Sep. 2002, vol. 68, No. 9, pp. 4350-4356.
Vandamme et al., "Flocculation of Chlorella vulgaris Induced by High pH: Role of Magnesium and Calcium and Practical Implications," Bioresource Technology, 105, 2012, pp. 114-119.
Vaquero et al., "Cu-mediated Biomass Productivity Enhancement and Lutein Enrichment of the Novel Microalga *Coccomyxa onubensis*," Process Biochemistry, 47, 2012, pp. 694-700.
Vazhappilly, et al., "Heterotrophic Production Potential of Omega-3 Polyunsaturated Fatty Acids by Microalgae and Algae-like Microorganisms," Botanica Marina vol. 41, 1998 pp. 553-558.
Verschuere et al., "Probiotic Bacteria as Biological Control Agents in Aquaculture," Microbiology and Molecular Biology Reviews, Dec. 2000, vol. 64, No. 4, pp. 655-671.
Videira et al., "Occurrence and Diversity of Nitrogen-fixing Sphingomonas Bacteria Associated with Rice Plants Grown in Brazil," FEMS Microbiol. Lett., 293, 2009, pp. 11-19.
Vine et al., "Probiotics in Marine Larviculture," FEMS Microbiol. Rev., 30, 2006, pp. 404-427.
Viso, et al., "Antibacterial and Antifungal Properties of Some Marine Diatoms in Culture," Botanica Marina vol. 30 pp. 41-45 1987.
Volkman et al., "Lipids in Marine Diatoms of the Genus *Thalassiosira*: Predominance of 24-Methylenecholesterol," Phytochemistry, 1988, vol. 27, No. 5, pp. 1389-1394.
Vonshak, "Mixotrophic Growth Modifies the Response of Spirulina (Arthrospira) Platensis (Cyanobacteria) Cells to Light," J. Phycol. 36, 2000, pp. 675-679.

(56) References Cited

OTHER PUBLICATIONS

Wagenen, et al., "Effects of Light and Temperature on Fatty Acid Production in Nannochloropsis Salina," Energies 2012, 5, pp. 731-740.
Walsh, "Effects of Herbicides on Photosynthesis and Growth of Marine Unicellular Algae," J. Hyacinth Control, 1972, 4 pages.
Wan et al., "The Effect of Mixotrophy on Microalgal Growth, Lipid Content, and Expression Levels of Three Pathway Genes in Chlorella Sorokiniana," Bioenergy and Biofuels, Applied Microbiol. Biotechnol. 2011, 91, pp. 835-844.
Wang, et al., "Mixotrophic Cultivation of Chlorella Pyrenoidosa with Diluted Primary Piggery Wastewater to Produce Lipids," Bioresource Technology, 104, 2012, pp. 215-220.
Wang et al., 'Growth-associated biosynthesis of astaxanthin in heterotrophic Chlorella zofingiensis (Chlorophyta) WJ Microbiol Biotechnol 2008, 24, 1915-1922.
Wang et al., "A Study on Lipid Production of the Mixotrophic Microalgae Phaeodactylum tricornutum on Various Carbon Sources," African Journal of Micribiology Research, vol. 6 (5), Feb. 2012, pp. 1041-1047.
Wang et al., "Effect of Organic Substance on the Growth of Porphyridium Cruentum," Microbiology, 2001, Abstract Only, 3 pages.
Wang et al., "Probiotics in Aquaculture: Challenges and Outlook," Aquaculture, 281, 2008, 4 pages.
Wang et al., "Structure of C-phycocyanin from Spirulina platensis at 2.2 Å Resolution: A Novel Monoclinic Crystal Form for Phycobiliproteins in Phycobilisomes," Acta Cryst., 2001, D57, pp. 784-792.
Warner et al., "The Impact of Shifts to Elevated Irradiance on the Growth and Photochemical Activity of the Harmful Algae Chattonella subsalsa and Prorocentrum minimum from Delaware," Harmful Algae, 6, 2007, pp. 332-342.
Watanabe et al., "Development of a Novel Artificial Medium Based on Utilization of Algal Photosynthetic Metabolites by Symbiotic Heterotrophs," Journal of Applied Microbiology, ISSN 1364-072, 105, 2008, pp. 741-751.
Watanabe et al., "Symbiotic Association in Chlorella Culture," FEMS Microbiology Ecology, 51, 2005, pp. 187-196.
Weeks, "Microalgae Growth on Crude Glycerol," retrieved from biogas.ifas.ufi.edu/internships/2011/files/kalvin.pdf on Oct. 18, 2013, 23 pages.
Wen et al., "Heterotrophic Production of Eicosapentaenoic Acid by Microalgae," Biotechnology Advances, 21, 2003, pp. 273-294.
Wen et al., "Production Potential of Eicosapentaenoic Acid by the Diatom Nitzschia Laevis," Biotechnology Letters, 22, 2000, pp. 727-733.
White et al., "The Genus Sphingomonas: Physiology and Ecology," Environmental Biotechnology, pp. 301-306.
Wikfors et al., "Growth of Post-set Oysters, Crassostrea virginica, on High-lipid Strains of Algal Flagellates tetraselmis spp.," Aquaculture, 143, 1996, pp. 411-419.
Wilcox et al., "Direct Catalytic Formation of Acetic Acid from CO2 and Methane," Catalysis Today, 88, 2003, pp. 83-90.
Williams et al., "Microalgae as Biodiesel & Biomass Feedstocks: Review & Analysis of the Biochemistry, Energetics & Economics," Energy & Environmental Science, 2010, 3, pp. 554-590, DOI: 10.1039/b924978h.
Wood et al., "A Challenge for 21st Century Molecular Biology and Biochemistry: What are the Causes of Obligate Autotrophy and Methanotrophy?," FEMS Microbiology Reviews, 28, 2004, pp. 335-352.
Wood et al., "Photoheterotrophy in the Production of Phytoplankton Organisms," Journal of Biotechnology, 70, 1999, pp. 175-183.
Wu et al., "The Feasibility of Biodiesel Production by Microalgae Using Industrial Wastewater," Bioresource Technology, 2012, 5 pages.

Xiong et al., "C-Tracer and Gas Chromatography-Mass Spectrometry Analysis Reveal Metabolic Flux Distribution in the Oleaginous Microalga Chlorella protothecoides," Plant Physiology, Oct. 2010, vol. 154, pp. 1001-1011.
Xiong et al., "Double CO2 Fixation in Photosynthesis-fermentation Model Enhances Algal Lipid Synthesis for Biodiesel Production," Bioresource Technology, 101, 2010, pp. 2287-2293.
Xiong et al., "High-density Fermentation of Microalga Chlorella protothecoides in Bioreactor for Microbio-diesel Production," Appl. Microbiol. Biotechnol., 2008, 78, pp. 29-36.
Xu et al., "Fumaric Acid Production in Saccharomyces cerevisiae by Simultaneous Use of Oxidative and Reductive Routes," Bioresource Technology, 148, 2013, pp. 91-96.
Xu et al., "Growth Characteristics and Eicosapentaenoic Acid Production by Nannochloropsis sp. in Mixotrophic Conditions," Biotechnology Letters, 2004, vol. 26, No. 1, pp. 51-53, Abstract Only, downloaded from http://www.springerlink.com/content/th5u146k85131452 on Jun. 1, 2012, 2 pages.
Yamada et al., "Electron Microscopic Studies of Chlorella ellipsoidea Protoplast Formation," Journal of General Microbiology, 1982, 128, pp. 1319-1327.
Yan et al., "Carbon Metabolism and Energy Conversion of Synechococcus sp. PCC 7942 Under Mixotrophic Conditions: Comparison with Photoautotrophic Condition," J. Appl. Phycol., May 2011, 12 pages.
Yang, et al., 'Energetics and Carbon Metabolism During Growth of Microalgal Cells under Photoautotrophic, Mixotrophic and Cyclic Light-Autotrophic/Dark-Heterotrophic Conditions,' Biochemical Engineering Journal 6, 2000, pp. 87-102.
Yang, et al., "Effects of Sodium Nitrate and Sodium Acetate Concentrations on the Growth and Fatty Acid Composition of Brachiomonas submarina," Journal of Ocean University of Qingdao (Oceanic and Coastal Sea Research) ISSN 1671-2463 Apr. 30, 2003 vol. 2 No. 1 pp. 75-78.
Yang et al., "Chronic Administration of Palmitoleic Acid Reduces Insulin Resistance and Hepatic Lipid Accumulation in KK-Ay Mice with Genetic Type 2 Diabetes," Lipids in Health and Disease, 2011,10:120, 8 pages.
Yang et al., "Composition and Physiological Effects of Sea Buckthorn (Hippophae) Lipids," Trends in Food Science & Technology, 13, 2002, pp. 160-167.
Yeh et al., "Effects of Cultivation Conditions and Media Composition on Cell Growth and Lipid Productivity of Indigenous Microalga Chlorella vulgaris ESP-31," Bioresource Technology, 105, 2012, pp. 120-127.
Yeh et al., "Hydrothermal Catalytic Production of Fuels and Chemicals from Aquatic Biomass," J. Chem. Technol. Biotechnol., 2013, 88, pp. 13-24.
Yeh et al., "pH-stat Photoheterotrophic Cultivation of Indigenous Chlorella Vulgaris ESP-31 for Biomass and Lipid Production Using Acetic Acid as the Carbon Source," Biochemical Engineering Journal, 64, 2012, 7 pages.
Yen et al., "The Comparison of Lutein Production by Scenesdesmus sp. In the Autotrophic and the Mixotrophic Cultivation," Applied Biochemistry and Biotechnology, vol. 164, No. 3, 2011, pp. 353-361, Abstract Only, 2 pages, retrieved from http://www.springerlink.com/content/p163056u2x271117 on Jun. 1, 2012.
Yl et al., "On-Station Trial of Different Fertilization Regimes Used in Bangladesh," Aquaculture CRSP 21st Annual Technical Report, Tenth Work Plan, Appropriate Technology Research 4 (10ATR4A) Final Report, Oregon State University, Corvallis, Oregon, 2004, pp. 197-206.
Yoon et al., "Effect of Palmitoleic Acid on Melanogenic Protein Expression in Murine B16 Melanoma," Journal of Oleo Science, 59(6), 2010, pp. 315-319.
Yoshimura et al., "Effective Utilization of Transmitted Light for Astaxanthin Production by Haematococcus Pluvialis," Journal of Bioscience and Bioengineering, vol. 102, No. 2, 2006, pp. 97-101.
You et al., "Ethanol Tolerance in the Yeast Saccharomyces cerevisiae is Dependent on Cellular Oleic Acid Content," Applied and Environmental Microbiology, Mar. 2003, vol. 69, No. 3, pp. 1499-1503.
Yu, "Effect of Mixed Carbon Substrate on Exopolysaccharide Production of Cyanobacterium Nostoc Flagelliforme in Mixotrophic Cultures," J. Appl. Phycol., 2012, 24, pp. 669-673.

(56) References Cited

OTHER PUBLICATIONS

Yu et al., "Growth and Physiological Features of *Cyanobacterium anabaena* sp. Strain PCC 7120 in a Glucose-Mixotrophic Culture," Biotechnology and Bioengineering, Chinese Journal of Chemical Engineering, 19(1), 2011, pp. 108-115.

Yu et al., "Growth Characteristics of the Cyanobacterium Nostac Flagelliforme in Photoautotrophic, Mixotrophic and Heterotrophic Cultivation," J. Appl. Phycol., 2009, 21, pp. 127-133.

Yu et al., "Triacylglycerol Accumulation and Profiling in the Model Diatoms Thalassiosira pseudonana and Phaeodactylum tricornutum (Baccilariophyceae) During Starvation," J. Appl. Phycol., 2009, 21, pp. 669-681.

Yue et al., "Hydrodynamics and Mass Transfer Characteristics in Gas-Liquid Flow Through a Rectangular Microchannel," Chemical Engineering Science, 62, 2007, pp. 2096-2108.

Yukino et al., "Incorporation of Exogenous Docosahexaenoic Acid into Triacylglycerols and Polar Lipids of Chlorella vulgaris," Journal of Oleo Science, 2005, vol. 54, No. 1, pp. 15-19.

Zaslavskaia et al., "Trophic Conversion of an Obligate Photoautotrophic Organism through Metabolic Engineering," Science, vol. 292, Jun. 2001, pp. 2073-2075.

Zhang, Cell Retention and Perfusion, Cell and Tissue Reactor Engineering, University of Minnesota, 2003, 28 pages.

Zhang et al., "Application of Mathematical Models to the Determination Optimal Glucose Concentration and Light Intensity for Mixotrophic Culture of Spirulina Platensis," Process Biochemistry, 34, 1999, pp. 477-481.

Zhang et al., "Kinetic Models for Astaxanthin Production by High Cell Density Mixotrophic Culture of the Microalga *Haematococcus pluvialis*," Journal of Industrial Microbiology & Biotechnology, 1999, 23, pp. 691-696.

Zhang et al., "Kinetic Models for Phycocyanin Production by High Cell Density Mixotrophic Culture of the Microalga *Spirulina platensis*," Journal of Industrial Microbiology & Biotechnology, 1998, 21, pp. 283-288.

Zhang et al., "Mixotrophic Cultivation of Botryococcus Braunii," Biomass and Bioenergy, ScienceDirect, 35, 2011, pp. 1710-1715.

Zheng, et al., "Large-Scale Production of Astaxanthin by Xanthophyllomyces Dendrorhous," Institution of Chemical Engineers, Trans IChemE, Part C, Jun. 2006, Food and Bioproducts Processing, 84(C2), pp. 164-166.

Zheng et al., "Effects of Inoculated Microcoleus vaginatus on the Structure and Function of Biological Soil Crusts of Desert," Biol. Fertil. Soils, 2011, 47, pp. 473-480.

Zheng et al., "Two-stage Heterotrophic and Phototrophic Culture Strategy for Algal Biomass and Lipid Production," Bioresource Technology, 103, 2012, pp. 484-488.

Zhou et al., "A Hetero-Photoautotrophic Two-Stage Cultivation Process to Improve Wastewater Nutrient Removal and Enhance Algal Lipid Accumulation," Bioresource Technology, 110, 2012, pp. 448-455.

Zhu et al., "Scale-Up Potential of Cultivating Chlorella Zofingiensis in Piggery Wastewater for Biodiesel Production," Bioresource Technology, 137, 2013, pp. 318-325.

Zhuang et al., "Mixotrophic and Heterotrophic Growth of Haematococcus Pluvialis," Microbiology, 2000, Abstract Only, 4 pages.

Zijffers. J.W. F. et al., 'Maximum Photosynthetic Yield of Green Microalgae in Photobioreactors,' Mar Biotechnol (2010) 12:708-718.

Zinniel et al., "Isolation and Characterization of Endophytic Colonizing Bacteria from Argonomic Crops and Prairie Plants," Applied and Environmental Microbiology, May 2002, vol. 68, No. 5, pp. 2198-2208.

Zittelli et al., "Production of Eicosapentaenoic Acid by *Nannochloropsis* sp. Cultures in Outdoor Tubular Photobioreactors," Journal of Biotechnology, 70, 1999, pp. 299-312.

Auxostat. pH auxostat. www.rpi.edu. 2009:1.

Nasir Kureshy, D. Allen Davis, and C.R. Arnold, Effect of Ozone Treatment on Cultures of Nannochloropsis oculata, Isochrysis galbana, and Chaetoceros gracilis, Journal of the World Aquacufture Society, vol. 30, No. 4, Dec. 1999, pp. 473-180.

Germond, et al, "The Phylogenetic position and phenotypic changes of a Chlorella-like alga during 5-year microcosm culture", Eur. J. Phycol (2013), 48(4): 485-496.

Heeg, et al, "ITS2 and 18S rDNA sequence-structure phylogeny of Chlorella and allies (Chlorophyta, Trebouxiophyceae, Chlorellaceae)", Elsevier, Plant Gene 4 (2015) 20-28.

Ogbonna, et al, "Night Biomass Loss and Changes in Biochemical Composition of Cells during Light/Dark Cyclic Culture of Chlorella pyrenoidosa", vol. 82, No. 6, 558-564. 1996.

Ogbonna, et al, "Sequential heterotrophic/autrotrophic cultivation—An efficient method of producing Chlorella biomass for health food and animal feed" 9: 359-366, 1997.

Miron, et al, "Comparative evaluation of compact photobioreactors for large-scale monoculture of microalgae," Journal of Biotechnology 70 (1999) 249-270.

Santek, et al, "Horizontal Tubular Bioreactors in Biotechnology," Chem. Biochem. Eng. Q. 20 (4) 389-399 (2006).

Chisti, "Large-Scale Production of Algal Biomass: Raceway Ponds," Algae Biotechnology, 21-40 (2016).

BALANCED MIXOTROPHY METHOD

CROSS REFERENCE TO RELATED APPLICATIONS

This application is a continuation of International Application No. PCT/US2013/069047, filed Nov. 8, 2013 entitled Balanced Mixotrophy Methods, which claims benefit of U.S. Provisional Application No. 61/724,710, filed Nov. 9, 2012, entitled Methods of Culturing Microorganisms in Mixotrophic Conditions; U.S. Provisional Application No. 61/798,969, filed Mar. 15, 2013, entitled Mixotrophy Systems and Methods; and U.S. Provisional Application No. 61/891,990, filed Oct. 17, 2013, entitled Balanced Mixotrophy Methods, the entire contents of which are hereby incorporated by reference herein.

BACKGROUND

Mixotrophic microorganism, such as microalgae and cyanobacteria, may be cultivated to produce proteins, lipids, carbohydrates, pigments, and polysaccharides that are useful in a variety of products. The metabolism of mixotrophic microorganisms includes both phototrophic and heterotrophic metabolisms to utilize multiple inputs as energy and carbon for growth and production of gases. When light is utilized as an energy source and inorganic carbon (e.g., carbon dioxide) is utilized as a carbon source by the phototrophic metabolism for growth, the microorganism's net oxygen production is positive and carbon dioxide is consumed. When an organic carbon source is utilized as both an energy source and a carbon source by the heterotrophic metabolism for growth, the microorganism's net carbon dioxide production is positive and oxygen is consumed. With the production and consumption of oxygen and carbon dioxide alternating or happening simultaneously within a mixotrophic microorganism, the composition of gasses saturated in the culture medium is continually changing.

Using conventional air sparging and carbon dioxide injection in a mixotrophic culture does not maintain a correct balance of gases for efficient growth in a continually changing culture. The gas imbalance created by conventional air sparging and carbon dioxide injection in a mixotrophic culture may result in gases being lost to the atmosphere before utilization by the microorganisms in the aqueous medium, which reduces the method efficiency and wastes resources. Toxic saturation of a gas in the culture medium may also occur, which may provide an inhibiting effect on the growth of the mixotrophic microorganisms. The use of air sparging may also create foam (comprised of proteins, polysaccharides, carbon and other organics), which can facilitate the proliferation of contaminating organisms (e.g., bacteria, fungi and predators) by harboring the contaminating organisms and providing a feed source for the contaminating organisms. The foam may also block or limit light available for photosynthesis. Both the facilitation of contaminating organisms and blocking of light may inhibit the growth of the mixotrophic microorganisms. Another drawback of systems using conventional air sparging and carbon dioxide injection is the need to supply gasses from an external source to bioreactors, which may reduce the length of each run of a bioreactor circulation path or require additional gas injection points, thus potentially limiting the volumetric capacity of the bioreactor. The additional gas injection points may also increase the costs of constructing and operating the bioreactor.

Therefore, there is a need in the art for a method of culturing mixotrophic microorganisms which efficiently utilizes carbon dioxide and oxygen, and reduces the accumulation of foam in the culture.

SUMMARY

Embodiments described herein relate generally to methods for culturing mixotrophic microorganisms in a state of balanced gas composition. Parameters of a culture of mixotrophic microorganisms may be controlled to reduce the requirements of externally supplied gases and optimize the production and consumption of gases within the culture by the phototrophic and heterotrophic metabolisms of the mixotrophic microorganisms.

In some embodiments of the invention, a method of growing mixotrophic culture of microorganisms comprises: circulating a culture of mixotrophic microorganisms in an aqueous culture medium through a circulation path of a bioreactor system comprising at least one light source supplying light and at least one organic carbon supply device supplying organic carbon to the culture of mixotrophic microorganisms; detecting at least one parameter of the culture of mixotrophic microorganisms selected from the group consisting of: pH, dissolved oxygen, and dissolved carbon dioxide, with at least one sensor; transmitting data from the at least one sensor to a programmable logic control system (PLC), wherein the PLC controls the supply of at least one selected from the group consisting of light and organic carbon to the culture of mixotrophic microorganisms; and continuously adjusting the supply of at least one selected from the group consisting of light and organic carbon to the culture through the PLC based on the sensor data to maintain the at least one selected from the group consisting of the pH, dissolved oxygen, and dissolved carbon dioxide levels of the culture at a predetermined threshold level.

In some embodiments, the organic carbon is supplied to the culture when the dissolved oxygen level is above a predetermined threshold level. In some embodiments, the predetermined threshold level of dissolved oxygen is between 25-200% of the saturation level of the aqueous culture. In some embodiments, an acidic organic carbon is supplied to the culture when the pH level is above the predetermined threshold level. In some embodiments, a basic organic carbon is administered to the culture when the pH level is below the predetermined threshold level. In some embodiments, the predetermined threshold pH level is between 6 and 9. In some embodiments, the predetermined threshold pH level is between 1 and 5. In some embodiments, the organic carbon is supplied to the culture when the dissolved carbon dioxide level is below the predetermined threshold level.

In some embodiments, the method further comprises supplying gas to the culture of mixotrophic microorganisms with at least one gas supply device, and wherein the PLC controls the supply of gas. In some embodiments, the gas may comprise carbon dioxide, oxygen, air, or nitrogen. In some embodiments, the carbon dioxide is supplied to the culture when the dissolved oxygen level is below the predetermined threshold level. In some embodiments, the carbon dioxide is supplied to the culture when the pH level is above the predetermined threshold level. In some embodiments, the gas is supplied at a plurality of locations along the circulation path of the bioreactor system.

In some embodiments, the organic carbon is supplied at a plurality of locations along the circulation path of the bioreactor system. In some embodiments, the light is supplied at a plurality of locations along the circulation path of the bioreactor system. In some embodiments, the method further comprises harvesting the mixotrophic microorganisms from the bioreactor system.

In some embodiments, controlling the at least one light source comprises adjusting at least one selected from the group consisting of: amount of light, photoperiod of light, flashing or pulsing period of light, wavelength of light, and intensity of light. In some embodiments, at least one of an amount and intensity of light is increased when the detected dissolved oxygen level is below the predetermined threshold level. In some embodiments, at least one of an amount and intensity of light is decreased when the detected dissolved oxygen level is above the predetermined threshold level.

In some embodiments, the organic carbon comprises at least one selected from the group consisting of: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, and yeast extract.

In some embodiments of the invention, a method of growing a mixotrophic culture of microorganisms comprises: circulating a culture of mixotrophic microorganisms in an aqueous culture medium through a circulation path of a bioreactor system comprising at least one light source for supplying the light, at least one carbon dioxide supply device for supplying carbon dioxide, and at least one organic carbon supply device for supplying organic carbon to the culture of mixotrophic microorganisms; detecting dissolved oxygen and pH levels of the culture of mixotrophic microorganisms with sensors; transmitting data from the sensors to a programmable logic control system (PLC), wherein the PLC controls the supply of carbon dioxide and organic carbon to the culture of mixotrophic microorganisms; and continuously adjusting the supply of at least one selected from the group consisting of carbon dioxide and organic carbon to the culture of mixotrophic microorganisms through the PLC based on the sensor data to maintain the at least one selected from the group consisting of the pH and dissolved oxygen levels of the culture at a predetermined threshold level.

In some embodiments, the supply of carbon dioxide and organic carbon is decreased when the pH level is below the predetermined threshold level. In some embodiments, the supply of carbon dioxide is increased when the pH level is above the predetermined threshold level and the dissolved oxygen level is below the predetermined threshold level. In some embodiments, the supply of organic carbon is increased when the pH level is above the predetermined threshold level and the dissolved oxygen level is above the predetermined threshold level. In some embodiments, the organic carbon is acetic acid.

DESCRIPTION OF THE INVENTION

Definitions

Figure 1:
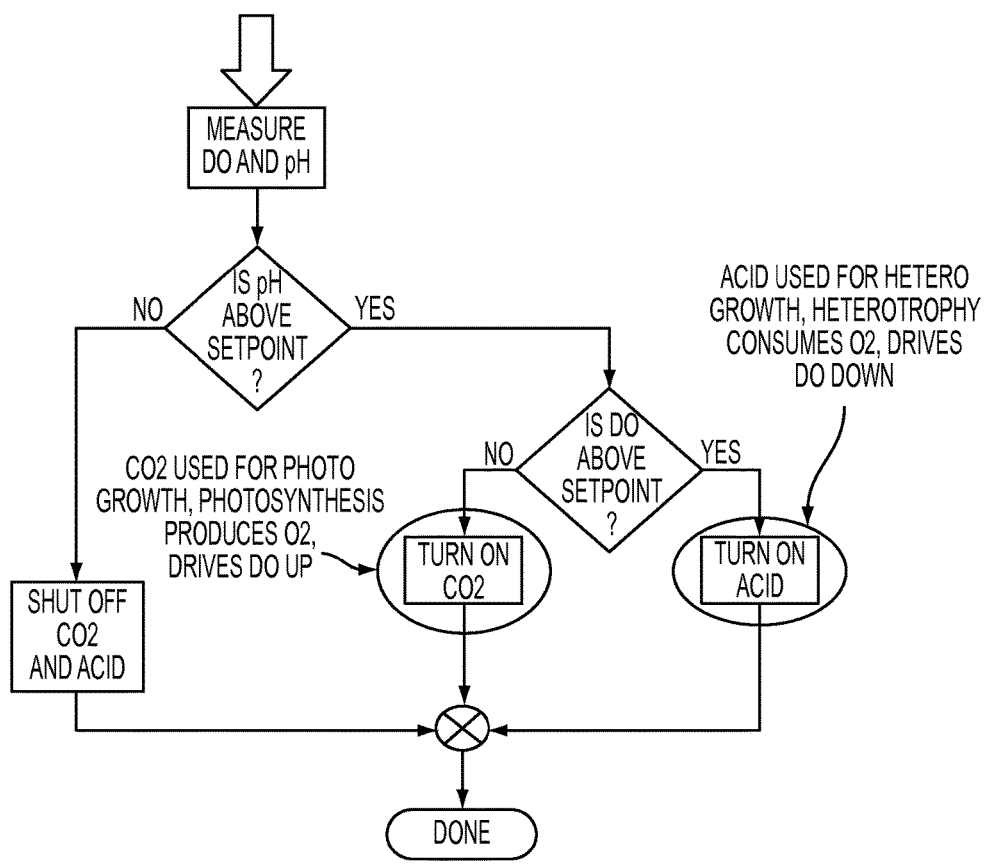
FIG. 1 shows a flow chart for controlling the balance of gases in a culture of microorganisms.

The term "microorganism" refers to microscopic organisms such as microalgae and cyanobacteria. Microalgae include microscopic multi-cellular plants (e.g. duckweed), photosynthetic microorganisms, heterotrophic microorganisms, diatoms, dinoflagelattes, and unicellular algae.

The terms "microbiological culture", "microbial culture", or "microorganism culture" refer to a method or system for multiplying microorganisms through reproduction in a predetermined culture medium, including under controlled laboratory conditions. Microbiological cultures, microbial cultures, and microorganism cultures are used to multiply the organism, to determine the type of organism, or the abundance of the organism in the sample being tested. In liquid culture medium, the term microbiological, microbial, or microorganism culture generally refers to the entire liquid medium and the microorganisms in the liquid medium regardless of the vessel in which the culture resides. A liquid medium is often referred to as "media", "culture medium", or "culture media". The act of culturing is generally referred to as "culturing microorganisms" when emphasis is on plural microorganisms. The act of culturing is generally referred to as "culturing a microorganism" when importance is placed on a species or genus of microorganism. Microorganism culture is used synonymously with culture of microorganisms.

Microorganisms that may grow in mixotrophic culture conditions include microalgae, diatoms, and cyanobacteria. Non-limiting examples of mixotrophic microorganisms may comprise organisms of the genera: *Agmenellum, Amphora, Anabaena, Anacystis, Apistonema, Pleurochyrsis, Arthrospira (Spirulina), Botryococcus, Brachiomonas, Chlamydomonas, Chlorella, Chloroccum, Cruciplacolithus, Cylindrotheca, Coenochloris, Cyanophora, Cyclotella, Dunaliella, Emiliania, Euglena, Extubocellulus, Fragilaria, Galdieria, Goniotrichium, Haematococcus, Halochlorella, Isochyrsis, Leptocylindrus, Micractinium, Melosira, Monodus, Nostoc, Nannochloris, Nannochloropsis, Navicula, Neospongiococcum, Nitzschia, Odontella, Ochromonas, Ochrosphaera, Pavlova, Picochlorum, Phaeodactylum, Pleurochyrsis, Porphyridium, Poteriochromonas, Prymnesium, Rhodomonas, Scenedesmus, Skeletonema, Spumella, Stauroneis, Stichococcus, Auxenochlorella, Cheatoceros, Neochloris, Ocromonas, Porphiridium, Synechococcus, Synechocystis, Tetraselmis, Thraustochytrids, Thalassiosira*, and species thereof.

The organic carbon sources suitable for growing a microorganism mixotrophically or heterotrophically may comprise: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, yeast extract, and combinations thereof. The organic carbon source may comprise any single source, combination of sources, and dilutions of single sources or combinations of sources.

The terms "mixotrophic" and "mixotrophy" refer to culture conditions in which light, organic carbon, and inorganic carbon (e.g., carbon dioxide, carbonate, bi-carbonate) may be applied to a culture of microorganisms. Microorganisms capable of growing in mixotrophic conditions have the metabolic profile of both phototrophic and heterotrophic microorganisms, and may use both light and organic carbon as energy sources, as well as both inorganic carbon and organic carbon as carbon sources. A mixotrophic microorganism may be using light, inorganic carbon, and organic carbon through the phototrophic and heterotrophic metabolisms simultaneously or may switch between the utilization of each metabolism. A microorganism in mixotrophic culture conditions may be a net oxygen or carbon dioxide producer depending on the energy source and carbon source utilized by the microorganism. Microorganisms capable of mixotrophic growth comprise microorganisms with the natural metabolism and ability to grow in mixotrophic conditions, as well as microorganisms which obtain the metabolism and ability through modification of cells by way of methods such as mutagenesis or genetic engineering.

The terms "phototrophic", "phototrophy", "photoautotrophy", "photoautotrophic", and "autotroph" refer to culture conditions in which light and inorganic carbon (e.g., carbon dioxide, carbonate, bi-carbonate) may be applied to a culture of microorganisms. Microorganisms capable of growing in phototrophic conditions may use light as an energy source and inorganic carbon (e.g., carbon dioxide) as a carbon source. A microorganism in phototrophic conditions may produce oxygen.

The terms "heterotrophic" and "heterotrophy" refer to culture conditions in which organic carbon may be applied to a culture of microorganisms in the absence of light. Microorganisms capable of growing in heterotrophic conditions may use organic carbon as both an energy source and as a carbon source. A microorganism in heterotrophic conditions may produce carbon dioxide.

The term "axenic" describes a culture of an organism that is entirely free of all other "contaminating" organisms (i.e., organisms that are detrimental to the health of the microalgae or cyanobacteria culture). Throughout the specification, axenic refers to a culture that when inoculated in an agar plate with bacterial basal medium, does not form any colonies other than the microorganism of interest. Axenic describes cultures not contaminated by or associated with any other living organisms such as but not limited to bacteria, cyanobacteria, microalgae and/or fungi. Axenic is usually used in reference to pure cultures of microorganisms that are completely free of the presence of other different organisms. An axenic culture of microalgae or cyanobacteria is completely free from other different organisms.

Bacteria that may be present in cultures of microalgae and cyanobacteria comprise, but are not limited to: *Achromobacter* sp., *Acidovorax* sp., *Acinetobacter* sp., *Aeromonas* sp., *Agrobacterium* sp., *Alteromonas* sp., *Ancylobacter* sp., *Aquaspirillum* sp., *Azospirillum* sp., *Azotobacter* sp., *Bacillus* sp., *Bergeyella* sp., *Brevundimonas* sp., *Brochothrix* sp., *Brumimicrobium* sp., *Burkholderia* sp., *Caulobacter* sp., *Cellulomonas* sp., *Chryseobacterium* sp., *Curtobacterium* sp., *Delftia* sp., *Empedobacter* sp., *Enterobacter* sp., *Escherichia* sp., *Flavobacterium* sp., *Gemmatimonas* sp., *Halomonas* sp., *Hydrogenophaga* sp., *Janthinobacterium* sp., *Lactobacillus* sp., *Marinobacter* sp., *Massilia* sp., *Microbacterium* sp., *Myroides* sp., *Pantoea* sp., *Paracoccus* sp., *Pedobacter* sp., *Phaeobacter* sp., *Phyllobacterium* sp., *Pseudoalteromonas* sp., *Pseudomonas* sp., *Rahnella* sp., *Ralstonia* sp., *Rhizobium* sp., *Rhodococcus* sp., *Roseomonas* sp., *Sphingobacterium* sp., *Sphingomoas* sp., *Staphylococcus* sp., *Stenotrophomonas* sp., *Vibrio* sp., and *Zobelliae* sp.

Bacteria that have a negative or harmful effect on the microalgae and cyanobacteria may be designated as contaminating bacteria. The bacteria that may have a negative or harmful effect on microalgae or cyanobacteria in a culture comprise, but are not limited to: *Achromobacter* sp., *Acidovorax* sp., *Aeromonas* sp., *Agrobacterium* sp., *Alteromonas* sp., *Aquaspirillum* sp., *Azospirillum* sp., *Azotobacter* sp., *Bergeyella* sp., *Brochothrix* sp., *Brumimicrobium* sp., *Burkholderia* sp., *Caulobacter* sp., *Cellulomonas* sp., *Chryseobacterium* sp., *Curtobacterium* sp., *Delftia* sp., *Empedobacter* sp., *Enterobacter* sp., *Escherichia* sp., *Flavobacterium* sp., *Marinobacter* sp., *Microbacterium* sp., *Myroides* sp., *Paracoccus* sp., *Pedobacter* sp., *Phaeobacter* sp., *Pseudoalteromonas* sp., *Pseudomonas* sp., *Rahnella* sp., *Ralstonia* sp., *Rhizobium* sp., *Rhodococcus* sp., *Roseomonas* sp., *Staphylococcus* sp., *Stenotrophomonas* sp., *Vibrio* sp., *Zobelliae* sp. and other bacteria which share similar characteristics.

The bacteria that may have a neutral or beneficial effect on microalgae or cyanobacteria in a culture comprise, but are not limited to: *Acidovorax* sp., *Acinetobacter* sp., *Aeromonas* sp., *Agrobacterium* sp., *Alteromonas* sp., *Ancylobacter* sp., *Azospirillum* sp., *Azotobacter* sp., *Bacillus* sp., *Brevundimonas* sp., *Brumimicrobium* sp., *Burkholderia* sp., *Caulobacter* sp., *Cellulomonas* sp., *Delftia* sp., *Empedobacter* sp., *Gemmatimonas* sp., *Halomonas* sp., *Hydrogenophaga* sp., *Janthinobacterium* sp., *Lactobacillus* sp., *Marinobacter* sp., *Pantoea* sp., *Paracoccus* sp., *Phaeobacter* sp., *Phyllobacterium* sp., *Pseudoalteromonas* sp., *Pseudomonas* sp., *Rhizobium* sp., *Sphingomoas* sp., *Zobelliae* sp. and other bacteria which share similar characteristics. While bacteria in a particular genus generally have the same characteristics, it is recognized that a genus of bacteria with the majority of species generally identified as harmful to microalgae or cyanobacteria may also include a particular species within the genus which is neutral or beneficial to a specific culture of microalgae or cyanobacteria, and vice versa. For example, many species of *Pseudomonas* have been observed to be harmful to microalgae, however literature has described certain species of *Pseudomonas* with anti-fungal functionality which may be beneficial to a culture of microalgae or cyanobacteria.

The term "pH auxostat" refers to the microbial cultivation technique that couples the addition of fresh medium (e.g., medium containing organic carbon or acetic acid) to pH control. As the pH drifts from a given set point, fresh medium is added to bring the pH back to the set point. The rate of pH change is often an excellent indication of growth and meets the requirements as a growth-dependent parameter. The feed will keep the residual nutrient concentration in balance with the buffering capacity of the medium. The pH set point may be changed depending on the microorganisms present in the culture at the time. The microorganisms present may be driven by the location and season where the bioreactor is operated and how close the cultures are positioned to other contamination sources (e.g., other farms, agriculture, ocean, lake, river, waste water). The rate of medium addition is determined by the buffering capacity and the feed concentration of the limiting nutrient and not directly by the set point (pH) as in a traditional auxostat. The pH auxostat is robust but controls nutrient concentration indirectly. The pH level represents the summation of the production of different ionic species and ion release during carbon and nutrient uptake. Therefore the pH level can move either up or down as a function of growth of the microorganisms. The most common situation is pH depression caused by organic acid production and ammonium uptake. However, for microorganisms growing on protein or amino acid-rich media, the pH level will rise with growth because of the release of excess ammonia.

The term "harvesting" refers to removing the culture of microorganisms from the culturing vessel and/or separating the microorganisms from the culture medium. Harvesting of microorganisms may be conducted by any method known in the art such as, but not limited to, skimming, draining, dissolved gas flotation, foam fractionation, centrifugation, filtration, sedimentation, chemical flocculation, and electro-dewatering.

Balanced Mixotrophy Overview

A bioreactor system operating in a state which continuously balances the composition of gases may provide numerous benefits to a culture of mixotrophic microorganisms, such as microalgae and cyanobacteria. By balancing the oxygen and carbon dioxide levels in a mixotrophic culture continuously, the gas exchange may be optimized to: increase the efficiency of organic carbon use in the microorganism culture; reduce the amount of foam in the bioreactor system; reduce the amount of gases lost in the culture by bubbling out of the aqueous medium before the gases are utilized by the microorganisms; reduce the amount of gas supplied by external sources; and reduce the microorganisms growth inhibiting effects caused by toxic oversaturation of gases in the culture medium. Through the optimization provided by a mixotrophic culturing method continuously balancing the gas composition, the combined effects may result in an increase in efficiency in gas and organic carbon utilization. Increased efficiency in gas and organic carbon utilization may reduce overall costs of the culturing process and improve growth or culture health.

Continually balancing the gas composition of a mixotrophic culture may also allow the system to exchange gases as the culture circulates in the bioreactor system without the use of a de-gassing tank (i.e., tank where excess gases are removed from a culture medium), or substantially reduce the amount of foam created in the de-gassing tank and bioreactor system. The elimination of a de-gassing tank may reduce the cost of the bioreactor system and simplify the circulation path. The reduction of foam may reduce the level of contaminating organisms in the culture. Continuously balancing the gas composition of a mixotrophic culture may also allow for the reduction in the gas supplied by an external source, or the elimination of the external gas input, with the microorganisms solely using the oxygen and carbon dioxide produced by the phototrophic and heterotrophic metabolisms. Additionally, continuously balancing the gas composition and pH of a culture will allow the bioreactor system to have a larger volume and longer circulation path for the aqueous culture. Through the supply of light, organic carbon, and optionally some carbon dioxide to continuously adjust the culture conditions, the mixotrophic microorganisms in the culture may shift between the use of phototrophic and heterotrophic metabolisms to maintain a balanced gas composition and pH level.

A method of continuously balancing the gas composition of a culture of a single species of mixotrophic microorganisms may be distinguished from other culturing methods which co-culture two different microorganisms in a symbiotic relationship with the co-culture comprising one microorganism being phototrophic and one microorganism being heterotrophic. A co-culture of different microorganisms introduces the complexity of managing two different organisms which may differ in a variety of aspects such as growth rate, nutrient consumption rate, shear sensitivity, and preferred culture parameters (e.g., pH, temperature, salinity, light exposure). Also, the fluctuation of any of these aspects in a symbiotic co-culture may cause the balance between the microorganisms to be upset and the decline of both microorganism species.

For example, if the conditions in the co-culture change to favor the phototrophic microorganisms, the proliferation of the phototrophic microorganisms may deplete resources for the heterotrophic microorganisms and produce a toxic level of saturated oxygen which inhibits the functions of the phototrophic microorganisms. In a method of continuously balancing the gas composition of a culture of a single species of mixotrophic microorganism, the culture conditions only have to be tailored for a single microorganism type, which allows the mixotrophic microorganisms to better cope with fluctuations in the culture conditions and maximize the available inputs for optimal growth or product accumulation.

A method of continuously balancing the gas composition of a culture of a single species of mixotrophic microorganism may also be distinguished from other methods in which a culture of microorganisms are cultured in defined sequential periods of phototrophic conditions and heterotrophic conditions. When a culture of microorganisms is cultured in defined sequential stages of phototrophy and heterotrophy, the system still has to supply gases (e.g., oxygen, carbon dioxide) from an external source for consumption by the microorganisms. Also, the sequential culturing of the microorganisms in different culture conditions may cause the microorganism to go into a lipid maturation or other product accumulation stage when in heterotrophic conditions for a sustained period of time due to the stress of changing culture conditions. In a method of continuously balancing the gas composition of a culture of a single species of mixotrophic microorganism, the amount of gases supplied by external sources may be reduced or eliminated by consuming gases produced by the mixotrophic microorganisms. Continually balancing the gas composition may also maintain a longer growth phase (i.e., cell division to increase the cell count of the culture) while utilizing both the phototrophic and heterotrophic metabolisms.

System

In some embodiments, a bioreactor system for growing mixotrophic microorganisms in an aqueous culture medium may comprise a culturing vessel, at least one light source, at least one organic carbon supply device, at least one sensor, and a programmable logic control system (PLC). In some embodiments, the bioreactor system may further comprise at least one gas supply device such as, but not limited to, a carbon dioxide, oxygen, nitrogen, or air injection or bubbling device as known in the art. In some embodiments, the system may comprise additional nutrient supply devices as known in the art for nutrients such as, but not limited to, nitrates, micronutrients, macronutrients, phosphates, and trace metals. The culturing vessel may comprise any suitable open or closed vessel capable of axenic or non-axenic microorganism culture growth such as, but not limited to, a tank, a column bioreactor, a trough, a tubular bioreactor, a flat panel bioreactor, a bag bioreactor, a pond, and a raceway pond. In some embodiments, the bioreactor system may further comprise a heat exchanger for adjusting the temperature of the culture such as but not limited to, heating or cooling coils, or a shell and tube heat exchanger.

In some embodiments, the light source may comprise natural light (e.g., sunlight), at least one artificial lighting device, or combinations thereof. The at least one artificial lighting device may comprise any artificial lighting device capable of supplying light to a culture of microorganisms such as, but not limited to, fluorescent tubes, light emitting diodes (LED), micro LEDs, high pressure sodium lamps, high intensity discharge lamps, neon lamps, metal vapor lamps, halogen lamps, sulfur plasma lamps, and incandescent bulbs. In some embodiments, the at least one artificial lighting device may be selected or tuned to provide light of a particular wavelength spectrum or combination of spectrums such as, but not limited to, violet (about 380-450 nm), blue (about 450-495 nm), green (about 495-570 nm), yellow (about 570-590 nm), orange (about 590-620 nm), red (about 620-750 nm), and far red (about 700-800 nm), infrared (IR) (about 1,000-20,000 nm) and ultraviolet (UV) (about 10-400 nm).

In some embodiments, the supply of light may be continuous, discontinuous, flashing, or pulsing to create any desired light/dark cycle. In some embodiments, the intensity of light supplied by the at least one artificial lighting device may comprise a constant intensity or varying intensities. In some embodiments, the lighting may comprise narrow band LED lighting with intensities from 100-10,000 µmol photon/$m^2$ s, and wavelengths or combinations of wavelengths between 300-800 nm. In some embodiments, the natural light may be filtered or partially blocked before reaching the culture of microorganisms to control the amount, intensity, or wavelength of light.

The at least one sensor may comprise at least one selected from the group consisting of optical density, turbidity, dissolved oxygen, dissolved carbon dioxide, temperature, light (i.e., photodetector), photosynthetically active radiation (PAR), and pH sensors. The at least one sensor may monitor and detect conditions in the mixotrophic culture and transmit the data to the PLC. The PLC system may comprise any controller and computer system known in the art capable of controlling actuators and valves. The PLC may use the detected culture data to control at least one from the group consisting of: the organic carbon supply device, at least one artificial lighting device, a light filter or shade, additional nutrient supply device, and a gas supply device. In the alternative, an operator may manually control the supply of organic carbon, light, and/or gases based on the detected parameters and sensor data. In other embodiments, the system may be run stoichiometrically without any sensors based off of the estimated culture density, amount of light supplied, the amount of gas supplied (e.g., oxygen, carbon dioxide), and/or the amount and type of organic carbon source supplied.

The at least one organic carbon supply device may comprise a metering, dosing, or injection device as is known in the art. In some embodiments, the organic carbon source may be in a concentrated form. In some embodiments, the organic carbon source may be in a diluted form. In some embodiments, the organic carbon source may be a combination of at least two different organic carbon sources.

In some embodiments, the at least one organic carbon supply, at least one gas supply device, and/or at least one artificial lighting device may comprise a plurality of devices strategically located along the circulation path of the aqueous culture through the bioreactor system. With multiple locations to add light, organic carbon and/or gases, the bioreactor system may maintain more finely tuned control over the gas exchange and pH within the culture as compared to a bioreactor system with a single supply point of light, organic carbon and/or gases.

The aqueous culture medium may be circulated through the bioreactor system with a paddle wheel, pump, jets, thrusters, gravity, or any other known means. The velocity at which the aqueous culture medium is circulated may be adjusted to provide a desired level of turbulence in the circulating aqueous culture medium and residence time in the bioreactor system.

Method

In one non-limiting exemplary method, a culture of mixotrophic microorganisms, such as microalgae and cyanobacteria, in an aqueous culture medium may be circulated through a circulation path of a bioreactor system comprising at least one light source for supplying light, at least one organic carbon supply device for supplying organic, and at least one sensor for detecting a parameter of the culture. The aqueous culture medium may comprise water and micronutrients (e.g., salts, trace metals, nitrates, phosphates) in a formulation specific for the microorganism species. During the circulation of the culture, at least one culture parameter from the group consisting of the optical density, turbidity, pH, dissolved oxygen, and dissolved carbon dioxide levels of a culture of mixotrophic microorganisms in an aqueous medium may be detected by the at least one sensor. The at least one culture parameter detected by the at least one sensor may be transmitted to a programmable logic control system (PLC), wherein the PLC controls the supply of at least one from the group consisting of light and organic carbon to the culture through the at least one light source and at least one organic carbon supply device. The PLC may continuously adjust the supply of at least one from the group consisting of light and organic carbon to the culture to maintain the at least one detected culture parameter at a predetermined threshold level. Maintenance of the culture parameters within a range of the predetermined threshold levels may reduce or eliminate the need for the external supply of gases, and optimize the production and consumption of oxygen and carbon dioxide by the mixotrophic microorganisms to achieve a balanced gas composition.

In some embodiments, the bioreactor system may further comprise at least one gas supply device which may also be controlled by the PLC to maintain the at least one detected culture parameter at a predetermined threshold level. In some embodiments, the gas may comprise carbon dioxide, oxygen, nitrogen, air, or combinations thereof. In some embodiments, no gas is injected or supplied. In some embodiments, the light may be controlled by controlling a filter or shade which partially blocks natural light to reduce the amount, intensity, or wavelength spectrum of the light. In some embodiments, the supply of light comprises controlling at least one aspect such as the amount of light, photoperiod of light, flashing or pulsing period of light, wavelength range of light, and intensity of light.

In some embodiments, the culture of mixotrophic microorganisms may be axenic and maintained in axenic conditions within the bioreactor system. In some embodiments, the culture of mixotrophic microorganisms may be non-axenic and is not maintained in axenic conditions within the bioreactor system. In some embodiments, the pH predetermined threshold level or set point may be between 6 and 9, or in other embodiments between 1 and 5. In some embodiments, the dissolved oxygen level predetermined threshold level or set point may be between about 0.1 mg $O_2$/L to about 30 mg $O_2$/L depending on bacterial population and species, as well as mixotrophic microorganism population and species. In further embodiments, the predetermined threshold level of dissolved oxygen may be between 1 mg $O_2$/L and 6 mg $O_2$/L. In some embodiments, the culture may balance the oxygen and carbon dioxide levels at the saturation point of the culture medium. In some embodiments, the predetermined threshold level of dissolved oxygen may be 25-200% of the saturation level of the aqueous culture medium. The predetermined threshold level of carbon dioxide may comprise 25-500% of the saturation level of the aqueous culture medium.

In some embodiments, the organic carbon, gas, or light may be supplied at multiple locations along the circulation path of the aqueous culture of mixotrophic microorganisms. The locations of organic carbon, gas, or light supply may be chosen strategically for a plurality of reasons such as, but not limited to the growth characteristics of the culture (e.g., growth rate, nutrient consumption rate). The organic carbon source may also be supplied at locations for continuous consumption by a culture of a determined density and traveling at a determined velocity so that the residual organic carbon in the aqueous culture medium is sustained at a low level (50-1,000 ppm) to limit the feed sources available to contaminating organisms (e.g., fungi, predators, bacteria).

In some embodiments, the organic carbon source may be supplied to the culture of mixotrophic microorganisms when the dissolved oxygen level is above the predetermined threshold level to induce an increase in the consumption of oxygen through the heterotrophic metabolism of the microorganisms. In some embodiments, the organic carbon source may be supplied to the culture of mixotrophic microorganisms to maintain the pH level in a desired pH range. In some embodiments, an organic carbon source with an acidic pH may be supplied to the culture of mixotrophic microorganisms when the pH is above the predetermined threshold level to decrease the pH level to within a desired pH range. In some embodiments, an organic carbon with a basic pH may be supplied to the culture of mixotrophic microorganisms when the pH is below the predetermined threshold level to increase the pH level to within a desired pH range. In some embodiments, the organic carbon source may be supplied to the culture of mixotrophic microorganisms when the dissolved carbon dioxide level is below the predetermined threshold level to induce an increase in the production of carbon dioxide through the heterotrophic metabolism of the microorganisms. In some embodiments, the amount of organic carbon supplied may be limited to an amount that may be readily assimilated by the primary mixotrophic microorganisms of the culture, thus reducing the residual organic carbon in the system available to the contaminating organisms in the culture.

In some embodiments, carbon dioxide may be supplied to the culture of mixotrophic microorganisms when the dissolved oxygen level is below the predetermined threshold level to induce an increase in the production of oxygen through the phototrophic metabolism of the microorganisms. In some embodiments, carbon dioxide may be supplied to the culture of mixotrophic microorganisms when the pH is above the predetermined threshold level to decrease the pH level to within a desired pH range.

In some embodiments, the amount, intensity, and/or specific wavelength spectrum of light may be adjusted if the dissolved oxygen, dissolved carbon dioxide, or pH level is outside of an acceptable range of the predetermined threshold level. The amount, intensity, and/or specific wavelength of light may be adjusted to increase the production of oxygen through the photosynthetic metabolism of the mixotrophic microorganism, such as by increasing the amount of light and/or switching to primarily the red wavelength spectrum with some light in the blue wavelength spectrum. In some embodiments, the amount of light may be adjusted by changing between pulsed or flashing light and continuous light. The amount, intensity, and/or specific wavelength of light may be adjusted to decrease the production of oxygen through the photosynthetic metabolism of the mixotrophic microorganism, such as by decreasing the amount of light, intensity of light, and/or switching to a wavelength spectrum other than red. In some embodiments, at least one of an amount and intensity of light may be increased when the detected dissolved oxygen level is below the predetermined threshold level. In some embodiments, at least one of an amount and intensity of light may be decreased when the detected dissolved oxygen level is above the predetermined threshold level.

When the culture density increases, as measured by optical density or turbidity, the demand for oxygen and carbon dioxide may increase and require the culture inputs to stimulate more metabolic activity to maintain a balanced gas composition. In some embodiments, at least one of an amount and intensity of light may be increased when the detected optical density or turbidity is above a predetermined threshold level. In some embodiments, the organic carbon supply may be increased when the detected optical density or turbidity is above a predetermined threshold level. In some embodiments, the supply of gas may be increased when the detected optical density or turbidity is above a predetermined threshold level.

In some embodiments, the culture of mixotrophic microorganisms may comprise a transition, turbulent, irregular or regular chaotic flow as the culture of microorganisms circulates in the bioreactor system. In some embodiments, the turbulent or other non-laminar flow may be provided by the velocity of the circulating culture medium, a mechanical mixing device, baffles on the surface of the culturing vessel, the pressure at which carbon dioxide or organic carbon is injected into the culture medium, and combinations thereof. In some embodiments, temperature may be monitored and adjusted within the culture by a heat exchanger such as, but not limited to, heating or cooling coils, or a shell and tube heat exchanger. In some embodiments, pressure within a closed bioreactor system may be monitored and adjusted within the bioreactor system.

In some embodiments, the balanced mixotrophy method of culturing mixotrophic microorganisms may be used to produce microorganism biomass for harvest. The microorganisms may be harvested by any known means such as, but not limited to, filtration, centrifugation, dissolved air flotation, foam fractionation, the application of electrical fields, the application of acoustic energy, and combination thereof. In some embodiments, the balanced mixotrophy method of culturing mixotrophic microorganisms may be used as a de-eutrophication method to remove nutrients (e.g., nitrates, phosphates) from a fluid stream.

In some embodiments, the bioreactor system may be run at a higher pressure and/or have a reservoir exposed to higher pressure to increase the saturation of the targeted gas thus enhancing the oxygen and/or carbon dioxide produced and consumed by the mixotrophic microorganisms. The increase in pressure within the bioreactor system increases the solubility of the gasses in solution, thus increasing the efficiency of oxygen/carbon dioxide utilization by the mixotrophic microorganisms.

In some embodiments, the pH, dissolved oxygen level, and carbon dioxide level of the culture in the bioreactor system may be operated in a steady state for at least one or all parameters. In some embodiments, the pH, dissolved oxygen level, and carbon dioxide level of the culture in the bioreactor system may be operated in a steady state for some parameters while at least one parameter fluctuates between ranged set points. For example, in one non-limiting embodiment the pH may be controlled through a set point (i.e., predetermined threshold level) on a feedback control loop while the dissolved oxygen level may be controlled and allowed to rise to the threshold of the mixotrophic microorganisms' tolerance level (e.g., a species of *Chlorella* has been observed to have a tolerance level of approximately 12 mg $O_2$/L but this value will be species specific). When the dissolved oxygen level reaches the set point (i.e., predetermined threshold level), the organic carbon supply may be increased to allow the mixotrophic microorganisms to consume the oxygen through the heterotrophic metabolism and reduce the dissolved oxygen level of the culture (ranging from saturation to 0 mg/L).

In some embodiments, the bioreactor system may be operated using methods of continuously balancing the gas composition in mixotrophic culture conditions and the mixotrophic microorganisms may be harvested for protein, lipid, pigment, carbohydrate, or polysaccharide products extracted or separated in downstream processing. In some embodiments, the light may be adjusted to stimulate pigment production during the balanced mixotrophy method to simultaneously increase targeted pigment (e.g., chlorophylls, carotenoids) during the growth phase of the microorganism culture.

Example 1

The flow chart in FIG. 1 describes a non-limiting exemplary embodiment implementing the controls for a balanced mixotrophy method which continually balances the gas composition of a culture of mixotrophic microorganisms. To begin the method, the dissolved oxygen (DO) and pH levels of the mixotrophic microorganism culture are detected. If the detected pH level is below the predetermined threshold level or set point, the carbon dioxide and organic carbon (e.g., acetic acid) supply is stopped or reduced. If the detected pH level is above the predetermined threshold level or set point, a determination is made as to whether the DO level is above or below the predetermined threshold level or set point. If the detected DO level is below the predetermined threshold level or set point, the carbon dioxide supply is started or increased to induce use of the phototrophic metabolism in the mixotrophic microorganism and the production of oxygen. If the detected DO level is above the predetermined threshold level or set point, the organic carbon (e.g., acetic acid) supply is started or increased to induce use of the heterotrophic metabolism in the microorganism and the production of carbon dioxide. The method may then loop to the beginning where DO and pH levels are measured, and the process steps are repeated. The frequency of measurements may be done at any reasonable time period for the sensors, including multiple times per hour or minute.

Example 2

A balanced mixotrophy method for continuously balancing the gas composition in a culture of mixotrophic microorganisms was tested using a tubular bioreactor system with a working volume of 400 L. The tubular bioreactor system comprised pump circulation through stacked horizontal tubes joined by U-shaped tubular joints, a de-gassing tank, with a light source consisting of arrays of fluorescent tubes, an organic carbon supply device dosing acetic acid, a carbon dioxide injection system, pH sensors, dissolved oxygen (DO) sensors, and a programmable logic control system (PLC). It is of note that the balanced mixotrophy method test did not use any injection or sparging of air into the bioreactor system.

The mixotrophic microorganism culture comprised a species of *Chlorella* in a BG-11 aqueous culture medium. The mixotrophic microorganism culture was continuously circulated through the tubular bioreactor system with sensors monitoring the pH and DO levels. The culture temperature was maintained within +/−5° C. of room temperature (approximately 25° C.). Fluorescent light was provided to the tubular bioreactor system at approximately 335 μmol photon/$m^2$ s in a 24 hour continuous photoperiod. The control logic for the acetic acid and carbon dioxide supply devices was the same as outlined in Example 1 and FIG. 1, with the predetermined threshold levels (i.e., set points) at 7.5 for pH and 4 mg $O_2$/L for DO. The DO and pH sensors detected the pH in the culture circulation at three points in the bioreactor system: before the de-gas tank, after the de-gas tank, and after the pump. The control logic of the PLC dosed acetic acid when the detected pH level was above the predetermined threshold level (i.e., 7.5) and the detected DO level was above the predetermined threshold level (i.e., 4 mg $O_2$/L). The control logic of the PLC dosed carbon dioxide when the detected pH level was above the predetermined threshold level (i.e., 7.5) and the detected DO level was below the predetermined threshold level (i.e., 4 mg $O_2$/L).

In tests conducted prior to the balanced mixotrophy method test, the test runs phototrophically culturing of *Chlorella* in the tubular bioreactor system with air sparging and no acetic acid created noticeable quantities of foam in the de-gas tank and were observed to operate at a high DO level (i.e., above 4 mg $O_2$/L). The high DO level in the prior phototrophic tests was controlled with $N_2$ sparging in various levels of concentration with the air.

Figure 2:
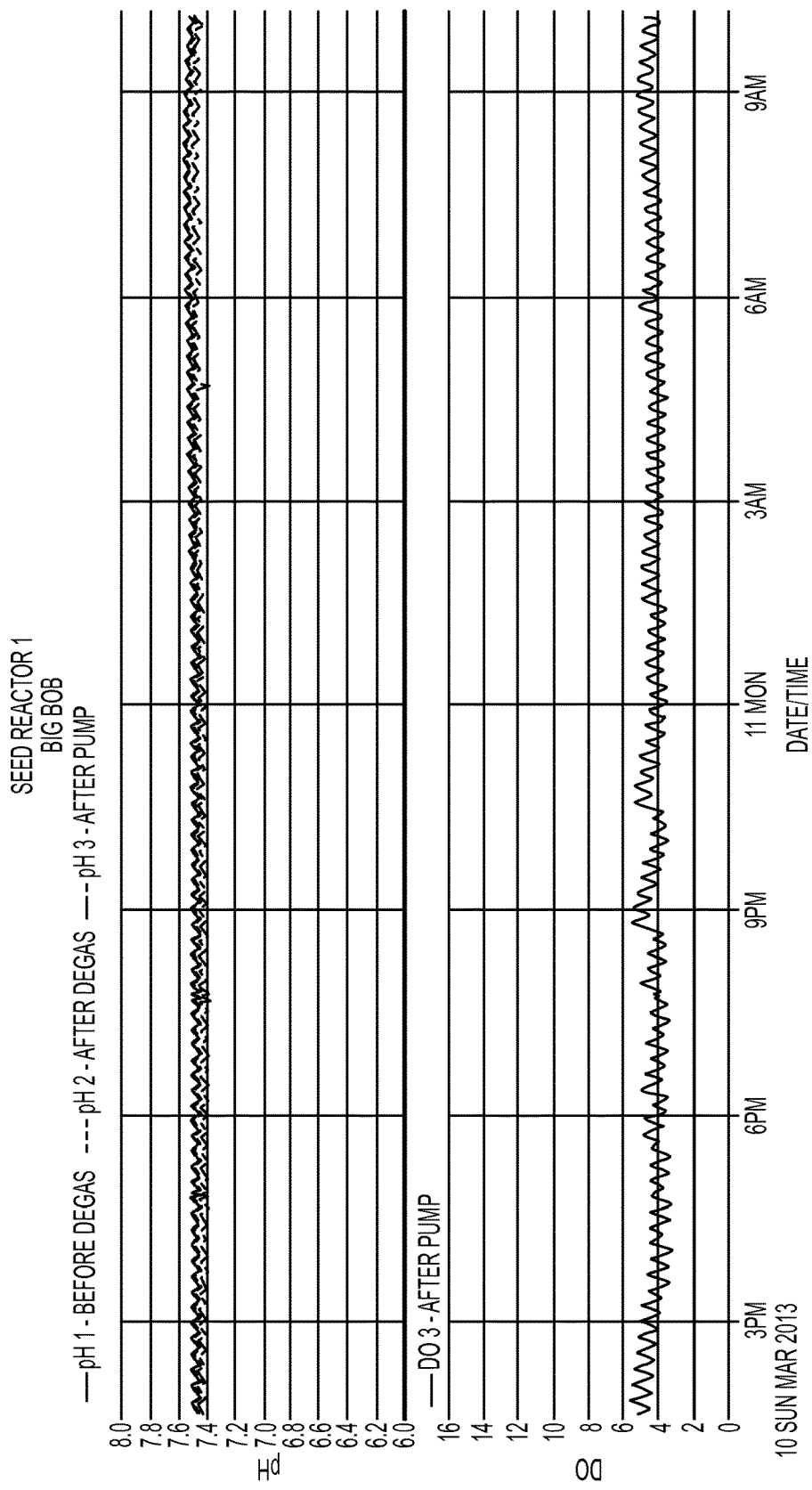
FIG. 2 shows the monitored dissolved oxygen and pH levels of culture of microorganisms in a balanced mixotrophy method.

During the balanced mixotrophy method test, air sparging was not utilized and a significant reduction in the amount of foam in the tubular bioreactor system was observed compared to test runs of the tubular bioreactor systems culturing *Chlorella* phototrophically with air sparging. As shown in FIG. 2, it was also observed that the DO level was able to be maintained in an acceptable range (+/−2 mg $O_2$/L) of the 4 mg $O_2$/L predetermined threshold level without the sparing of air. FIG. 2 also demonstrates that the pH level was able to be maintained within an acceptable range of the 7.5 (+/−0.1) predetermined threshold level using the acetic acid and carbon dioxide dosing.

Growth rates in prior phototrophic growth tests averaged 0.5 to 0.6 g/L per day when the tubular bioreactor system cultured microalgae phototrophically with air sparging. Growth rates for the first three days of the balanced mixotrophy method test without air sparging comprised 1.1 g/L, 1.2 g/L, and 1.25 g/L per day, with an average of 1.13 g/L per day over a six day period. The average growth rate of 1.13 g/L per day for the balanced mixotrophy tests was approximately two times the average of the growth rates obtained in the prior phototrophic growth tests with the tubular bioreactor system.

The growth rate data of 1.1 to 1.25 g/L per day was found to be consistent with the theorized growth rates if the mixotrophic microalgae are promptly consuming gas molecules (i.e., oxygen, carbon dioxide) created within the culture by the metabolisms of the microalgae. By using the balanced mixotrophy method, it was observed that the balanced gas composition of the culture reduced the foam to near imperceptible levels, which may reduce the potential for contamination and growth inhibition associated with the foam. The acetic acid supplied and consumed during the six day period of the balanced mixotrophy method averaged 5.36 Liters/Day, and resulted in an acetic acid efficiency of 1.89 g of acetic acid/g of microalgae biomass growth. The acetic acid efficiency of 1.89 g of acetic acid/g of microalgae biomass growth from the balanced mixotrophy method was better than the average of 3.5 g of acetic acid/g of microalgae biomass growth for previous tests with conventional mixotrophy methods comprising both air sparging and carbon dioxide injection.

Figure 3:
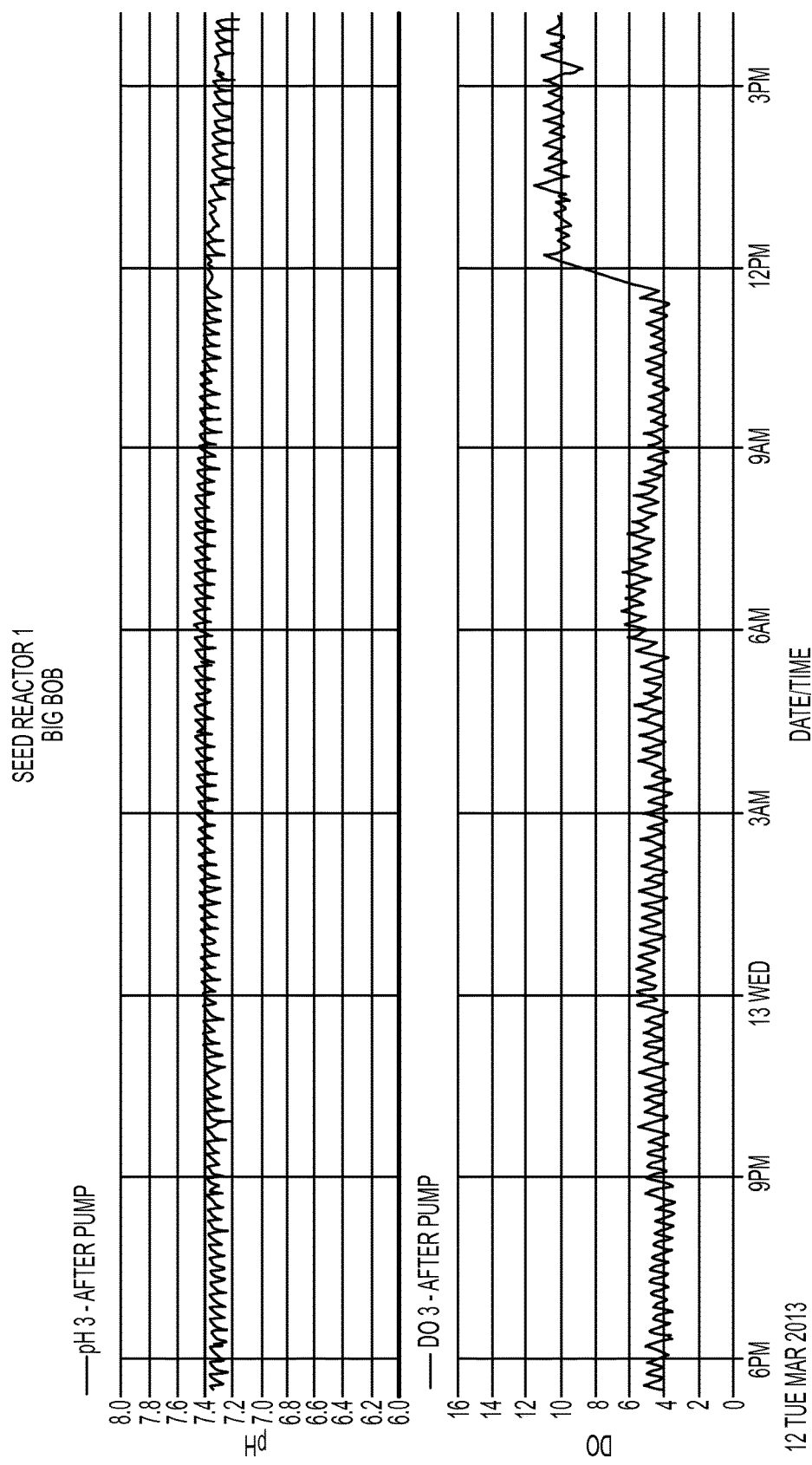
FIG. 3 shows the monitored dissolved oxygen and pH levels of culture of microorganisms in a balanced mixotrophy method.

As shown in FIG. 3, it was also observed that the pH level was able to be maintained within an acceptable range (+/−0.25) of the 7.5 predetermined threshold level using the acetic acid and carbon dioxide dosing of the balanced mixotrophy method when the DO predetermined threshold level (i.e., set point) was raised from 4 mg $O_2$/L to 10 mg $O_2$/L. When the DO predetermined threshold level was changed, the DO level quickly rose to the new predetermined threshold level of 10 mg $O_2$/L and was maintained within an acceptable range (+/−2 mg $O_2$/L) of the new predetermined threshold level.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of growing a mixotrophic culture of microorganisms, comprising:
   a. Providing a culture of mixotrophic microorganisms in an aqueous culture medium with a supply of carbon dioxide and a supply of organic carbon comprising at least one organic carbon source selected from the group consisting of acetic acid and acetate;
   b. Circulating the culture of mixotrophic microorganisms through a circulation path of a bioreactor system selected from the group consisting of a tubular bioreactor and a raceway pond, wherein the culture receives the supply of carbon dioxide and the supply of organic carbon in the circulation path;
   c. Detecting a pH level and a dissolved oxygen level in the culture with at least one sensor disposed along the circulation path;
   d. Continuously adjusting the supply of carbon dioxide and organic carbon to the culture based on the detected pH level and dissolved oxygen level in the culture, wherein:
      i. the carbon dioxide is supplied and the organic carbon is not supplied when the detected pH level is above a predetermined threshold level and the detected dissolved oxygen level is below a predetermined threshold level; and
      ii. the carbon dioxide is not supplied and the organic carbon is supplied when the detected pH level is above a predetermined threshold level and the detected dissolved oxygen level is above a predetermined threshold level.

2. The method of claim 1, wherein the culture of microorganisms comprises at least one selected from the group consisting of microalgae and cyanobacteria.

3. The method of claim 1, wherein a composition of the dissolved oxygen and dissolved carbon dioxide is balanced at the saturation point of the aqueous culture medium.

4. The method of claim 3, wherein the balanced composition of dissolved oxygen and dissolved carbon dioxide comprises oxygen at 25-200% of the saturation level of the aqueous culture medium and carbon dioxide at 25-500% of the saturation level of the aqueous culture medium.

5. The method of claim 1, wherein the predetermined threshold of dissolved oxygen level is in the range of 0.1-30 mg $O_2$/L.

6. The method of claim 5, wherein the predetermined threshold dissolved oxygen level is in the range of 1-6 mg $O_2$/L.

7. The method of claim 1, wherein the method further comprises transmitting data from the at least one sensor to a programmable logic control system to control the supply of carbon dioxide and the supply of organic carbon.

8. The method of claim 1, wherein culture does not receive an external supply of gas other than the selectively supplied carbon dioxide.

9. The method of claim 8, wherein the culture produces 85% more grams of microorganism biomass growth per gram of acetic acid than a culture receiving an external supply of gases.

10. The method of claim 1, wherein the predetermined threshold pH level is in the range of 6-9.

11. The method of claim 1, wherein the predetermined threshold pH level is in the range of 1-5.

12. The method of claim 1, wherein a residual organic carbon level in the culture is maintained in the range of 50-1,000 ppm.

13. The method of claim 1, wherein at least one of the supply of carbon dioxide and supply of organic carbon is supplied at a plurality of locations along the circulation path of the bioreactor system.

14. The method of claim 1, further comprising supplying light to the culture.

15. The method of claim 14, wherein the supply of light is increased when the organic carbon is not supplied.

16. The method of claim 14, wherein the supply of light is decreased when the organic carbon is supplied.

17. The method of claim 14, wherein the supply of light comprises an intensity ranging from 100-10,000 μmol photon/$m^2$s.

18. The method of claim 14, wherein the supply of light comprises a wavelength range between 300-800 nm.

19. The method of claim 14, wherein the supply of light comprises at least one of natural light and artificial light.

20. The method of claim 14, wherein light is supplied at a plurality of locations along the circulation path of the bioreactor system.

* * * * *